US008703639B2

(12) United States Patent
Wan et al.

(10) Patent No.: US 8,703,639 B2
(45) Date of Patent: Apr. 22, 2014

(54) OXIDATION CATALYST AND ITS USE FOR CATALYZING LIQUID PHASE OXIDATION REACTIONS

(75) Inventors: Kam-To Wan, Manchester, MO (US); Mark A. Leiber, St. Peters, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1466 days.

(21) Appl. No.: 11/575,370

(22) PCT Filed: Sep. 15, 2005

(86) PCT No.: PCT/US2005/032862
§ 371 (c)(1),
(2), (4) Date: Dec. 8, 2009

(87) PCT Pub. No.: WO2006/031938
PCT Pub. Date: Mar. 23, 2006

(65) Prior Publication Data
US 2010/0130774 A1   May 27, 2010

Related U.S. Application Data

(60) Provisional application No. 60/610,103, filed on Sep. 15, 2004, provisional application No. 60/619,501, filed on Oct. 15, 2004, provisional application No. 60/627,500, filed on Nov. 12, 2004.

(51) Int. Cl.
*B01J 23/38* (2006.01)
*C07F 9/22* (2006.01)

(52) U.S. Cl.
USPC .............................. 502/185; 502/184; 562/17

(58) Field of Classification Search
USPC ...................... 502/184, 185; 562/17
See application file for complete search history.

(56) References Cited

U.S. PATENT DOCUMENTS

| | | |
|---|---|---|
| 2,384,817 A | 9/1945 | Chitwood |
| 3,340,097 A | 9/1967 | Hess et al. |
| 3,799,758 A | 3/1974 | Franz |
| 3,835,000 A | 9/1974 | Frazier et al. |
| 3,871,998 A | 3/1975 | Rase et al. |
| 3,927,080 A | 12/1975 | Gaertner |
| 3,950,402 A | 4/1976 | Franz |
| 3,954,848 A | 5/1976 | Franz |
| 3,956,370 A | 5/1976 | Parry et al. |
| 3,969,398 A | 7/1976 | Hershman |
| 4,026,950 A | 5/1977 | Le Ludec |
| 4,147,719 A | 4/1979 | Franz |
| 4,186,110 A | 1/1980 | Jalan et al. |
| 4,190,605 A | 2/1980 | Muench et al. |
| 4,225,727 A | 9/1980 | Kamiyama et al. |
| 4,264,776 A | 4/1981 | Hershman et al. |
| 4,325,842 A | 4/1982 | Slaugh et al. |
| 4,325,843 A | 4/1982 | Slaugh et al. |
| 4,326,992 A | 4/1982 | Slaugh et al. |
| 4,333,916 A | 6/1982 | Iwai et al. |
| 4,345,038 A | 8/1982 | McCandlish et al. |
| 4,351,962 A | 9/1982 | Gradeff et al. |
| 4,415,479 A | 11/1983 | Puskas et al. |
| 4,476,102 A | 10/1984 | McCandish et al. |
| 4,486,356 A | 12/1984 | Bakel |
| 4,507,250 A | 3/1985 | Bakel |
| 4,522,708 A | 6/1985 | Leclercq et al. |
| 4,525,294 A | 6/1985 | Sartori et al. |
| 4,579,689 A | 4/1986 | Hershman et al. |
| 4,582,650 A | 4/1986 | Felthouse |
| 4,624,937 A | 11/1986 | Chou |
| 4,654,429 A | 3/1987 | Balthazor et al. |
| 4,696,772 A | 9/1987 | Chou |
| 4,775,498 A | 10/1988 | Gentilcore |
| 4,782,183 A | 11/1988 | Goto et al. |
| 4,794,054 A | 12/1988 | Ito et al. |
| 4,810,426 A | 3/1989 | Fields, Jr. et al. |
| 4,851,131 A | 7/1989 | Grabiak et al. |
| 4,921,991 A | 5/1990 | Lacroix |

(Continued)

FOREIGN PATENT DOCUMENTS

| | | |
|---|---|---|
| DE | 19600741 A1 | 7/1996 |
| EP | 0019445 A2 | 11/1980 |
| EP | 0019445 B1 | 11/1980 |
| EP | 0055695 A1 | 7/1982 |
| EP | 0098034 A2 | 4/1983 |
| EP | 0162035 A2 | 11/1985 |
| EP | 0408528 A1 | 1/1991 |
| EP | 0595124 A1 | 5/1994 |
| EP | 0680948 A1 | 11/1995 |
| EP | 0801978 A1 | 10/1997 |

(Continued)

OTHER PUBLICATIONS

Cameron, "Carbons as Supports for Precious Metal Catalysts", Catalysis Today, (1990), pp. 113-137, vol. 7.
Mallat, "Preparation of Promoted Platinum Catalysts of Designed Geometry and the Role of Promoters in the Liquid-Phase Oxidation of 1-Methoxy-2-Propanol", Journal of Catalysis, (1993), pp. 237-253, vol. 342.
International Search Report from the European Patent Office in connection with International Application No. PCT/US99/03402 dated Feb. 17, 1999.

(Continued)

*Primary Examiner* — Samantha Shterengarts
(74) *Attorney, Agent, or Firm* — Senniger Powers LLP; Joseph A. Schaper

(57) ABSTRACT

This invention relates to the field of heterogeneous catalysis, and more particularly to oxidation catalysts including carbon supports having deposited thereon a noble metal and one or more optional promoters and to methods for their preparation. The invention further relates to the field of heterogeneous catalytic oxidation reactions, including the preparation of secondary amines by the catalytic oxidation of tertiary amines, such as the oxidation of an N-(phosphonomethyl) iminodiacetic acid to produce an N-(phosphonomethyl)glycine product.

41 Claims, 22 Drawing Sheets

(56) References Cited

U.S. PATENT DOCUMENTS

| | | | |
|---|---|---|---|
| 4,970,128 | A | 11/1990 | Itoh et al. |
| 4,978,649 | A | 12/1990 | Surovikin et al. |
| 5,023,369 | A | 6/1991 | Fields, Jr. |
| 5,024,905 | A | 6/1991 | Itoh et al. |
| 5,077,431 | A | 12/1991 | Fields, Jr. |
| 5,079,107 | A | 1/1992 | Jalan |
| 5,087,740 | A | 2/1992 | Smith |
| 5,091,561 | A | 2/1992 | Riley et al. |
| 5,095,140 | A | 3/1992 | Fields, Jr. |
| 5,096,866 | A | 3/1992 | Itoh et al. |
| 5,112,787 | A | 5/1992 | Falke et al. |
| 5,178,971 | A | 1/1993 | Itoh et al. |
| 5,179,228 | A | 1/1993 | Ramon et al. |
| 5,189,005 | A | 2/1993 | Watanabe et al. |
| 5,225,391 | A | 7/1993 | Stonehart et al. |
| 5,292,936 | A | 3/1994 | Franczyk |
| 5,338,716 | A | 8/1994 | Triplett et al. |
| 5,356,849 | A | 10/1994 | Matviya et al. |
| 5,367,112 | A | 11/1994 | Franczyk |
| 5,372,981 | A | 12/1994 | Witherspoon |
| 5,410,085 | A | 4/1995 | Birkenstock et al. |
| 5,427,761 | A | 6/1995 | Grindatto et al. |
| 5,500,485 | A | 3/1996 | Hodgkinson |
| 5,585,083 | A | 12/1996 | Kielin et al. |
| 5,602,276 | A | 2/1997 | Stern et al. |
| 5,606,107 | A | 2/1997 | Smith |
| 5,627,125 | A | 5/1997 | Ebner et al. |
| 5,658,839 | A | 8/1997 | de Agudelo et al. |
| 5,688,994 | A | 11/1997 | Baysdon et al. |
| 5,739,390 | A | 4/1998 | Franczyk |
| 5,759,944 | A | 6/1998 | Buchanan et al. |
| 5,783,737 | A | 7/1998 | Metivier |
| 5,876,867 | A | 3/1999 | Itoh et al. |
| 5,882,619 | A | 3/1999 | Heineke et al. |
| 5,989,648 | A | 11/1999 | Phillips |
| 6,005,140 | A | 12/1999 | Morgenstern et al. |
| 6,153,753 | A | 11/2000 | Johnson et al. |
| 6,278,017 | B1 | 8/2001 | Stern et al. |
| 6,376,708 | B1 | 4/2002 | Morgenstern et al. |
| 6,417,133 | B1 * | 7/2002 | Ebner et al. ............ 502/185 |
| 6,436,816 | B1 | 8/2002 | Lee et al. |
| 6,528,680 | B1 | 3/2003 | Aust et al. |
| 6,689,711 | B2 | 2/2004 | Lefebvre |
| 6,696,384 | B2 | 2/2004 | McCrae et al. |
| 6,764,874 | B1 | 7/2004 | Zhang et al. |
| 7,291,751 | B2 | 11/2007 | Leiber et al. |
| 2001/0002424 | A1 | 5/2001 | Siebenhaar et al. |
| 2002/0068836 | A1 | 6/2002 | Haupfear et al. |
| 2002/0121460 | A1 | 9/2002 | Moy et al. |
| 2003/0171611 | A1 | 9/2003 | Leiber |
| 2003/0228972 | A1 | 12/2003 | Birss et al. |
| 2003/0229246 | A1 | 12/2003 | Leiber et al. |

FOREIGN PATENT DOCUMENTS

| | | |
|---|---|---|
| EP | 1067108 A2 | 1/2001 |
| EP | 1236509 A1 | 9/2002 |
| FR | 2798079 A1 | 9/1999 |
| FR | 2798135 A1 | 9/1999 |
| GB | 1468109 | 3/1977 |
| GB | 1601715 | 11/1981 |
| WO | 9532150 A1 | 11/1995 |
| WO | 9619485 A1 | 6/1996 |
| WO | 9835930 A1 | 8/1998 |
| WO | 9941260 A1 | 8/1999 |
| WO | 9943430 | 9/1999 |
| WO | 0001707 A1 | 1/2000 |
| WO | 0009517 | 2/2000 |
| WO | 0062926 A1 | 10/2000 |
| WO | 0107447 A1 | 2/2001 |
| WO | 0128679 A1 | 4/2001 |
| WO | 0192272 A2 | 12/2001 |
| WO | 02098557 A1 | 12/2002 |
| WO | 03068387 A1 | 8/2003 |

OTHER PUBLICATIONS

CRC Handbook of Chemistry and Physics, 79th Edition, 1998, "Ionization Potentials of Atoms and Atomic Ions", pp. 10-175 to 10-176, D.R. Lide, Ed., CRC Press, Boca Raton, FL.

Park, S., et al., "Electrocatalytic Pathways on Carbon-Supported Platinum Nanoparticles: Comparison of Particle-Size-Dependent Rates of Methanol, Formic Acid, and Formaldehyde Electroxidation," Langmuir, 2002, pp. 5792-5798, vol. 18.

Lalande, G. et al., "Chromium-Based Electrocatalysts for Oxygen Reduction in Polymer Electrolyte Fuel Cells," New Materials for Fuel Cell and Modern Battery Systems II, Proceedings of the International Symposium on New Materials for Fuel Cell and Modern Battery Systems, 2nd Montreal, (1997), pp. 768-777, Ecole Polytechnique De Montreal, Montreal Que.

Franz, J.E. et al., "Glyphosate: A Unique Global Herbicide, Chapter 8—Methods of Preparing Glyphosate," American Chemical Society, (1997), pp. 233-262, Washington, D.C.

Grasselli, R. et al., "Selective Oxidation of Hydrocarbons with Heterogeneous Catalysts Containing Tellurium," Proc. Int. Symp. Uses Selenium Tellurium, (1989), 4th, pp. 609-632, Selenium-Tellurium Dev. Assoc., Darien, Conn.

Lalande, G., et al., "Electroreduction of Oxygen in Polymer Electrolyte Fuel Cells by Activated Carbon Coated Cobalt Nanocrystallites Produced by Electric Arc Discharge, " Chemistry of Materials, (1997), pp. 784-790, vol. 9:3, American Chemical Society.

Mallat T. et al., "Oxidation of Alcohols with Molecular Oxygen on Platinum Metal Catalysts in Aqueous Solutions," Catalysis Today, (1994), pp. 247-284, vol. 19.

Kim, D.W. et al., "CoMo Bimetallic Nitride Catalysts for Thiophene HDS," Catalysis Letters, (1997), pp. 91-95, vol. 43:1-2, J.C. Baltzer AG, Science Publishers.

International Search Report from the European Patent Office in connection with International Application No. PCT/US00/34875 dated Jul. 10, 2001.

Takano, I. et al., "Nitrogenation of Various Transition Metals by N2+-Ion Implantation," Applied Surface Science, (1989), pp. 25-32, vol. 37, Elsevier Science Publishers B.V., North-Holland, Amsterdam.

Bridgewater, A.J. et al., "Reactions of Carbon Monoxide with Hydrogen Over Molybdenum/Charcoal Catalysts," Journal of Catalysis, (1982), pp. 116-125, vol. 78.

Cote, R. et al., "Non-Noble Metal-Based Catalysts for the Reduction of Oxygen in Polymer Electrolyte Fuel Cells," Journal of New Materials for Electrochemical Systems I, (1998), pp. 7-16.

Dandekar A. et al., "Carbon-Supported Copper Catalysts," Journal of Catalysis, (1999), pp. 131-154, vol. 183, Academic Press.

Faubert, G. et al., "Iron Catalysts Prepared by High-Temperature Pyrolysis of Tetraphenylporphyrins Adsorbed on Carbon Black for Oxygen Reduction in Polymer Electrolyte Fuel Cells," Electrochimica Acta., (1998), pp. 341-353, vol. 43:3-4, Elsevier Science Ltd. Great Britain.

Faubert, G. et al., "Activation and Characterization of Fe-Based Catalysts for the Reduction of Oxygen in Polymer Electrolyte Fuel Cells," Electrochimica Acta., (1998), pp. 1969-1984, vol. 43:14-15, Elsevier Science Ltd., Great Britain.

Faubert, G. et al., "Oxygen Reduction Catalysts for Polymer Electrolyte Fuel Cells from the Pyrolysis of FeII Acetate Absorbed on 3,4,9,10-Perylenetetracarboxylic Dianhydride," Electrochimica Acta, (1999), pp. 2589-2603, vol. 44, Elsevier Science Ltd.

Lalande, G. et al., "Catalytic Activity and Stability of Heat-Treated Iron Phthalocyanines for the Electroreduction of Oxygen in Polymer Electrolyte Fuel Cells," Journal of Power Sources, (1996), pp. 227-237, vol. 61, Elsevier Science S.A.

Granger, P. et al., "Kinetics of the NO And CO Reaction Over Platinum Catalysts," Journal of Catalysis, (1998), pp. 304-314, Academic Press.

He, P. et al., "Oxygen Reduction Catalysts for Polymer Electrolyte Fuel Cells From the Pyrolysis of Various Transition Metal Acetates Adsorbed on 3,4,9,10-Perylenetetracarboxylic Dianhydride," Journal of New Material for Electrochemical Systems, (1999), pp. 243-251, vol. 2, Journal of New Material Electrochemical Systems.

(56) References Cited

OTHER PUBLICATIONS

Kimbara, N. et al., "New Type of TiN Support for Hydroprocessing Catalyst Yst.," Catal. Lett., (1990), pp. 3-6, vol. 6 (Abstract only).
Toda, T. et al., "Enhancement of the Electroreduction of Oxygen on Pt Alloys with Fe, Ni, and Co," Journal of the Electrochemical Society, (1999), pp. 3750-3756, vol. 146:10.
Torrens, M. A., "Mossbauer Studies on Oxo-Bridged Iron (III) Porphines," Journal of the American Chemical Society, (1972), pp. 4160-4162, vol. 94:12.
Levy, R. B. et al., "Platinum-Like Behavior of Tungsten Carbide in Surface Catalysis," Science, (1973), pp. 547-549, vol. 181.
Van Der Putten, A. et al., "Oxygen Reduction on Pyrolysed Carbon-Supported Transition Metal Chelates," Journal of Electroanalytical Chemistry and Interfacial Electrochemistry, (1986), pp. 233-244, vol. 205, Elsevier Sequoia S.A. Lausanne, The Netherlands.
Van Veen, J. A. R. et al., "On the Effect of a Heat Treatment on the Structure of Carbon-Supported Metalloporphyrins and Phthalocyanines", Electrochimica Acta, (1988), pp. 801-804, vol. 33:6, Pergamon Press plc., Great Britain.
Mordent!, D. et al.,"New Synthesis of Mo2C 14 nm in Average Size Supported on a High Specific Surface Area Carbon Material," Journal of Solid State Chemistry, (1998), pp. 114-120, vol. 141, Academic Press.
Murav'Ev, V. I., "Carbonitriding in a Fluidized Bed of Carbon-Graphite Materials," Metal Science and Heat Treatment, (1976), pp. 492-495, vol. 18:5-6, Consultants Bureau, New York.
Van Veen, J. A. R. et al., "Effect of Heat Treatment on the Performance of Carbon-supported Transition-metal Chelates in the Electrochemical Reduction of Oxygen", J. Chem Soc., Faraday Trans. 1, (1981), pp. 2827-2843, vol. 77, The Royal Society of Chemistry, United Kingdom.
Weng, L. T. et al., "Characterization of Electrocatalysts for Oxygen Reduction by TOF SIMS," Secondary Ion Mass Spectrometry, Proceedings of the International Conference on Secondary Ion Mass Spectrometry, 9th, Yokohama, (1994), pp. 442-445, Wiley, Chichester, United Kingdom.
Oyama, S. T. et al., "Preparation and Characterization of Early Transition-Metal Carbides and Nitrides," Industrial & Engineering Chemistry Research, (1988), pp. 1639-1648, vol. 27: 9, American Chemical Society.
Oyama, S. T. "Preparation and Catalytic Properties of Transition Metal Carbides and Nitrides," Catalysis Today, (1992), pp. 179-200, vol. 15, Elsevier Science Publishers, B. V., Amsterdam.
Sedunov, V. K. et al., "Structure and Phase Composition of Surface Zones of Carburized and Carbonitrided Layers," Metal Science and Heat Treatment, (1977), pp. 742-745, vol. 19:9-10, Consultants Bureau, New York.
Wang, H. et al., "Effect of the Pre-Treatment of Carbon Black Supports on the Activity of Fe-Based Electocatalysts for the Reduction of Oxygen," Journal of Physical Chemistry B, (1999), pp. 2042-2049, vol. 103, American Chemical Society.
Alves, M.C.M. et al., "Characterization of New Systems for the Catalytic Electroreduction of Oxygen by Electrochemistry and X-Ray Absorption Spectroscopy," NATO ASI Series, Series C: Mathematical and Physical Sciences, Synchrotron Techniques in Interfacial Electrochemistry, (1994), pp. 281-293, vol. 432, Kluwer Academic Press, The Netherlands.
Bett, J.S. et al., "Platinum-macrocycle Co-catalysts for the Electrochemical Oxidation of Methanol," Electrochimica Acta, (1998), pp. 3645-3655, vol. 43:24, Elsevier Science Ltd., Great Britain.
Weng, L.T. et al., "Surface Characterization by Time-of-Flight SIMS of a Catalyst for Oxygen Electroreduction: Pyrolyzed Cobalt Phthalocyanine-On-Carbon Black," Applied Surface Science, (1995), pp. 9-21, vol. 84, Elsevier Science B.V.
Bouwkamp-Wijnoltz, A.L. et al., "Electrochemical Reduction of Oxygen: An Alternative Method to Prepare Active CoN4 Catalysts," Electrochimica Acta., (1999), pp. 379-386, vol. 45.

Singh, A. et al., "X-Ray Photoelectron Spectroscopy of Nitrogen-Implanted Cemented Tungsten Carbide (WC-CO)," Journal of Materials Science Letters, (1990), pp. 1101-1102, vol. 9, Chapman and Hall Ltd.
Collman, J.P. et al., "Electrode Catalysis of the Four-Electron Reduction of Oxygen to Water by Dicobalt Face-to-Face Porphyrins," Journal of American Chemical Society, (1980), pp. 6027-6036, vol. 102, American Chemical Society.
Deng, C. Z. et al., "Sputtered Cobalt-Carbon-Nitrogen Thin Films as Oxygen Reduction Electrocatalysts", J. Electrochem. Soc., (1998), pp. 3507-3512, vol. 145:10.
Dignard-Bailey, L. et al., "Graphitization and Particle Size Analysis of Pyrolyzed Cobalt Phthalocyanine/Carbon Catalysts for Oxygen Reduction in Fuel Cells," Journal of Materials Research, (1994), pp. 3203-3209, vol. 9:12, Materials Research Society.
Durand, R.R. et al., "Catalysis of Dioxygen Reduction at Graphite Electrodes by an Adsorbed Cobalt(II) Porphyrin", Journal of Electroanalytical Chemistry, (1982), pp. 273-289, vol. 134:2, Elsevier Sequoia S.A., Lausanne, The Netherlands.
Ewen, R.J. et al., "X-Ray Photoelectron Spectroscopy of Clean and Gas-Doped Films of Phthalocyanines", Journal of Physics Condensed Matter, (1991), pp. S303-S310, vol. 3,1OP Publishing Ltd., An Institute of Physics Journal, United Kingdom.
Faubert, G. et al., "Heat-Treated Iron and Cobalt Tetraphenylporphyrins Adsorbed on Carbon Black: Physical Characterization and Catalytic Properties of these Materials for the Reduction of Oxygen in Polymer Electrolyte Fuel Cells", Electrochimica Acta, (1996), pp. 1689-1701, vol. 41:10, Elsevier Science Ltd., Great Britain.
Fournier, J. et al., "Activation of Various Fe-Based Precursors on Carbon Black and Graphite Supports to Obtain Catalysts for the Reduction of Oxygen in Fuel Cells," J. Electrochem. Soc., (1997), pp. 218-226, Vol. 144:1.
Gupta, S. et al., "Methanol-Tolerant Electrocatalysts for Oxygen Reduction in a Polymer Electrolyte Membrane Fuel Cell", J. Appl. Electrochem., (1998), pp. 673-682, vol. 28:7.
Hirai, T. et al., "The Influence of Catalyst-Supporting Methods on Electrochemical Activity and the Resultant Stability of Air Electrodes Activated with Iron Pythalocyanine", Journal of Applied Electrochemistry, (1985), pp. 441-445, Chapman and Hall Ltd.
Lalande, G. et al., "Is Nitrogen Important in the Formulation of Fe-based Catalysts for Oxygen Reduction in Solid Polymer Fuel Cells?," Electrochimica Acta., (1997), pp. 1379-1388, Vol. 42:9, Great Britain.
Lalande, G. et al., "Rotating Disk Electrode Measurements on the Electrocatalytic Activity of Heat-Treated Carbon Supported Cobalt Phthalocyanine Catalysts for Oxygen Reduction," Electrochemical Society Proceedings, (1994), pp. 418-429, Electrochemical Society.
Lefevre, M. et al., "Functionalities of a Fe-Based Catalyst Evidenced by ToF-SIMS in Relation with the Electroreduction of Oxygen in Polymer Electrolyte Fuel Cells," Secondary Ion Mass Spectrometry, SIMS XII, Proceedings of the International Conference on Secondary Ion Mass Spectrometry, (1999), pp. 447-450, Elsevier Science, Amsterdam, Netherlands.
Lin, W.-F. et al., "On-Line FTIR Spectroscopic Investigations of Methanol Oxidation in a Direct Methanol Fuel Cell", J. Electrochem. Soc., (1997), pp. 1917-1922, Vol. 144:6.
Markusse, A.P. et al., "Platinum Deactivation: in situ EXAFS During Aqueous Alcohol Oxidation Reaction," Catalysts Letters, (1998), pp. 141-145.
Milad, Issa K. et al., "A Comparison of Bulk Metal Nitride Catalysts for Pyridine Hydrodenitrogenation," Catalysis Letters, (1998), pp. 113-119, vol. 52:1-2, J.C. Baltzer AG, Science Publishers.
Mukerjee, S. et al., "An In Situ X-Ray Absorption Spectroscopy Investigation of the Effect of Sn Additions to Carbon-Supported Pt Electrocatalysts," Journal of the Electrochemical Society, (1999), pp. 600-606, vol. 146:2.
Nishihara, H. et al., "Electrochemical Olefin Epoxidation with Manganese meso-Tetraphenylporphyrin Catalyst and Hydrogen Peroxide Generation at Polymer-Coated Electrodes," Inorganic Chemistry, (1990), pp. 1000-1006, vol. 29:5, American Chemical Society.

(56) References Cited

OTHER PUBLICATIONS

Okada, T. et al., "Oxygen Reduction Characteristics of Heat-Treated Catalysts Based on Cobalt-Porphyrin Ion Complexes," J. Electrochem. Soc., (1998), pp. 815-822, Vol. 145:3.

Pinel, C. et al., "Effect of the Nature of Carbon Catalysts on Glyphosate Synthesis," Academic Press, (1999), pp. 515-519.

Jasinski, R., "Cobalt Phthalocyanine as a Fuel Cell Cathode", Journal of the Electrochemical Society, (1965), pp. 526-528, Vol. 112:5.

International Search Report and Written Opinion issued in connection with PCT/US2005/032862, dated Apr. 26, 2006.

Alvarez-Merino, M., et al., "Tungsten Catalysts Supported on Activated Carbon," Journal of Catalysis, 2000, pp. 363-373, vol. 192, Academic Press.

Birss, V. I., et al., "Non-Noble Metal Catalysts for PEM Oxygen Reduction Based on Sol Gel Derived Cobalt Nigrogen Compounds," Electrochemical Society Proceedings, (2002), pp. 89-98, vol. 2002-31, Electrochemical Society.

Bouwkamp-Wijnoltz, A.L., et al., "On Active-Site Heterogeneity in Pyrolyzed Carbon-Supported Iron Porphyrin Catalysts for the Electrochemical Reduction of Oxygen: An In Situ Mossbauer Study," J. Phys. Chem., (2002), pp. 12993-13001, vol. 106:50.

Okada, T., et al., "Oxygen Reduction Characteristics of Graphite Electrodes Modified with Cobalt Di-Quinolyldiamine Derivatives," Electrochimica Acta, (2000), pp. 4419-4428, vol. 45, Elsevier Science Ltd., Great Britain.

Lefévre, M., et al., "Molecular Oxygen Reduction in PEM Fuel Cells: Evidence for the Simultaneous Presence of Two Active Sites in Fe-Based Catalysts," Journal of Physical Chemistry, (2002), pp. 8705-8713, vol. 106:34.

Lefévre, M., et al., "02 Reduction in PEM Fuel Cells: Activity and Active Site Structural Information for Catalysts Obtained by the Pyrolysis at High Temperature of Fe Precursors," Journal of Physical Chemistry B, (2000), pp. 11238-11247, vol. 104, American Chemical Society.

Liang, C., et al., "Activated Carbon Supported Bimetallic CoMo Carbides Synthesized by Carbothermal Hydrogen Reduction," Carbon, (2003), pp. 1833-1839, vol. 41, Elsevier Science.

Lin, C. A., et al., "Characterization of Boron-Nitride-Supported Pt Catalysts for the Deep Oxidation of Benzene," Journal of Catalysis, (2002), pp. 39-45, vol. 210, Elsevier Science, USA.

Lin, W.-F., et al., "On-Line FTIR Spectroscopic Investigations of Methanol Oxidation in a Direct Methanol Fuel Cell," J. Electrochem. Soc., (1997), pp. 1917-1922, vol. 144:6.

Nagai, M., et al., "Catalytic Activity and Surface Properties of Nitride Molybdena-Alumina for Carbazole Hydrodenitrogenation," Journal of Catalysis, (2000), pp. 128-137, vol. 191, Academic Press.

Nhut, J.M., et al., "Synthesis and Catalytic Uses of Carbon and Silicon Carbide Nanostructures," Catalysis Today, (2002), pp. 11-32, vol. 76, Elsevier Science B. V.

Ohta, R., et al., "Origin of N 1s Spectrum in Amorphous Carbon Nitride Obtained by X-Ray Photoelectron Spectroscopy," Thin Solid Films, (2003), pp. 296-302, vol. 434, Elsevier.

Andrew, M.R. et al., "The Characterization of Pt/Sn Catalyst for the Electrochemical Oxidation of Methanol", Journal of Applied Electrochemistry, (1976), pp. 99-106, vol. 6.

Aricò, A.S. et al., "Methanol Oxidation on Carbon-Supported Pt-Sn Electrodes in Silicotungstic Acid", Electrochimica Acta., (1994), pp. 691-700, vol. 39:5.

Balakrishnan, K. et al., "A Chemisorption and XPS Study of Bimetallic Pt-Sn/Al2O3 Catalysts", Journal of Catalysis, (1991), pp. 287-306, vol. 127.

Burch, R., "The Oxidation State of Tin and the Interaction Between Platinum and Tin", Journal of Catalysis, (1981), pp. 348-359.

Ponec, V. et al., Preparation and Characterization of Metal and Alloy Catalysts, Studies in Surface Science and Catalysis; Catalysis by Metal and Alloys, Ch.7, pp. 299-391, vol. 95 (Delman, B., et al., eds, Elsevier Science B.V., Amsterdam, Netherlands).

Campbell, S. et al., "Effect of Bi and Sn Adatoms on Formic Acid and Methanol Oxidation at Well Defined Platinum Surfaces", Journal of Chemical Society, Faraday Trans., (1992), pp. 833-841, vol. 88:6.

Cathro, K.J., "The Oxidation of Water-Soluble Organic Fuels Using Platinum-Tin Catalysts", J. Electrochem. Soc.: Electrochemical Technology, (1969), pp. 1608-1611, vol. 116:11.

Coloma, F. et al., "Heat-Treated Carbon Blacks as Supports for Platinum Catalysts", Journal of Catalysis, (1995), pp. 299-305, vol. 154.

Coloma, F. et al., "Preparation of Platinum Supported on Pregraphitized Carbon Blacks", Langmuir, (1994), pp. 750-755, Vol. 10.

Dubinin, M.M., " Microporous Structures of Carbonaceous Adsorbents", Carbon, (1982), pp. 195-200, vol. 20:3.

Franklin, T. et al., "The Effect of Anionic Poisons on the Catalytic Oxidation of Formaldehyde on Platinum", Journal of Catalysis, (1976), pp. 360-366, Vol. 42.

Gallezot, P. et al., "Catalytic Oxidations with Air for Clean and Selective Transformations of Polyols", Catalysis of Organic Reactions, (1994), pp. 331-340, (Scaros et al., eds. Marcel Dekker, Inc., New York, NY).

Gökagac, G. et al., "Characterisation of Carbon-Supported Pt-Sn Bimetallic Catalysts for the Electrochemical Oxidation of Methanol", Journal of Chemical Society, (1993), pp. 151-157, vol. 89:1, Faraday Trans.

Kim, K.T. et al., "Surface and Catalytic Properties of Iron-Platinum/Carbon Electrocatalysts for Cathodic Oxygen Reduction in PAFC", J. Electrochem. Soc., (1993), pp. 31-36, 1993, vol. 140:1.

Kim, T.K. et al., "Preparation of Carbon-Supported Platinum Catalysts: Adsorption Mechanism of Anionic Platinum Precursor onto Carbon Support", Carbon, (1992), pp. 467-475, vol. 30:3.

Kimura, H. et al., "Palladium Based Multi-Component Catalytic Systems for the Alcohol to Carboxylate Oxidation Reaction", Applied Catalysis A: General, (1993), pp. 143-169, vol. 95.

Kimura, H., "Selective Oxidation of Glycerol on a Platinum-bismuth Catalyst by Using a Fixed Bed Reactor", Applied Catalysis A: General, (1993), pp. 147-158, vol. 105,.

Luk'Yanova, Z.V. et al., "Determination of the Surface Area of Platinum in Adsorption Catalysts from the Amount of 'Soluble' Platinum", Russian Journal of Physical Chemistry, (1979), pp. 225-227, vol. 53:2.

Maier, L., "Organic Phosphorus Compounds 95. A Simple Method for the Preparation of N-Dihydroxyphosphonylmethyl-Glycine (Glyphosate)", Phosphorus, Sulfur, and Silicon, (1991), pp. 65-67, Vol. 61.

Watanabe, M. et al., "Electrocatalysis by Ad-Atoms: Part XIII. Preparation of Ad-electrodes with Tin Ad-Atoms for Methanol, Formaldehyde and Formic Acid Fuel Cells", J. Electroanal. Chem., (1985), pp. 367-375, vol. 191.

Margitfalvi, J. et al., "Supported Bimetallic Catalysts Prepared by Controlled Surface Reactions", Ch.11, pp. 373-409.

Merlen, E. et al., "Characterization of Bimetallic Pt-Sn/Al2O3 Catalysts: Relationship Between Particle Size and Structure", Journal of Catalysis, (1996), pp. 178-188, vol. 159.

Prado-Burguette, C. et al., "Effect of Carbon Support and Mean Pt Particle Size on Hydrogen Chemisorption by Carbon-Supported Pt Catalysts", Journal of Catalysis, (1991), pp. 397-404, vol. 128.

Prado-Burgette, C. et al., "The Effect of Oxygen Surface Groups of the Support on Platinum Dispersion in Pt/Carbon Catalysts", Journal of Catalysis, pp. 98-106, Vol. 115.

Riley, D. et al., "Vanadium (IV,V) Salts As Homogeneous Catalysts for the Oxygen Oxidation of N-(Phosphonomethyl)Iminodiacetic Acid to N-(Phosphonomethyl)Glycine", Inorg. Chem, (1991), pp. 4191-4197, Vol. 30.

Riley, D. et al., "Homogeneous Catalysts for Selective Molecular Oxygen Driven Oxidative Decarboxylations", J. Am. Chem. Soc., (1991), pp. 3371-3378, vol. 113.

Rodríguez-Reinoso, F. et al. , "Platinum Catalysts Supported on Activated Carbons", Journal of Catalysis, (1986), pp. 171-183, vol. 99.

(56) References Cited

OTHER PUBLICATIONS

Shekhobalova, V.I., "Effect of Small Additions of KI on the Properties of Pt Adsorption Catalysts", Russian Journal of Physical Chemistry, (1984), p. 1759, vol. 58:11.

Shekhobalova, V.I. et al., "Deactivation Mechanism of Platinum Catalysts During the Liquid-Phase Decomposition of Hydrogen Peroxide", Russian Journal of Physical Chemistry, (1979), pp. 1308-1309, vol. 53:9.

Shekhobalova, V.I. et al., "Relationship Between the Shape of the Kinetic Curves for the Catalytic Decomposition of Hydrogen Peroxide and the Amount of 'Soluble' Metal in the Catalyst", Russian Journal of Physical Chemistry, (1979), pp. 917-918, vol. 53:6.

Van Dam, H.E. et al., "Preparation of Platinum on Activated Carbon", Journal of Catalysis, (1991), pp. 335-349, vol. 131.

Vértes, Cs. et al., "Mossbauer Spectroscopy Studies of Sn-Pt/Al2O3 Catalysts Prepared by Controlled Surface Reactions", Applied Catalysis, (1991), pp. 149-159, vol. 68.

English Language Abstract of AU5828580.

US 6,337,298, 01/2002, Ebner et al. (withdrawn)

* cited by examiner

OXIDATION CATALYST AND ITS USE FOR CATALYZING LIQUID PHASE OXIDATION REACTIONS

This application is a United States National Stage Application based on International Application No. PCT/US2005/032862, filed Sep. 15, 2005, and claims the benefit of U.S. Provisional Application Ser. No. 60/610,103, filed Sep. 15, 2004, Ser. No. 60/619,501, filed Oct. 15, 2004, and Ser. No. 60/627,500, filed Nov. 11, 2004, the entire contents of which are incorporated herein by reference.

FIELD OF INVENTION

This invention relates to the field of heterogeneous catalysis, and more particularly to oxidation catalysts comprising carbon supports having deposited thereon a noble metal and optionally one or more promoters. The invention further relates to use of such catalysts in catalytic oxidation reactions, such as the preparation of secondary amines (e.g., N-(phosphonomethyl)glycine products) by the catalytic oxidation of tertiary amines (e.g., N-(phosphonomethyl)iminodiacetic acid substrates).

BACKGROUND OF INVENTION

N-(phosphonomethyl)glycine (known in the agricultural chemical industry as glyphosate) is described in Franz, U.S. Pat. No. 3,799,758. N-(phosphonomethyl)glycine and its salts are conveniently applied as a post-emergent herbicide in aqueous formulations. It is a highly effective and commercially important broad-spectrum herbicide useful in killing or controlling the growth of a wide variety of plants, including germinating seeds, emerging seedlings, maturing and established woody and herbaceous vegetation, and aquatic plants.

Various methods for making N-(phosphonomethyl)glycine are known in the art. Franz (U.S. Pat. No. 3,950,402) teaches that N-(phosphonomethyl)glycine may be prepared by the liquid phase oxidative cleavage of N-(phosphonomethyl)iminodiacetic acid (sometimes referred to as PMIDA) with oxygen in the presence of a catalyst comprising a noble metal deposited on the surface of an activated carbon support:

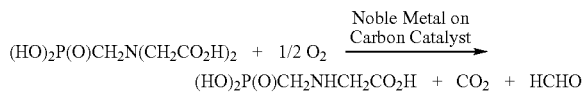

Other by-products may also form, such as formic acid, which is formed by the oxidation of the formaldehyde by-product; aminomethylphosphonic acid (AMPA) and methyl aminomethylphosphonic acid (MAMPA), which are formed by the oxidation of N-(phosphonomethyl)glycine; and iminodiacetic acid (IDA), which is formed by the de-phosphonomethylation of PMIDA. Even though the Franz method produces an acceptable yield and purity of N-(phosphonomethyl)glycine, high losses of the costly noble metal into the reaction solution (i.e., leaching) result because under the acidic conditions of the oxidation reaction, some of the noble metal is oxidized into a more soluble form and both PMIDA and N-(phosphonomethyl)glycine act as ligands that tend to further solubilize the noble metal.

In U.S. Pat. No. 3,969,398, Hershman teaches that activated carbon alone, without the presence of a noble metal, may be used to catalyze the oxidative cleavage of PMIDA to form N-(phosphonomethyl)glycine. In U.S. Pat. No. 4,624,937, Chou further teaches that the activity of the carbon catalyst taught by Hershman may be increased by removing the oxides from the surface of the carbon catalyst before using it in the oxidation reaction. See also, U.S. Pat. No. 4,696,772, which provides a separate discussion by Chou regarding increasing the activity of the carbon catalyst by removing oxides from the surface of the carbon catalyst. Although these processes obviously do not suffer from noble metal leaching, they do tend to produce greater concentrations of formaldehyde by-product when used to catalyze the oxidative cleavage of PMIDA. This formaldehyde by-product is undesirable because it reacts with N-(phosphonomethyl)glycine to produce unwanted by-products (mainly N-methyl-N-(phosphonomethyl)glycine, sometimes referred to as NMG) which reduce the N-(phosphonomethyl)glycine yield. In addition, the formaldehyde by-product itself is undesirable because of its potential toxicity. See Smith, U.S. Pat. No. 5,606,107.

It has been suggested that the formaldehyde be oxidized to carbon dioxide and water simultaneously with the oxidation of PMIDA to N-(phosphonomethyl)glycine in a single reactor using a noble metal at the surface of a carbon support to catalyze the oxidations, thus giving the following overall reaction:

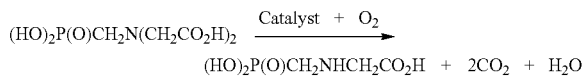

As the above teachings suggest, in such a process, carbon primarily catalyzes the oxidation of PMIDA to form N-(phosphonomethyl)glycine and formaldehyde and the noble metal primarily catalyzes the oxidation of formaldehyde to formic acid, carbon dioxide and water. Previous attempts to develop a stable noble metal catalyst for such an oxidation process, however, have not been entirely satisfactory.

Like Franz, in U.S. Pat. No. 5,179,228, Ramon et al. teach using a noble metal deposited on the surface of a carbon support. To reduce the problem of leaching (which Ramon et al. report to be as great as 30% noble metal loss per cycle), Ramon et al. teach flushing the reaction mixture with nitrogen under pressure after the oxidation reaction is completed to cause re-deposition of the noble metal onto the surface of the carbon support. According to Ramon et al., nitrogen flushing reduces the noble metal loss to less than 1%. Still, the amount of noble metal loss incurred with this method is unacceptable.

Using a different approach, in U.S. Pat. No. 4,582,650, Felthouse teaches using two catalysts: (i) an activated carbon to catalyze oxidation of PMIDA to N-(phosphonomethyl)glycine; and (ii) a co-catalyst to concurrently catalyze the oxidation of formaldehyde to carbon dioxide and water. The co-catalyst consists of an aluminosilicate support having a noble metal located within its pores. The pores are sized to exclude N-(phosphonomethyl)glycine and thereby prevent the noble metal of the co-catalyst from being poisoned by N-(phosphonomethyl)glycine. According to Felthouse, use of these two catalysts together allows for the simultaneous oxidation of PMIDA to N-(phosphonomethyl)glycine and of formaldehyde to carbon dioxide and water. This approach, however, suffers from several disadvantages: (1) it is difficult to recover the costly noble metal from the aluminosilicate support for re-use; (2) it is difficult to design and employ the two catalysts in a manner so that the oxidation reaction rates are matched; and (3) the carbon support, which has no noble metal deposited on its surface, tends to deactivate at a rate that can exceed 10% per cycle.

Ebner et al., in U.S. Pat. No. 6,417,133, describe a deeply reduced noble metal on carbon catalyst which is characterized by a CO desorption of less than 1.2 mmole/g, preferably less than 0.5 mmole/g, when a dry sample of the catalyst, after being heated at a temperature of about 500° C. for about 1 hour in a hydrogen atmosphere and before being exposed to an oxidant following the heating in the hydrogen atmosphere, is heated in a helium atmosphere from about 20° C. to about 900° C. at a rate of about 10° C. per minute, and then at about 900° C. for about 30 minutes. The catalyst is additionally or alternatively characterized as having a ratio of carbon atoms to oxygen atoms of at least about 20:1, preferably at least about 30:1, at the surface as measured by x-ray photoelectron spectroscopy after the catalyst is heated at a temperature of about 500° C. for about 1 hour in a hydrogen atmosphere and before the catalyst is exposed to an oxidant following the heating in the hydrogen atmosphere.

The catalysts of U.S. Pat. No. 6,417,133 have proven to be highly advantageous and effective catalysts for the oxidation of PMIDA to N-(phosphonomethyl)glycine and the oxidation of by-product formaldehyde and formic acid to carbon dioxide and water without excessive leaching of noble metal from the carbon support. It has further been discovered that these catalysts are effective in the operation of a continuous process for the production of N-(phosphonomethyl)glycine by oxidation of PMIDA. The advent of continuous processes for the oxidation of PMIDA has created an opportunity for further improvements in catalyst effectiveness (e.g., catalysts that accelerate the rate of oxidation of PMIDA and/or formaldehyde and/or provide improved selectivity). Since the productivity of a continuous oxidation reactor is not constrained by the turnaround cycle of a batch reactor, any improvement in reaction kinetics translates directly into an increase in the rate of product output per unit reactor volume. Furthermore, although the deeply reduced noble metal on carbon catalysts of U.S. Pat. No. 6,417,133 significantly reduce noble metal leaching in acidic oxidation reaction media, further improvements to reduce noble metal losses are nevertheless desirable to improve the economics of the process.

SUMMARY OF THE INVENTION

This invention provides catalysts and methods for preparing catalysts that are useful in various heterogeneous oxidation reactions, including the preparation of secondary amines by the catalytic oxidation of tertiary amines. The catalysts include carbon supports having deposited thereon a noble metal and, optionally, one or more promoters. The oxidation catalysts disclosed herein are particularly useful in the oxidative cleavage of PMIDA substrates such as N-(phosphonomethyl)iminodiacetic acid to form an N-(phosphonomethyl)glycine product.

Briefly, therefore, the present invention is directed to an oxidation catalyst comprising a carbon support, noble metal and a promoter, the support having metal particles at a surface thereof comprising the noble metal.

In various embodiments, the noble metal particles are characterized by the particle size distribution exhibited by metal particles of a size up to 10 nm in their largest dimension as determined, for example, using electron microscopy. In one embodiment, no more than about 25% (number basis) of the noble metal particles are less than 3 nm in their largest dimension. In another embodiment, no more than about 50% (number basis) of the noble metal particles are less than 4 nm in their largest dimension. In a further embodiment, no more than about 70% (number basis) of the noble metal particles are less than 5 nm in their largest dimension. In a still further embodiment, no more than about 90% (number basis) of the noble metal particles are less than 6 nm in their largest dimension.

In various other embodiments, no more than about 50% (number basis) of the noble metal particles are less than 4 nm in their largest dimension, no more than about 70% (number basis) of the noble metal particles are less than 5 nm in their largest dimension, and no more than about 90% (number basis) of the noble metal particles are less than 6 nm in their largest dimension.

The present invention is further directed to an oxidation catalyst comprising a carbon support having a noble metal at a surface of the carbon support, the noble metal constituting from about 2% to about 8% by weight of the catalyst. The catalyst is characterized by resistance to noble metal leaching under certain conditions. More particularly, when an aqueous mixture containing about 1% by weight of the catalyst and about 0.3% by weight glycine at a temperature of about 100° C. is agitated and contacted with a flow of molecular oxygen at a rate of about 0.8 cm$^3$ oxygen/minute/gram aqueous mixture at a pressure of about 75 psig for about 2 hours and filtered at about 95° C. to produce a first filtrate and recovered catalyst, 0.75 grams of the recovered catalyst is thereafter dried and mixed with 75 grams of a 1% by weight aqueous mixture of ammonia to form a recovered catalyst mixture, and the recovered catalyst mixture at a temperature of about 100° C. is agitated under a nitrogen atmosphere at a pressure of about 75 psig for about 1 hour and filtered at about 90° C. to produce a second filtrate, the total amount of the noble metal removed from the surface of the carbon support, as determined by inductively coupled plasma (ICP) analysis of the first filtrate and the second filtrate, is less than about 3% by weight of the noble metal initially present at the surface of the carbon support.

In another embodiment, such a catalyst's resistance to noble metal leaching is characterized by agitating an aqueous mixture containing about 1% by weight of the catalyst and about 9% by weight N-(phosphonomethyl)glycine at a temperature of about 100° C. and contacting the mixture with a flow of molecular oxygen at a rate of about 0.8 cm$^3$ oxygen/minute/gram aqueous mixture at a pressure of about 75 psig for about 2 hours and filtered at about 95° C. to produce a first filtrate and recovered catalyst, 0.75 grams of the recovered catalyst is thereafter dried and mixed with 75 grams of a 1% by weight aqueous mixture of ammonia to form a recovered catalyst mixture, and the recovered catalyst mixture at a temperature of about 100° C. is agitated under a nitrogen atmosphere at a pressure of about 75 psig for about 1 hour and filtered at about 90° C. to produce a second filtrate, the total amount of the noble metal removed from the surface of the carbon support, as determined by inductively coupled plasma (ICP) analysis of the first filtrate and the second filtrate, is less than about 3% by weight of the noble metal initially present at the surface of the carbon support.

In another embodiment, such a catalyst's resistance to noble metal leaching is characterized by agitating an aqueous mixture containing about 1% by weight of the catalyst and about 0.5% by weight aminomethylphosphonic acid at a temperature of about 100° C. and contacting the mixture with a flow of molecular oxygen at a rate of about 0.8 cm$^3$ oxygen/minute/gram aqueous mixture at a pressure of about 75 psig for about 2 hours and filtered at about 95° C. to produce a first filtrate and recovered catalyst, 0.75 grams of the recovered catalyst is thereafter dried and mixed with 75 grams of a 1% by weight aqueous mixture of ammonia to form a recovered catalyst mixture, and the recovered catalyst mixture at a temperature of about 100° C. is agitated under a nitrogen atmosphere at a pressure of about 75 psig for about 1 hour and filtered at about 90° C. to produce a second filtrate, the total amount of the noble metal removed from the surface of the carbon support, as determined by inductively coupled plasma (ICP) analysis of the first filtrate and the second filtrate, is less than about 5% by weight of the noble metal initially present at the surface of the carbon support.

The present invention is further directed to an oxidation catalyst comprising a carbon support, noble metal and a promoter, the support having metal particles comprising the noble metal at a surface thereof, wherein the catalyst is characterized as chemisorbing less than about 50 µmoles of carbon monoxide per gram of catalyst during Cycle 2 of the static carbon monoxide chemisorption analysis described in Protocol A.

The present invention is further directed to an oxidation catalyst comprising a carbon support having a noble metal, iron and cobalt at a surface of the carbon support, wherein the noble metal is selected from the group consisting of platinum, palladium, ruthenium, rhodium, iridium, silver, osmium, gold and combinations thereof and constitutes from about 2 to about 8% by weight of the catalyst. In one embodiment, iron constitutes at least about 0.05% by weight of the catalyst, cobalt constitutes at least about 0.05% by weight of the catalyst, and the weight ratio of iron to cobalt is from about 0.2:1 to about 1:1. In another embodiment, iron constitutes at least about 0.05% by weight of the catalyst, cobalt constitutes at least about 0.05% by weight of the catalyst, and the metal particles comprise noble metal atoms alloyed with iron and cobalt atoms. In a further embodiment, iron constitutes from about 0.1 to about 4% by weight of the catalyst and cobalt constitutes from about 0.1 to about 4% by weight of the catalyst.

The present invention is further directed to processes for the preparation of an oxidation catalyst. In one embodiment, the process comprises depositing a noble metal at the surface of a carbon support, and then heating the surface to a temperature of from about 850° C. to about 1200° C. in a non-oxidizing environment. The present invention is further directed to oxidation catalysts prepared in accordance with such a process.

The present invention is further directed to various processes for the preparation of N-(phosphonomethyl)glycine or a salt thereof by oxidation of an N-(phosphonomethyl)iminodiacetic acid substrate.

In one embodiment, the process for the preparation of N-(phosphonomethyl)glycine or a salt thereof comprises contacting N-(phosphonomethyl)iminodiacetic acid or a salt thereof with an oxidation catalyst as described in the above various embodiments in the presence of oxygen in a reaction medium to produce a reaction mixture comprising N-(phosphonomethyl)glycine or a salt thereof.

In a further embodiment, the process for the preparation of N-(phosphonomethyl)glycine or a salt thereof comprises contacting N-(phosphonomethyl)iminodiacetic acid or a salt thereof with an oxidation catalyst prepared by a process as described in the above embodiment in the presence of oxygen in a reaction medium to produce a reaction mixture comprising N-(phosphonomethyl)glycine or a salt thereof.

In a still further embodiment, the process for the preparation of N-(phosphonomethyl)glycine or a salt thereof comprises contacting N-(phosphonomethyl)iminodiacetic acid or a salt thereof with an oxidation catalyst comprising a carbon support having a noble metal, iron and cobalt at a surface of the carbon support in the presence of oxygen in a reaction medium to produce a reaction mixture comprising N-(phosphonomethyl)glycine or a salt thereof. The noble metal is selected from the group consisting of platinum, palladium, ruthenium, rhodium, iridium, silver, osmium, gold and combinations thereof.

Other objects and features of this invention will be in part apparent and in part pointed out hereinafter.

DETAILED DESCRIPTION OF THE PREFERRED EMBODIMENTS

Figure 1:
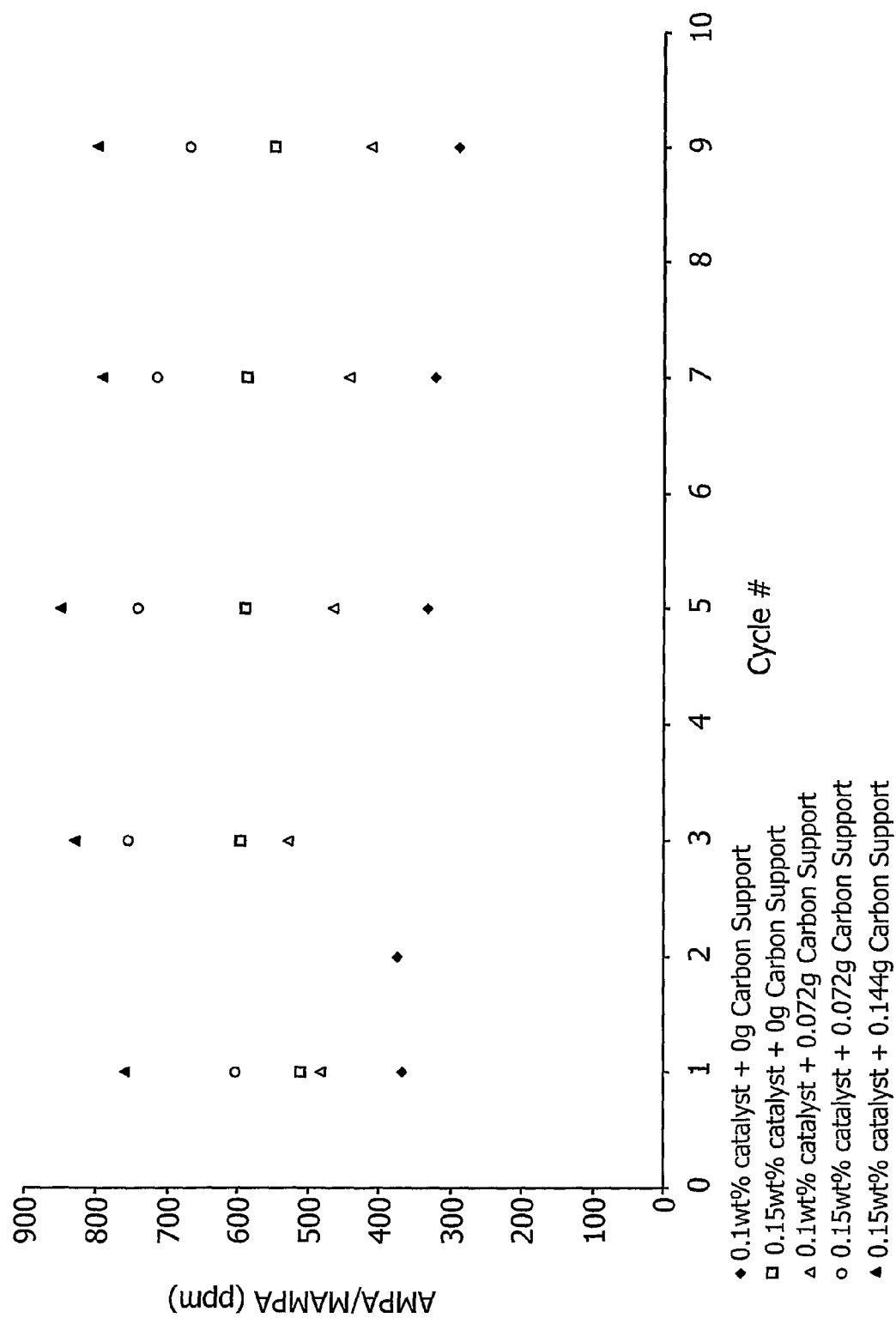
FIG. 1 shows the aminomethylphosphonic acid (AMPA) and methyl aminomethylphosphonic (MAMPA) levels during N-(phosphonomethyl)iminodiacetic acid (PMIDA) oxidation conducted using various catalysts as described in Example 3.

Described herein are oxidation catalysts comprising a noble metal deposited at a surface of a carbon support and methods for their preparation. In various embodiments, the catalyst further comprises one or more promoters also deposited at a surface of the carbon support. Catalysts of the present invention may be used to catalyze various liquid phase (e.g., in an aqueous solution or an organic solvent) oxidation reactions, in particular, the oxidation of a tertiary amine to produce a secondary amine. The catalysts of the present invention are particularly suited for use in catalyzing the liquid phase oxidation of a PMIDA substrate (e.g., N-(phosphonomethyl)iminodiacetic acid or a salt thereof) to produce an N-(phosphonomethyl)glycine product (e.g., N-(phosphonomethyl)glycine or a salt thereof).

The catalysts of the present invention exhibit various advantageous features that impart, for example, greater catalyst stability (e.g., reduced noble metal leaching) and/or improved catalyst activity and/or selectivity so as to improve productivity and efficiency of the oxidation reaction. In particular, catalysts of the present invention may provide reduced by-product formation (e.g., aminomethylphosphonic acid (AMPA), methyl aminomethylphosphonic acid (MAMPA), and/or iminodiacetic acid (IDA)) and/or provide improved oxidation of formaldehyde and formic acid by-products of the oxidation of a PMIDA substrate. In accordance with one aspect of the present invention, the particle size distribution exhibited by metal particles of the catalyst is desirably controlled so as to generally reduce the population of metal particles having a largest dimension below certain size maximums less than 10 nm to provide a catalyst exhibiting desirable performance characteristics. Various catalyst preparation techniques are described that may be employed to control the metal particle size so as to obtain the desired particle size distribution. In accordance with another aspect of the invention, the composition of the oxidation catalyst (e.g., with respect to metal loadings, noble metal/promoter combinations and the carbon support) is selected to provide a catalyst exhibiting desirable performance characteristics.

Oxidation Catalyst

The catalyst of the present invention generally comprises a carbon support having particles comprising one or more noble metal(s) at a surface thereof. Preferably, the noble metal(s) is selected from the group consisting of platinum (Pt), palladium (Pd), ruthenium (Ru), rhodium (Rh), iridium (Ir), silver (Ag), osmium (Os), gold (Au) and combinations thereof. In general, platinum and palladium are more preferred, and platinum is most preferred. Because platinum is currently the most preferred noble metal, the following discussion will be directed primarily to embodiments using platinum. It should be understood, however, that the same discussion is generally applicable to the other noble metals and combinations thereof. It also should be understood that the term "noble metal" as used herein means the noble metal in its elemental state as well as the noble metal in any of its various oxidation states.

The noble metal component of the catalyst serves various functions. For example, depending on the particular oxidation reaction, the noble metal component may be more effective than carbon at catalyzing the oxidation. In the oxidative cleavage of a PMIDA substrate, the carbon component of the catalyst is primarily responsible for catalyzing the oxidation of the substrate, while the noble metal component is primarily responsible for catalyzing the oxidation of the formaldehyde and formic acid by-products to carbon dioxide and water.

Deposition of a noble metal onto a carbon support tends to reduce the rate of deactivation of the catalyst for oxidation of a PMIDA substrate to an N-(phosphonomethyl)glycine product. To illustrate, when N-(phosphonomethyl)glycine is prepared by the liquid phase oxidative cleavage of PMIDA with oxygen in the presence of a catalyst consisting of an activated carbon support without a noble metal, the activated carbon is found to deactivate as much as 10% per cycle or more. Without being bound by any particular theory, it is believed that the deactivation of the activated carbon arises because the surface of the carbon support oxidizes under the reaction conditions. See Chou, U.S. Pat. Nos. 4,624,937 and 4,696,772. When a noble metal is present, however, the rate of deactivation of the activated carbon support is diminished. It is believed that the noble metal may react with the oxidant at a faster rate than the activated carbon surface and thus preferentially removes the oxidant from solution before extensive oxidation of the carbon surface can occur. Further, unlike many oxide species that form at activated carbon surfaces and require high temperature treatments to be reduced, oxide species that form at the surface of a noble metal typically are easily reduced by the reducing agents present in or added to the reaction mixture (e.g., the amine fragment cleaved, formaldehyde, formic acid, $H_2$, etc.), thus restoring the noble metal surface to a reduced state. In this manner, the catalyst of the invention may advantageously exhibit a long life so long as the noble metal is not lost by leaching, or excessive sintering (i.e., in the form of undesirably thick layers or clumps) by processes such as dissolution and re-deposition or noble metal agglomeration.

The concentration of noble metal on the carbon support may vary within wide limits. Generally, it is in the range of from about 0.5 to about 20% by weight ([mass of noble metal÷total mass of catalyst]×100%). If catalysts used in the oxidation of a PMIDA substrate contain less than about 0.5% by weight of the noble metal component, there tends to be less formaldehyde oxidized, and therefore a greater amount of NMG produced by reaction of formaldehyde and N-(phosphonomethyl)glycine, thereby reducing yield. On the other hand, at noble metal loadings greater than about 20% by weight, layers and/or clumps of noble metal tend to form, reducing the number of surface noble metal atoms per total amount of noble metal used, thereby undermining the economical use of the costly noble metal.

In one embodiment of the present invention, the concentration of noble metal is generally in the range of from about 2 to about 10% by weight, preferably from about 2 to about 8% by weight, more preferably from about 4 to about 8% by weight, or even more preferably from about 4 to about 6% by weight of the catalyst. It has been observed that concentrations of the noble metal within such ranges provide a catalyst that exhibits sufficient oxidation of a PMIDA substrate to N-(phosphonomethyl)glycine product and desirable oxidation of formaldehyde and formic acid by-products. Such catalysts have also been discovered to exhibit stability over the course of one or more PMIDA reaction cycles. For example, catalysts containing noble metals in such proportions typically do not exhibit an appreciable drop in activity towards oxidation of formaldehyde and/or formic acid over the course of multiple reaction cycles or during extended continuous oxidation runs.

As noted above, under certain conditions, N-(phosphonomethyl)glycine produced by the oxidative cleavage of a PMIDA substrate may be oxidized to produce AMPA and/or MAMPA by-products. This over-oxidation is currently believed to be caused, at least in part, by the carbon component of a catalyst including a noble metal deposited on a carbon support. These by-products are undesired since they directly reduce the yield of N-(phosphonomethyl)glycine product. It is currently believed that presence of a noble metal reduces the carbon exposed to the N-(phosphonomethyl)glycine product and, accordingly, over-oxidation of the product to AMPA and/or MAMPA by-products. In particular, and in accordance with another embodiment of the present invention, it has been discovered that utilizing a catalyst having relatively high metal loading may effectively reduce the total proportion of carbon on the surface of the catalyst exposed to the N-(phosphonomethyl)glycine product in the reaction mixture and, accordingly, inhibit over-oxidation of the product to AMPA and/or MAMPA by-products. Thus, in such embodiments, the concentration of noble metal is typically in the range of from about 5 to about 10% by weight, preferably from about 5 to about 8% by weight and, more preferably, from about 6 to about 8% by weight, or from about 7 to about 8% by weight of the catalyst.

In general, the carbon supports used in the present invention are well known in the art. Activated, non-graphitized carbon supports are preferred. These supports are characterized by high adsorptive capacity for gases, vapors, and colloidal solids and relatively high specific surface areas. The support suitably may be a carbon, char, or charcoal produced by means known in the art, for example, by destructive distillation of wood, peat, lignite, coal, nut shells, bones, vegetable, or other natural or synthetic carbonaceous matter, but preferably is "activated" to develop adsorptive power. Activation usually is achieved by heating to high temperatures (e.g., 800-900° C.) with steam or with carbon dioxide which brings about a porous particle structure and increased specific surface area. In some cases, hygroscopic substances, such as zinc chloride and/or phosphoric acid or sodium sulfate, are added before the destructive distillation or activation, to increase adsorptive capacity. Preferably, the carbon content of the carbon support ranges from about 10% for bone charcoal to about 98% for some wood chars and nearly 100% for activated carbons derived from organic polymers. The non-carbonaceous matter in commercially available activated carbon materials normally will vary depending on such factors as precursor origin, processing, and activation method. Many commercially available carbon supports contain small amounts of metals. Carbon supports having the fewest oxygen-containing functional groups at their surfaces are most preferred.

The form of the carbon support is not critical. In some embodiments of this invention, the support is a monolithic support. Suitable monolithic supports may have a wide variety of shapes. Such a support may be, for example, in the form of a screen or honeycomb. Such a support may also, for example, be in the form of a reactor impeller.

In various particularly preferred embodiments, the supports are in the form of particulates. Because particulate supports are especially preferred, most of the following discussion focuses on embodiments which use a particulate support. It should be recognized, however, that the present invention is not limited to the use of particulate supports.

Suitable particulate supports may have a wide variety of shapes. For example, such supports may be in the form of granules. Even more preferably, the support is in the form of a powder. These particulate supports may be used in a reactor system as free particles, or may be bound to a structure in the reactor system, such as a screen or an impeller.

Typically, a support which is in particulate form comprises a broad size distribution of particles. For powders, preferably at least about 95% of the particles are from about 2 to about 300 µm in their largest dimension, more preferably at least about 98% of the particles are from about 2 to about 200 µm in their largest dimension, and most preferably about 99% of the particles are from about 2 to about 150 µm in their largest dimension with about 95% of the particles being from about 3 to about 100 µm in their largest dimension. Particles being greater than about 200 µm in their largest dimension tend to fracture into super-fine particles (i.e., less than 2 µm in their largest dimension), which are difficult to recover.

The specific surface area of the carbon support, measured by the Brunauer-Emmett-Teller (BET) method using $N_2$, is typically from about 10 to about 3000 $m^2/g$ (surface area of carbon support per gram of carbon support), more typically from about 500 to about 2100 $m^2/g$, and still more typically from about 750 to about 2100 $m^2/g$ or from about 1000 to about 2100 $m^2/g$. In certain embodiments, the preferred specific surface area is from about 500 to about 1500 $m^2/g$, 1000 to about 1500 $m^2/g$, from about 1100 to about 1500 $m^2/g$, from about 1200 to about 1500 $m^2/g$, from about 1200 to about 1400 $m^2/g$, or about 1400 $m^2/g$.

Similar to the above-described effect of increasing metal loading on inhibiting AMPA/MAMPA production by the over-oxidation of N-(phosphonomethyl)glycine product, it has been observed that catalyst supports having surface areas at the lower end of the broad ranges set forth above may provide catalysts that reduce AMPA/MAMPA by-product formation due to a reduced proportion of carbon exposed to the N-(phosphonomethyl)glycine product. Thus, in certain embodiments, the surface area of the support is preferably from about 500 to about 1000 $m^2/g$, more preferably from about 500 to about 900 $m^2/g$, still more preferably from about 500 to about 800 $m^2/g$, from about 500 to about 700 $m^2/g$, or about 600 $m^2/g$.

The pore volume of the support may vary widely. The pore volume preferably is from about 0.1 to about 2.5 ml/g (pore volume per gram of catalyst), more preferably from about 0.2 to about 2.0 ml/g, and most preferably from about 0.4 to about 1.7 ml/g. Catalysts comprising supports with pore volumes greater than about 2.5 ml/g tend to fracture easily. On the other hand, catalysts comprising supports having pore volumes less than 0.1 ml/g tend to have small surface areas and therefore low activity.

Carbon supports for use in the present invention are commercially available from a number of sources. The following is a listing of some of the suitable activated carbons that may be used with this invention: Darco G-60 Spec and Darco X (ICI-America, Wilmington, Del.); Norit SG Extra, Norit EN4, Norit EXW, Norit A, Norit Ultra-C, Norit ACX, and Norit 4×14 mesh (Amer. Norit Co., Inc., Jacksonville, Fla.); G1-9615, VG-8408, VG-8590, NB-9377, XZ, NW, and JV (Barnebey-Cheney, Columbus, Ohio); BL Pulv., PWA Pulv., Calgon C 450, and PCB Fines (Pittsburgh Activated Carbon, Div. of Calgon Corporation, Pittsburgh, Pa.); P-100 (No. Amer. Carbon, Inc., Columbus, Ohio); Nuchar Conn., Nuchar C-1000 N, Nuchar C-190 A, Nuchar C-115 A, and Nuchar SA-30 (Westvaco Corp., Carbon Department, Covington, Va.); Code 1551 (Baker and Adamson, Division of Allied Amer. Norit Co., Inc., Jacksonville, Fla.); Grade 235, Grade 337, Grade 517, and Grade 256 (Witco Chemical Corp., Activated Carbon Div., New York, N.Y.); and Columbia SXAC (Union Carbide New York, N.Y.).

In addition to the noble metal, one or more promoters may be at the surface of the carbon support. Although the promoter typically is deposited onto the surface of the carbon support, other sources of promoter may be used (e.g., the carbon support itself may naturally contain a promoter). A promoter tends to increase catalyst selectivity, activity, and/or stability. The presence of one or more promoters, particularly when alloyed with the noble metal, tends to reduce noble metal leaching.

The promoter(s), for example, may be an additional noble metal(s) at the surface of the carbon support. For example, ruthenium and palladium have been found to act as promoters on a catalyst comprising platinum deposited at a carbon support surface. Alternatively, the promoter(s) may be a metal selected from the group consisting of tin (Sn), cadmium (Cd), magnesium (Mg), manganese (Mn), nickel (Ni), aluminum (Al), cobalt (Co), bismuth (Bi), lead (Pb), titanium (Ti), antimony (Sb), selenium (Se), iron (Fe), rhenium (Re), zinc (Zn) cerium (Ce), zirconium (Zr), tellurium (Te), germanium (Ge) and combinations thereof. Preferably, the promoter is selected from the group consisting of bismuth, iron, tin, titanium and cobalt. In a preferred embodiment, the promoter is tin. In an additional preferred embodiment, the promoter is titanium. In a particularly preferred embodiment, the promoter is iron. Catalysts comprising iron generally are most preferred because they tend to have the greatest activity and stability with respect to formaldehyde and formic acid oxidation. In accordance with the present invention, the catalyst may include iron combined with another promoter at the surface of the carbon support. For example, in one such embodiment, the catalyst comprises both iron and tin. Use of iron, tin, or both generally (1) reduces noble metal leaching for a catalyst used over several cycles, and (2) tends to increase and/or maintain the activity of the catalyst when the catalyst is used to catalyze the oxidation of PMIDA.

Optionally, the promoter is more easily oxidized than the noble metal. A promoter is "more easily oxidized" if it has a lower first ionization potential than the noble metal. First ionization potentials for the elements are widely known in the art and may be found, for example, in the CRC. Handbook of Chemistry and Physics (CRC Press, Inc., Boca Raton, Fla.).

The amount of promoter(s) at the surface of the carbon support (whether associated with the carbon surface itself, noble metal, or a combination thereof) may vary within wide limits depending on, for example, the noble metal(s) and promoter(s) used. Generally, a promoter is present in a proportion of at least about 0.05% by weight, but less than about 10% by weight ([mass of promoter÷total mass of the catalyst]×100%). Proportions of promoter less than 0.05% by weight generally do not promote the activity of the catalyst over an extended period of time. On the other hand, promoter weight percents greater than about 10% tend to decrease the activity of the catalyst. Typically, a promoter is present in a proportion of at least about 0.1% by weight, at least about 0.25% by weight, at least about 0.5% by weight, at least about 0.6% by weight or at least about 0.75% by weight. Generally, a promoter is present in a proportion of from about 0.1 to about 4% by weight, from about 0.25 to about 4% by weight, from about 0.25 to about 3% by weight, from about 0.25 to about 2.5% by weight, from about 0.5 to about 2.5% by weight, from about 0.5 to about 1.5% by weight, or from about 0.5 to about 1% by weight of the catalyst.

In the case of iron used as a promoter in the catalyst, the size of metal particles (e.g., noble metal particles including noble metal atoms associated or alloyed with iron atoms) at the surface of the carbon support tends to decrease as the concentration of iron increases. Accordingly, iron concentration in the catalyst of the present invention may impact the particle size distribution of noble metal particles at the surface of the carbon support and may be varied along with other parameters that also affect metal particle size (e.g., heat treatment temperature, inclusion of an additional component in the heat treatment atmosphere, etc. as discussed below) to achieve the desired metal particle or crystallite size distributions as disclosed below. Thus, in certain iron-promoted embodiments, iron is typically present in a proportion of less than about 1% by weight of the catalyst, preferably present in a proportion of from about 0.25 to about 0.75% by weight and, more preferably, present in a proportion of from about 0.25 to about 0.6% by weight of the catalyst.

Similar to the effect of increased noble metal loading and/or a carbon support having a relatively low surface area noted above, generally increasing the concentration of the promoter(s) tends to reduce the proportion of exposed carbon and thereby inhibit AMPA/MAMPA production by the over-oxidation of N-(phosphonomethyl)glycine product. Thus, in certain other embodiments and depending upon the desired performance characteristics, the promoter(s) is present in a relatively high concentration of from about 1 to about 4% by weight of the catalyst, from about 2 to about 3% by weight of the catalyst, or from about 2 to about 3% by weight of the catalyst.

In one particularly preferred embodiment, the catalyst comprises both iron and cobalt promoters. Use of iron and cobalt generally provides the benefits associated with use of iron (e.g., activity and stability with respect to formaldehyde and formic acid oxidation). However, as compared to the presence of iron alone as a promoter, the presence of cobalt tends to reduce formation of certain by-products during oxidation of a PMIDA substrate (e.g., IDA). Moreover, IDA formation is believed to be directly related to total promoter content of the catalyst (i.e., lower total iron and cobalt content provides lower IDA formation). Thus, in various iron/cobalt co-promoter embodiments, iron content is essentially "replaced" by cobalt to reduce formation of IDA and other by-products while nevertheless providing sufficient activity towards oxidation of formaldehyde and formic acid. For example, as compared to a platinum on carbon catalyst containing 0.5% by weight iron in the absence of cobalt, a similar catalyst containing 0.25% by weight iron and 0.25% by weight cobalt typically provides comparable activity for PMIDA, formaldehyde and formic acid oxidation, while minimizing by-product formation.

In iron/cobalt co-promoter embodiments, the amount of each promoter at the surface of the carbon support (whether associated with the carbon surface itself, noble metal, or a combination thereof) is typically at least about 0.05% by weight, at least about 0.1% by weight or at least about 0.2% by weight. Furthermore, the amount of iron at the surface of the carbon support is typically from about 0.1 to about 4% by weight of the catalyst, preferably from about 0.1 to about 2% by weight of the catalyst, more preferably from about 0.1 to about 1% by weight of the catalyst and, even more preferably, from about 0.1 to about 0.5% by weight of the catalyst. Similarly, the amount of cobalt at the surface of the carbon support is typically from about 0.1 to about 4% by weight of the catalyst, preferably from about 0.1 to about 2% by weight of the catalyst, more preferably from about 0.2 to about 1% by weight of the catalyst and, even more preferably, from about 0.2 to about 0.5% by weight of the catalyst. In such an embodiment, the weight ratio of iron to cobalt in the catalyst is generally from about 0.1:1 to about 1.5:1 and preferably from about 0.2:1 to about 1:1. For example, the catalyst may comprise about 0.1% by weight iron and about 0.4% by weight cobalt or about 0.2% by weight iron and about 0.2% by weight cobalt.

The weight ratio of noble metal to promoter is typically at least about 1 and, more typically, at least about 5. Preferably, the weight ratio of noble metal to promoter is from about 1 to about 15 and, more preferably, from about 1.35 to about 10. In various embodiments, the weight ratio of noble metal to promoter is less than about 5 and, for example, from about 1.35 to about 4 or from about 2 to about 5.

The molar ratio of noble metal(s) to promoter(s) may also vary widely, depending on, for example, the noble metal and promoter used. Generally, the molar ratio is from about 1000:1 to about 0.01:1, preferably from about 150:1 to about 0.05:1, more preferably from about 50:1 to about 0.05:1 and still more preferably from about 10:1 to about 0.05:1.

In particularly preferred embodiments of this invention, the noble metal is alloyed with at least one promoter to form alloyed metal particles. For example, noble metal particles at a surface of the carbon support comprise noble metal atoms alloyed with promoter atoms. In various other preferred embodiments, the noble metal is alloyed with two promoters (e.g., iron and cobalt). A catalyst comprising a noble metal alloyed with one or more promoters tends to have all the advantages discussed above with respect to catalysts comprising a promoter. However, catalysts comprising a noble metal alloyed with one or more promoters tend to exhibit greater resistance to metal leaching and further stability (e.g., from cycle to cycle) with respect to formaldehyde and formic acid oxidation.

The term "alloy" encompasses any metal particle comprising a noble metal and at least one promoter, irrespective of the precise manner in which the noble metal and promoter atoms are disposed within the particle (although it is generally preferable to have a portion of the noble metal atoms at the surface of the alloyed metal particle). The alloy may be, for example, any of the following:

1. An intermetallic compound. An intermetallic compound is compound comprising a noble metal and a promoter (e.g., $Pt_3Sn$).

2. A substitutional alloy. A substitutional alloy has a single, continuous phase, irrespective of the concentrations of the noble metal and promoter atoms. Typically, a substitutional alloy contains noble metal and promoter atoms which are similar in size (e.g., platinum and silver; or platinum and palladium). Substitutional alloys are also referred to as "monophasic alloys."

3. A multiphasic alloy. A multiphasic alloy is an alloy that contains at least two discrete phases. Such an alloy may contain, for example $Pt_3Sn$ in one phase, and tin dissolved in platinum in a separate phase.

4. A segregated alloy. A segregated alloy is a metal particle wherein the particle stoichiometry varies with distance from the surface of the metal particle.

5. An interstitial alloy. An interstitial alloy is a metal particle wherein the noble metal and promoter atoms are combined with non-metal atoms, such as boron, carbon, silicon, nitrogen, phosphorus, etc.

The alloyed metal particles need not have a uniform composition and the compositions may vary from particle to particle, or even within the particles themselves. In addition, the catalyst may further comprise particles consisting of the noble metal alone or the promoter alone. Nevertheless, it is preferred that the composition of metal particles be substantially uniform from particle to particle and within each particle, and that the number of noble metal atoms in intimate contact with promoter atoms be maximized. It is also preferred, although not essential, that the majority of noble metal atoms at the surface of the carbon support be alloyed with a promoter in the noble metal particles, and more preferred that substantially all of the noble metal atoms at the surface of the carbon support be alloyed with a promoter in the noble metal particles. It is further preferred, although not essential, that the alloyed metal particles be uniformly distributed at the surface of the carbon support.

As taught by Ebner et al., in U.S. Pat. No. 6,417,133, oxygen-containing functional groups (e.g., carboxylic acids, ethers, alcohols, aldehydes, lactones, ketones, esters, amine oxides, and amides) at the surface of the carbon support increase noble metal leaching and potentially increase noble metal sintering during liquid phase oxidation reactions and thus reduce the ability of the catalyst to oxidize oxidizable substrates, particularly formaldehyde during the PMIDA oxidation reaction. As used herein, an oxygen-containing functional group is "at the surface of the carbon support" if it is bound to an atom of the carbon support and is able to chemically or physically interact with compositions within the reaction mixture or with the metal atoms deposited on the carbon support.

Many of the oxygen-containing functional groups that reduce noble metal resistance to leaching and sintering and reduce the activity of the catalyst desorb from the carbon support as carbon monoxide when the catalyst is heated at a high temperature (e.g., 900° C.) in an inert atmosphere (e.g., helium or argon). Thus, measuring the amount of CO desorption from a fresh catalyst (i.e., a catalyst that has not previously been used in a liquid phase oxidation reaction) under high temperatures is one method that may be used to analyze the surface of the catalyst to predict noble metal retention and maintenance of catalyst activity. One way to measure CO desorption is by using thermogravimetric analysis with in-line mass spectroscopy ("TGA-MS"). Preferably, no more than about 1.2 mmole of carbon monoxide per gram of catalyst desorb from the catalyst of the present invention when a dry, fresh sample of the catalyst in a helium atmosphere is subjected to a temperature which is increased from about 20° C. to about 900° C. at about 10° C. per minute, and then held constant at about 900° C. for about 30 minutes. More preferably, no more than about 0.7 mmole of carbon monoxide per gram of fresh catalyst desorb under those conditions, even more preferably no more than about 0.5 mmole of carbon monoxide per gram of fresh catalyst desorb, and most preferably no more than about 0.3 mmole of carbon monoxide per gram of fresh catalyst desorb. A catalyst is considered "dry" when the catalyst has a moisture content of less than about 1% by weight. Typically, a catalyst may be dried by placing it into a $N_2$ purged vacuum of about 25 inches of Hg and a temperature of about 120° C. for about 16 hours.

Measuring the number of oxygen atoms at the surface of a fresh catalyst support is another method to analyze the catalyst to predict noble metal retention and maintenance of catalytic activity. Using, for example, x-ray photoelectron spectroscopy, a surface layer of the support which is about 50 Å in thickness is analyzed. Preferably, a ratio of carbon atoms to oxygen atoms at the surface (as measured by currently available equipment for x-ray photoelectron spectroscopy) of at least about 20:1 (carbon atoms:oxygen atoms) is suitable in the oxidation catalysts described herein. More preferably, the ratio is at least about 30:1, even more preferably at least about 40:1, even more preferably at least about 50:1, and most preferably at least about 60:1. In addition, the ratio of oxygen atoms to metal atoms at the surface (again, as measured by currently available equipment for x-ray photoelectron spectroscopy) preferably is less than about 8:1 (oxygen atoms: metal atoms). More preferably, the ratio is less than 7:1, even more preferably less than about 6:1, and most preferably less than about 5:1.

Regardless of whether the promoter is alloyed to the noble metal, it is currently believed that the promoter tends to become oxidized if the catalyst is exposed to an oxidant over a period of time. For example, an elemental tin promoter tends to oxidize to form $Sn(II)O$, and $Sn(II)O$ tends to oxidize to form $Sn(IV)O_2$. This oxidation may occur, for example, if the catalyst is exposed to air for more than about 1 hour. Although such promoter oxidation has not been observed to have a significant detrimental effect on noble metal leaching, noble metal sintering, catalyst activity, or catalyst stability, it does make analyzing the concentration of detrimental oxygen-containing functional groups at the surface of the carbon support more difficult. For example, as discussed herein, the concentration of detrimental oxygen-containing functional groups (i.e., oxygen-containing functional groups that reduce noble metal resistance to leaching and sintering, and reduce the activity of the catalyst) may be determined by measuring (using, for example, TGA-MS) the amount of CO that desorbs from the catalyst under high temperatures in an inert atmosphere. However, it is currently believed that when an oxidized promoter is present at the surface, the oxygen atoms from the oxidized promoter tend to react with carbon atoms of the support at high temperatures in an inert atmosphere to produce CO, thereby creating the illusion of more detrimental oxygen-containing functional groups at the surface of the support than actually exist. Such oxygen atoms of an oxidized promoter also can interfere with obtaining a reliable prediction of noble metal leaching, noble metal sintering, and catalyst activity from the simple measurement (via, for example, x-ray photoelectron spectroscopy) of oxygen atoms at the catalyst surface.

Thus, when the catalyst comprises at least one promoter which has been exposed to an oxidant and thereby has been oxidized (e.g., when the catalyst has been exposed to air for more than about 1 hour), it is preferred that the promoter first be substantially reduced (thereby removing the oxygen atoms of the oxidized promoter from the surface of the catalyst) before attempting to measure the amount of detrimental oxygen-containing functional groups at the surface of the carbon support. This reduction preferably is achieved by heating the catalyst to a temperature of about 500° C. for about 1 hour in an atmosphere consisting essentially of $H_2$. The measurement of detrimental oxygen-containing functional groups at the surface preferably is performed (a) after this reduction, and (b) before the surface is exposed to an oxidant following the reduction. Most preferably, the measurement is taken immediately after the reduction.

Preparation of the Oxidation Catalyst

Catalysts of the present invention may be prepared by a process generally comprising depositing a noble metal and optionally one or more promoters at the surface of the carbon support and heating the carbon support having the noble metal and promoter(s) deposited thereon in a non-oxidizing environment.

Methods used to deposit the noble metal onto the surface of the carbon support are generally known in the art, and include liquid phase methods such as reaction deposition techniques (e.g., deposition via reduction of noble metal compounds, and deposition via hydrolysis of noble metal compounds), ion exchange techniques, excess solution impregnation, and incipient wetness impregnation; vapor phase methods such as physical deposition and chemical deposition; precipitation; electrochemical deposition; and electroless deposition. See generally, Cameron, D. S., Cooper, S. J., Dodgson, I. L., Harrison, B., and Jenkins, J. W. "Carbons as Supports for Precious Metal Catalysts," *Catalysis Today*, 7, 113-137 (1990).

Preferably, the noble metal is deposited via a reactive deposition technique comprising contacting the carbon support with a solution comprising a salt of the noble metal, and then hydrolyzing the salt. An example of a suitable platinum salt which is relatively inexpensive is hexachloroplatinic acid ($H_2PtCl_6$). In one embodiment of this invention, the noble metal is deposited onto the surface of the carbon support using a solution comprising a salt of a noble metal in one of its more reduced oxidation states. For example, instead of using a salt of Pt(IV) (e.g., $H_2PtCl_6$), a salt of Pt(II) is used. In another embodiment, platinum in its elemental state (e.g., colloidal platinum) is used. Using these more reduced metal precursors leads to less oxidation of the carbon support and, therefore, less oxygen-containing functional groups being formed at the surface of the support while the noble metal is being deposited onto the surface. One example of a Pt(II) salt is $K_2PtCl_4$. Another potentially useful Pt(II) salt is diamminedinitrito platinum(II). It is currently believed that using this salt to deposit the noble metal produces a catalyst which is more resistant to leaching than a catalyst prepared using $H_2PtCl_6$ as the metal precursor. Without being bound by any particular theory, it is believed that this is due to the fact that diamminedinitrito platinum(II) generates ammonia in-situ during reduction which further promotes removal of the oxygen-containing functional groups at the surface of the carbon support. This benefit, however, should be weighed against a possible explosion danger associated with the use of diamminedinitrito platinum(II).

One or more promoters may be deposited onto the surface of the carbon support before, simultaneously with, or after deposition of the noble metal onto the surface. Methods used to deposit a promoter onto the surface of the carbon support are generally known in the art, and include the same methods used to deposit a noble metal discussed above. In one embodiment, a salt solution comprising the promoter is used to deposit the promoter. A suitable salt that may be used to deposit bismuth is $Bi(NO_3)_3.5H_2O$, a suitable salt that may be used to deposit iron is $FeCl_3.6H_2O$, a suitable salt that may be used to deposit tin is $SnCl_2.2H_2O$, and a suitable salt that may be used to deposit cobalt is $CoCl_2.6H_2O$. It should be recognized that more than one promoter may be simultaneously deposited onto the surface of the carbon support.

As noted above, a catalyst comprising a noble metal alloyed with at least one promoter is particularly preferred. There are a variety of possible preparative techniques known in the art which may be used to form a multi-metallic alloy at a carbon support surface. See, e.g., V. Ponec & G. C. Bond, *Catalysis by Metals and Alloys*, "Studies in Surface Science and Catalysis," Vol. 95 (B. Delmon. & J. T. Yates, advisory eds., Elsevier Science B.V., Amsterdam, Netherlands)

In one of the more preferred embodiments, reactive deposition is used to form metal particles containing a noble metal alloyed with a promoter. Reactive deposition may comprise, for example, reductive deposition wherein a surface of a carbon support is contacted with a solution comprising: (a) reducing agent; and (b) (i) a compound comprising the noble metal and a compound comprising the promoter, or (ii) a compound comprising both the noble metal and the promoter. A wide range of reducing agents may be used, such as sodium borohydride, formaldehyde, formic acid, sodium formate, hydrazine hydrochloride, hydroxylamine, and hypophosphorous acid. Compounds comprising a noble metal and/or a promoter include, for example:

1. Halide compounds. These include, for example, $H_2PtCl_6$, $K_2PtCl_4$, $Pt_2Br_6^{2-}$, $K_2PdCl_4$, $AuCl_4^{1-}$, $RuCl_3$, $RhCl_3 3H_2O$, $K_2RuCl_6$, $FeCl_3 6H_2O$, $(SnCl_3)^1$, $SnCl_4$, $ReCl_6$, $FeCl_2$, and $TiCl_4$.

2. Oxide and oxy chloride compounds. These include, for example, $RuO_4^{2-}$ and $M_2SnO_4$.

3. Nitrate compounds. These include, for example, $Fe(NO_3)$

4. Amine complexes. These include, for example, [Pt($NH_3$)$_4$]$Cl_2$, [Pd($NH_3$)$_4$]$Cl_2$, Pt($NH_3$)$_2$$Cl_2$, Pt($NH_3$)$_4$$PtCl_4$, Pd($NH_2CH_2CH_2NH_2$)$Cl_2$, Pt($NH_2CH_2CH_2NH_2$)$_2$$Cl_2$, and [Ru($NH_3$)$_5$Cl]$Cl_2$.

5. Phosphine complexes. These include, for example, Pt(P(CH$_3$)$_3$)$_2$Cl$_2$IrClCO(P(C$_6$H$_5$)$_3$)$_2$PtClH(PR$_3$)$_2$, wherein each R is independently a hydrocarbyl, such as methyl, ethyl, propyl, phenyl, etc.

6. Organometallic complexes. These include, for example, Pt$_2$(C$_3$H$_6$)$_2$Cl$_4$; Pd$_2$(C$_2$H$_4$)$_2$Cl$_4$; Pt(CH$_3$COO)$_2$, Pd(CH$_3$COO)$_2$; K[Sn(HCOO)$_3$]; Fe(CO)$_5$Fe$_3$(CO)$_{12}$; Fe$_4$(CO)$_{15}$; Sn$_3$(CH$_3$)$_4$ and Ti(OR)$_4$, wherein each R is independently a hydrocarbyl, such as methyl, ethyl, propyl, phenyl, etc.

7. Noble metal/promoter complexes. These include, for example, Pt$_3$(SnCl$_3$)$_2$(C$_8$H$_{12}$)$_3$ and [Pt(SnCl$_3$)$_5$]$^{3-}$.

In a particularly preferred embodiment, hydrolysis reactions are used to deposit a noble metal alloyed with a promoter. In this instance, ligands containing the noble metal and promoter are formed, and then hydrolyzed to form well-mixed, metal oxide and metal hydroxide clusters at the surface of the carbon support. Use of a drying step is particularly preferred where the surface of the support is to be subsequently reduced by heating the surface (and even more preferred where the heating is to be conducted in a non-oxidizing environment). Preferably, the support is dried to reduce the moisture content of the support to less than about 5% by weight.

After the carbon support has been impregnated with the noble metal(s) and optional promoter(s), the surface of the catalyst is heated to elevated temperatures, for example, in a heat treatment or calcining operation. Calcining may be carried out by placing the catalyst in a kiln through which a heat treatment atmosphere is passed. Various types of kilns may be used including, for example, rotary kilns, tunnel kilns, and vertical calciners.

Preferably, heat treatment following metal deposition comprises high-temperature gas-phase reduction to remove oxygen-containing functional groups from the surface of the catalyst, thereby attaining a catalyst exhibiting the carbon monoxide desorption and/or carbon atom to oxygen atom surface ratio characteristics as described previously herein and in U.S. Pat. No. 6,417,133. It should be recognized that high-temperature gas-phase reduction of the surface of the carbon support after deposition of the noble metal(s) and promoter(s) typically increases the extent to which the noble metal is alloyed with a promoter(s). Subjecting the catalyst to heat treatment also generally affects the particle size distribution of noble metal particles present at a surface of the carbon support. In particular, subjecting the catalyst to elevated temperature generally provides sintering of noble metal particles at a surface of the carbon support, thereby reducing the proportion of relatively small metal particles at a surface of the carbon support (e.g., those particles less than about 3 nm, in their largest dimension). Heat treating the catalyst also serves to reduce the surface of the catalyst (i.e., remove oxygen-containing functional groups from the surface of the catalyst).

Temperatures below 500° C. are generally unsatisfactory for providing sintering of metal particles and/or removal of oxygen-containing functional groups from the carbon support surface. Subjecting the catalyst to temperatures in excess of 1200° C. promotes graphitization of the carbon support and/or over-sintering of the metal particles. Graphitization of the carbon support and over-sintering of the metal particles tends to reduce the activity of the catalyst by reducing the surface areas of catalytically active carbon and noble metal. In addition, such a reduction in exposed surface area of catalytically active noble metal is an uneconomical use of the costly noble metal. Thus, generally, the catalyst is heated to a temperature of at least about 500° C., for example from about 500° C. to about 1200° C.

Typically, in order to attain an oxidation catalyst exhibiting the desired particle size distribution as disclosed herein, the surface of the catalyst is heated to a temperature of at least about 800° C., at least about 850° C., at least about 875° C., at least about 900° C. or at least about 950° C. Preferably, the catalyst is subjected to a heat treatment temperature of from about 850° C. to about 1200° C., for example from about 875° C. to about 1200° C., more preferably from about 900° C. to about 1200° C., even more preferably from about 900° C. to about 1000° C. and especially from about 925° C. to about 975° C. In various preferred embodiments, a heat treatment temperature of about 950° C. or about 975° C. is utilized. In particular, heating the surface of the carbon support to a temperature at least as high as these minimums and within these ranges, has an advantageous effect in promoting the formation of noble metal particles on the surface of the carbon support having a particle size distribution in which the population of smaller metal particles (e.g., those particles less than about 3 nm or less than about 4 nm, in their largest dimension) is reduced.

It is currently believed that the period at which the catalyst is held at the maximum heat treatment temperature may, to some degree, affect sintering of the metal particles and, accordingly, the particle size distribution of metal particles at the surface of the carbon support. That is, there is a general positive correlation between holding time and sintering to form larger metal particles, thereby reducing the proportion of smaller metal crystallites. Nevertheless, the duration of the heat treatment is believed to be less influential than the maximum heat treatment temperature with respect to the particle size distribution of the metal particles at the surface of the catalyst. Thus, the period that the catalyst is subjected to elevated temperatures, in particular the period at which the catalyst is held at the maximum heat treatment temperature, is not narrowly critical. In the Examples provided herein using laboratory scale equipment, the catalyst is heated to and held at the maximum heat treatment temperature for from about 10 minutes to about 120 minutes or from about 30 minutes to 60 minutes. Generally, suitable heat treatment times are reduced in larger scale production. Typically, in commercial scale apparatus (e.g., kilns), the catalyst is heated at the maximum heat treatment temperature for at least about 10 minutes, for example, at least about 30 minutes.

Preferably, the catalyst is heat treated in a non-oxidizing environment. The non-oxidizing environment may consist essentially of inert gases such as N$_2$, noble gases (e.g., argon, helium) or mixtures thereof. In certain embodiments, the non-oxidizing environment comprises a reducing environment and includes a gas-phase reducing agent such as, for example, hydrogen, carbon monoxide or combinations thereof. The non-oxidizing atmosphere in which the catalyst is heated may include other components such as ammonia, water vapor, and/or an oxygen-containing compound.

When high-temperature gas-phase reduction of the catalyst surface is desired, it is preferred for hydrogen to be present in the non-oxidizing heating environment due to the small molecular size of the hydrogen that allows better penetration into the deepest pores of the carbon support. The concentration of hydrogen may vary, although hydrogen contents of less than 1% by volume are less preferred when reduction of the catalyst surface is desired as such concentrations require a longer time to reduce the catalyst surface. Typically, hydrogen is present in the heat treatment atmosphere at a concentration of from about 1 to about 10% by volume and, more typically, from about 2 to about 5% by volume. The remainder of the gas may consist essentially of a non-oxidizing gas such as nitrogen, argon, or helium. Such non-oxidizing gases may be present in the heat treatment atmosphere at a concentration of at least about 90% by volume, from about 90 to about 99% by volume and, still more typically, from about 95 to about 98% by volume.

Contacting the catalyst with a non-oxidizing atmosphere with or without a gas-phase reducing agent such as hydrogen at elevated temperatures provides suitable catalysts. However, it has been observed that including an additional component in the heat treatment atmosphere may also provide suitable catalysts that exhibit further advantageous characteristics, particularly with respect to the size distribution of metal particles at the surface of the finished catalyst. Such additional components may be present in the heat treatment atmosphere as the surface of the carbon support is heated in the non-oxidizing environment to the heat treatment temperature and may be present in the non-oxidizing environment prior to heating the surface of the carbon support.

For example, ammonia may be introduced into the heat treatment atmosphere. The presence of ammonia is believed to modify the surface of the catalyst in a manner that increases the mobility of metal particles on the catalyst surface (e.g., by "oiling" the surface of the catalyst), thereby promoting coalescence of the smaller metal particles into larger ones. Thus, in certain embodiments, ammonia is present in the non-oxidizing heating environment at a concentration of at least about 0.01% by volume, more typically from about 0.01 to about 0.4% by volume and, still more typically, from about 0.3 to about 0.4% by volume.

In accordance with further embodiments, a gaseous oxygen-containing compound may be present in the heat treatment atmosphere. Introduction of an oxygen-containing compound to the heat treatment atmosphere is believed to promote formation of noble metal oxides (e.g., PtO, $PtO_2$) which are generally more mobile on the surface of the carbon support than noble metal in a zero oxidation state (e.g., platinum metal, $Pt^0$). The increased mobility of the noble metal oxides tends to result in greater coalescence of metal particles (i.e., sintering), thereby reducing the proportion of smaller metal particles. The presence of oxygen (e.g., by introducing water vapor) may also provide "oiling" of the catalyst surface as described above to promote coalescence of metal particles. Suitable oxygen-containing compounds are generally inert and include, for example, carbon dioxide, nitrous oxide and water vapor.

For example, carbon dioxide may be present in the heat treatment atmosphere at a concentration of from about 1 to about 5% by volume, or from about 2.75 to about 3.75% by volume. Preferably, in such embodiments, carbon dioxide is present in the heat treatment atmosphere at a concentration of at least about 2% by volume, more preferably from about 2 to about 5% by volume. One method for introducing carbon dioxide (and ammonia) into the heat treatment atmosphere involves passing a non-oxidizing heat treatment gas (e.g., $N_2$, noble gases or mixtures thereof) through an aqueous solution of ammonium carbonate (e.g., a 1M solution of ammonium carbonate). This contacting is typically carried out at temperatures of from about 20 to about 25° C.

Further in accordance with such embodiments, nitrous oxide may be present in the heat treatment atmosphere at a concentration of from about 0.5 to about 2% by volume, or from about 0.75 to about 1.25% by volume.

A water vapor-containing heat treatment atmosphere may be suitably provided by contacting a non-oxidizing gas such as $N_2$ with water. Such a heat treatment atmosphere may contain at least about 1% by volume water vapor, for example, from about 1 to about 40% by volume water vapor and may be substantially saturated with water vapor. The water vapor content of the non-oxidizing environment may be increased during heating of the surface of the carbon support. Prolonged heating of the catalyst in a water vapor-containing environment may lead to excessive cooling of the catalyst and/or produce localized temperature reductions that may undermine catalyst performance. Accordingly, in certain embodiments, the surface of the carbon support is alternately heated in a non-oxidizing environment comprising water vapor and in a substantially dry non-oxidizing environment. For example, the interval during which the surface of the carbon support is heated in a non-oxidizing environment comprising water vapor is no greater than about 1 minute and the interval during which the surface of the carbon support is heated in a substantially dry non-oxidizing environment is typically at least about 2 minutes.

In various embodiments, the carbon support is subjected to one or more pre-treatments after having been impregnated with the noble metal(s) and optional promoter(s) and prior to being subjected to heat treatment in a non-oxidizing environment. For example, the impregnated carbon support may be pre-washed by contact with a liquid phase reducing agent such as, for example, formic acid or formaldehyde or an aqueous solution of such a liquid phase reducing agent.

In accordance with certain embodiments, the catalyst may be contacted with ammonia or an aqueous mixture thereof prior to being subjected to elevated temperatures. It is currently believed that treating the catalyst in this manner provides a catalyst having a reduced number of the smaller metal crystallite particles (e.g., metal particles having a particle size in their largest dimension of less than 3 nm) at the surface of the carbon support. More particularly, it is currently believed that pre-treatment in this manner may form noble metal-ammonia complexes (e.g., $Pt-(NH_3)_x$) that are more prone to sintering into larger metal particles during subsequent heating in a non-oxidizing environment. Pre-treatment in this manner may also produce ammonium salts of oxygen-containing functional groups that promote de-oxygenation of the carbon surface. Preferably, the catalyst is contacted with ammonia or an aqueous mixture thereof having a pH of from about 7 to about 10 and, more preferably, from about 8.5 to about 9.5. The catalyst to be pre-treated may be added to water and stirred to first wet the catalyst and then ammonia or a solution comprising ammonium ions is added to the catalyst slurry to achieve the desired pH. For example, the catalyst is typically contacted with ammonia or an aqueous solution thereof for at least about 30 minutes while adding additional ammonia as necessary to maintain the pH. Because the temperature and pressure are not critical, a pre-treatment ammonia wash is preferably conducted at ambient conditions (i.e., room temperature and atmospheric pressure).

Heat treatment in accordance with the above discussion typically removes oxygen-containing functional groups from the surface of the carbon support. However, in various embodiments, the catalyst support is deoxygenated in accordance with the following description prior to deposition of the noble metal(s) and optional promoter(s). Preferably, the surface is deoxygenated using a high-temperature deoxygenation treatment. Such a treatment may be a single-step or a multi-step scheme which, in either case, results in an overall chemical reduction of oxygen-containing functional groups at the surface of the carbon support. Preferably, the carbon atom to oxygen atom ratio at the surface of the carbon support is at least about 20:1 before the noble metal is deposited onto the surface of the support.

In a two-step high-temperature deoxygenation treatment, the carbon support preferably is first treated with a gaseous or liquid phase oxidizing agent to convert oxygen-containing functionalities in relatively lower oxidation states (e.g., ketones, aldehydes, and alcohols) into functionalities in relatively higher oxidation states (e.g., carboxylic acids), which are easier to cleave from the surface of the catalyst at high temperatures. Representative liquid phase oxidizing agents include nitric acid, $H_2O_2$, chromic acid, and hypochlorite, with concentrated nitric acid comprising from about 10 to about 80 grams of $HNO_3$ per 100 grams of aqueous solution being preferred. Representative gaseous oxidants include molecular oxygen, ozone, nitrogen dioxide, and nitric acid vapors. Nitric acid vapors are the preferred oxidizing agent. With a liquid oxidant, temperatures of from about 60 to about 90° C. are appropriate, but with gaseous oxidants, it is often advantageous to use temperatures from about 50 to about 500° C. or even greater. The time during which the carbon is treated with the oxidant can vary widely from about 5 minutes to about 10 hours. Preferably, the reaction time is from about 30 minutes to about 6 hours. Experimental results indicate that carbon load, temperature, oxidant concentration, etc. in the first treatment step are not narrowly critical to achieving the desired oxidation of the carbon material and thus may be governed by convenience over a wide range. The highest possible carbon load is preferred for economic reasons.

In the second step, the oxidized carbon support is pyrolyzed (i.e., heated) at a temperature preferably in the range of from about 500 to about 1500° C., and more preferably from about 600 to about 1200° C., in a nitrogen, argon, helium, or other non-oxidizing environment (i.e., an environment consisting essentially of no molecular oxygen) to drive off the oxygen-containing functional groups from the carbon surface. At temperatures greater than 500° C., an environment may be used which comprises a small amount of ammonia (or any other chemical entity that generates $NH_3$ during pyrolysis), steam, or carbon dioxide to aid in the pyrolysis. As the temperature of the carbon support is cooled to temperatures less than 500° C., however, the presence of oxygen-containing gases such as steam or carbon dioxide may lead to the re-formation of surface oxides and thus, is preferably avoided. Accordingly, the pyrolysis is preferably conducted in a non-oxidizing atmosphere (e.g., nitrogen, argon, or helium). In one embodiment, the non-oxidizing atmosphere comprises ammonia, which tends to produce a more active catalyst in a shorter time as compared to pyrolysis in the other atmospheres. The pyrolysis may be achieved, for example, using a rotary kiln, a fluidized bed reactor, or a conventional furnace.

The carbon support generally is pyrolyzed for a period of from about 5 minutes to about 60 hours, preferably from about 10 minutes to about 6 hours. Shorter times are preferred because prolonged exposure of the carbon at elevated temperatures tends to reduce the activity of the catalyst. Without being bound to any particular theory, it is presently believed that prolonged heating at pyrolytic temperatures favors the formation of graphite, which is a less preferred form of a carbon support because it normally has significantly less surface area. As discussed above, a more active catalyst typically may be produced in a shorter time by using an atmosphere that comprises ammonia.

In a preferred embodiment of this invention, high-temperature deoxygenation is carried out in one step. This one-step treatment may consist of merely performing the pyrolysis step of the two-step high-temperature deoxygenation treatment discussed above. More preferably, however, the single-step treatment consists of pyrolyzing the carbon support as described above while simultaneously passing a gas stream comprising $N_2$, $NH_3$ (or any other chemical entity that generates $NH_3$ during pyrolysis), and steam over the carbon. Although it is not a critical feature of this invention, the flow rate of the gas stream preferably is fast enough to achieve adequate contact between the fresh gas reactants and the carbon surface, yet slow enough to prevent excess carbon weight loss and material waste. A non-reactive gas may be used as a diluent to prevent severe weight loss of the carbon.

Particle Size Distributions of Catalyst Metal Particles

In accordance with certain embodiments of the present invention, the oxidation catalyst exhibits a reduced population of smaller noble metal particles or crystallites (e.g., metal particles having a particle size in their largest dimension of less than about 3 nm) such as noble metal particles associated with or alloyed with a promoter. These less desirable smaller metal particles are more susceptible to leaching than larger particles, particularly when the catalyst is used in an environment that tends to solubilize noble metals, as in the liquid phase oxidation of a PMIDA substrate in an aqueous acidic reaction medium to form an N-(phosphonomethyl)glycine product. In addition, it is currently believed that smaller metal crystallites present at the surface of the carbon support promote IDA formation by the de-phosphonomethylation of PMIDA during PMIDA oxidation.

Catalysts exhibiting a noble metal particle size distribution in which the component of smaller metal particles or crystallites is reduced may be obtained by observing the teaching with respect to catalyst composition and/or employing one or more of the various catalyst preparation techniques described above. More particularly, by considering and managing the various parameters that impact metal particle size (e.g., inclusion of iron as a promoter in the catalyst composition, use of heat treatment temperatures following metal deposition of at least about 850° C., inclusion of certain additional components in the heat treatment atmosphere, etc.), one skilled in the art can obtain a catalyst exhibiting the desired particle size distribution.

The particle size distribution of noble metal particles at the surface of the carbon support may be determined using various techniques known to those skilled in the art, including electron microscopy as described in Example 19. Embodiments of the present invention in which the catalyst has a particle size distribution in which the component of smaller noble metal particles is reduced may be characterized with respect to the percentage of noble metal particles of a size up to 10 nm in their largest dimension having a largest dimension less than various size maximums (e.g., 3 nm, 4 nm, etc.). However, it should be recognized that although the particle size distribution is characterized with respect to particles of a size less than 10 nm, the catalyst of the present invention may contain significant numbers of larger particles (e.g., from 10 to 15 or even larger).

In various embodiments, noble metal particles of the catalyst are characterized as having a particle size distribution as determined using electron microscopy such that, with respect to noble metal particles of a size up to 10 nm in their largest dimension, no more than about 25% (number basis), no more than about 20% (number basis), or no more than about 15% (number basis) of the noble metal particles are less than 3 nm in their largest dimension. In various preferred embodiments, no more than about 12% (number basis) of the noble metal particles of a size of up to 10 nm in their largest dimension are less than 3 nm in their largest dimension. In various other preferred embodiments, no more than about 10% (number basis), no more than about 8% (number basis), or no more than about 5% (number basis) of the noble metal particles of a size up to 10 nm in their largest dimension are less than 3 nm in their largest dimension.

Additionally or alternatively, noble metal particles of the catalyst are characterized as having a particle size distribution as determined using electron microscopy such that, with respect to noble metal particles of a size up to 10 nm in their largest dimension, no more than about 50% (number basis), no more than about 45% (number basis), no more than about 40% (number basis), or no more than about 35% (number basis) of the noble metal particles are less than 4 nm in their largest dimension. In various preferred embodiments, no more than about 30% (number basis), no more than about 25% (number basis), or no more than about 20% (number basis) of the noble metal particles of a size up to 10 nm in their largest dimension are less than 4 nm in their largest dimension. In various other preferred embodiments, no more than about 10% (number basis) of the noble metal particles of a size up to 10 nm in their largest dimension are less than 4 nm in their largest dimension.

Moreover, the population of noble metal particles having a largest dimension less than 5 nm may be reduced in the oxidation catalyst of the invention. Particularly, noble metal particles are characterized as having a particle size distribution as determined using electron microscopy such that, with respect to noble metal particles of a size up 10 nm in their largest dimension, no more than about 70% (number basis) or no more than about 60% (number basis) of the noble metal particles are less than 5 nm in their largest dimension. In various preferred embodiments, no more than about 50% (number basis), no more than about 40% (number basis), or no more than about 35% (number basis) of the noble metal particles of a size up to 10 nm in their largest dimension are less than 5 nm in their largest dimension. In various other preferred embodiments, no more than about 25% (number basis), no more than about 20% (number basis), or no more than about 15% (number basis) of the noble metal particles of a size up to 10 nm in their largest dimension are less than 5 nm in their largest dimension.

Similarly, the population of noble metal particles having a largest dimension less than 6 nm may be reduced. For example, noble metal particles of the catalyst are characterized as having a particle size distribution as determined using electron microscopy such that, with respect to noble metal particles of a size up to 10 nm in their largest dimension, no more than about 90% (number basis) or no more than about 80% (number basis) of the noble metal particles are less than 6 nm in their largest dimension. In various preferred embodiments, no more than about 70% (number basis), no more than about 60% (number basis), or no more than about 55% (number basis) of the noble metal particles of a size up to 10 nm in their largest dimension are less than 6 nm in their largest dimension. In various other preferred embodiments, no more than about 40% (number basis), no more than about 30% (number basis), or no more than about 25% (number basis) of the noble metal particles of a size up to 10 nm in their largest dimension are less than 6 nm in their largest dimension.

It should be understood that the population of metal particles up to 10 nm in their largest dimension at the surface of the carbon support may satisfy one or more of the above particle size distribution criteria. Thus, in certain embodiments, no more than about 50% (number basis) of the noble metal particles of a size up to 10 nm in their largest dimension are less than 4 nm in their largest dimension, no more than about 70% (number basis) of the noble metal particles of a size up to 10 nm in their largest dimension are less than 5 nm in their largest dimension, and no more than about 90% (number basis) of the noble metal particles of a size up to 10 nm in their largest dimension are less than 6 nm in their largest dimension.

In certain other embodiments, no more than about 40% (number basis) of the noble metal particles of a size up to 10 nm in their largest dimension are less than 4 nm in their largest dimension, no more than about 60% (number basis) of the noble metal particles of a size up to 10 nm in their largest dimension are less than 5 nm in their largest dimension, and no more than about 80% (number basis) of the noble metal particles of a size up to 10 nm in their largest dimension are less than 6 nm in their largest dimension.

In still other embodiments, no more than about 30% (number basis) of the noble metal particles of a size up to 10 nm in their largest dimension are less than 4 nm in their largest dimension, no more than about 50% (number basis) of the noble metal particles of a size up to 10 nm in their largest dimension are less than 5 nm in their largest dimension, and no more than about 70% (number basis) of the noble metal particles of a size up to 10 nm in their largest dimension are less than 6 nm in their largest dimension.

Generally, at least about 40% (number basis), at least about 50% (number basis) or at least about 60% (number basis) of the noble metal particles up to 10 nm in their largest dimension are from 3 to 8 nm in their largest dimension. Typically, at least about 70% (number basis) of the noble metal particles up to 10 nm in their largest dimension are from 3 to 8 nm in their largest dimension.

Typically, at least about 10% (number basis), at least about 15% (number basis), at least about 20% (number basis), at least about 25% (number basis), at least about 35% (number basis), or at least about 40% (number basis) of the noble metal particles up to 10 nm in their largest dimension are from 3 to 6 nm in their largest dimension.

Generally, the noble metal particles up to 10 nm in their largest dimension have an average particle size of greater than about 5 nm and, typically, of greater than about 5.5 nm. For example, the noble metal particles up to 10 nm in their largest dimension have an average particle size of greater than about 6 nm, greater than about 6.5 nm, greater than about 7 nm or greater than about 7.5 nm. The average particle size of the noble metal particles up to 10 nm in their largest dimension generally ranges from about 4 to about 8 nm, more typically from about 4 to about 7 nm, preferably from about 4 to about 6 nm and, more preferably, from about 5.5 to about 6 nm.

Although as noted above, increased iron content generally tends to increase the fraction of fine metal particles, this effect may be offset by managing other aspects of the catalyst preparation process that affect metal particle size. That is, subjecting the catalyst to the calcination treatment at the relatively high temperatures described above, including an additional component(s) in the heat treatment atmosphere (e.g., an oxygen-containing compound such as water vapor), or a combination of these and other calcination stratagems disclosed herein may contribute to coalescence of metal particles and thereby compensate in whole or in part for the effect of iron promoter content to obtain a catalyst having a desired noble metal particle size distribution. Accordingly, catalysts having a relatively high iron content (e.g., above 0.5% by weight of the catalyst), but which also comprise noble metal particles satisfying the more favorable particle size distributions having decreased numbers of smaller particles can be obtained. For example, in certain embodiments wherein the catalyst comprises at least 0.6% by weight iron, no more than about 40% (number basis) of the noble metal particles up to 10 nm in their largest dimension are less than 4 nm in their largest dimension, no more than about 65% (number basis) of the noble metal particles are less than 5 nm in their largest dimension, and no more than about 85% (number basis) of the noble metal particles are less than 6 nm in their largest dimension.

As the number of smaller noble metal particles is reduced, the surface area of exposed metal on the carbon support also decreases. Accordingly, the total exposed metal surface area of catalysts of the present invention may be correlated to the above-noted benefits of decreased metal leaching and IDA production during oxidation of a PMIDA substrate associated with a reduction in the number of smaller metal particles. The total exposed metal surface area of catalysts of the present invention may be determined using static carbon monoxide chemisorption analysis, in particular, using the method described in Example 23 (Protocol A). The carbon monoxide chemisorption analysis described in Example 23 includes first and second cycles.

Catalysts of the present invention subjected to such analysis are generally characterized as chemisorbing less than about 50 μmoles of carbon monoxide per gram of catalyst and, more generally, less than about 45 μmoles of carbon monoxide per gram of catalyst. Typically, catalysts of the present invention subjected to such analysis are characterized as chemisorbing less than about 40 μmoles of carbon monoxide per gram of catalyst, preferably less than about 35 μmoles of carbon monoxide per gram of catalyst, more preferably less than about 30 μmoles of carbon monoxide per gram of catalyst, still more preferably less than about 25 μmoles of carbon monoxide per gram of catalyst and especially less than about 20 μmoles of carbon monoxide per gram of catalyst during the second cycle which is indicative of the total exposed noble metal (e.g., Pt) at the surface of the carbon support.

Exposed metal surface area ($m^2$ per gram catalyst) may be determined from the volume of CO chemisorbed using the following equation:

$$\text{Metal surface area}(m^2/g \text{ catalyst}) = 6.023 \times 10^{23} \times V/2 \times SF \times A/22{,}414, \text{ where:}$$

V=volume of CO chemisorbed ($cm^3$/g STP) (Volume of one mole of gas is 22,414 $cm^3$ STP, i.e., the volume of one μmole of CO is 0.022414 $cm^3$)

SF=stoichiometry factor (assumed to be equal to 1, i.e., one CO molecule per exposed Pt atom)

A=effective area of one exposed Pt atom ($m^2$/atom) ($8 \times 10^{-20}$ $m^2$/atom of Pt)

Thus, catalysts of the present invention generally exhibit exposed metal surface area of less than about 1.2 $m^2$/g and, more generally, exhibit exposed metal surface area of less than about 1.1 $m^2$/g. Typically, catalysts of the present invention exhibit exposed metal surface area of less than about 1.0 $m^2$/g, more typically less than about 0.85 $m^2$/g and, even more typically, less than about 0.75 $m^2$/g.

The preferred concentration of metal particles at the surface of the carbon support depends, for example, on the size of the metal particles, the specific surface area of the carbon support, and the concentration of noble metal on the catalyst. It is currently believed that, in general, the preferred concentration of metal particles is approximately from about 3 to about 1500 particles/$\mu m^2$ (i.e., number of metal particles per $\mu m^2$ of surface of carbon support), particularly where: (a) at least about 80% (number density) of the metal particles are from about 1.51 to about 7 nm in their largest dimension, (b) the carbon support has a specific surface area of from about 750 to about 2100 $m^2$/g (i.e., $m^2$ of surface of carbon support per gram of carbon support) and (c) the concentration of noble metal at the carbon support surface is from about 1 to about 10% by weight ([mass of noble metal÷total mass of catalyst]× 100%). In more preferred embodiments, narrower ranges of metal particle concentrations and noble metal concentrations are desired. In such embodiments, the concentration of metal particles is from about 15 to about 800 particles/$\mu m^2$, and the concentration of noble metal at the carbon support surface is from about 2 to about 10% by weight. In even more preferred embodiments, the concentration of metal particles is from about 15 to about 600 particles/$\mu m^2$, and the concentration of noble metal at the carbon support surface is from about 2 to about 7.5% by weight. In even more preferred embodiments, the concentration of the metal particles is from about 15 to about 400 particles/$\mu m^2$, and the concentration of noble metal at the carbon support surface is about 5% by weight. The concentration of metal particles at the surface of the carbon support may be measured using methods known in the art.

The catalyst of the present invention may be characterized by its resistance to noble metal leaching in the presence of a leaching agent and an oxidizing agent. Suitable leaching agents for testing the resistance to noble metal leaching of the catalysts of the present invention include, for example, glycine, AMPA, and N-(phosphonomethyl)glycine, as described in Example 18. Advantageously, catalysts of the present invention exhibit suitable resistance to noble metal leaching under the conditions described in Example 18.

Generally, the total platinum leached from a catalyst of the present invention tested under these conditions is less than about 20%, less than about 15%, less than about 10%, or less than about 5% by weight of the noble metal initially present. Typically, the total leaching is less than about 4% by weight of the noble metal, more typically less than about 3% by weight of the noble metal and, still more typically, less than about 2% by weight of the noble metal.

More particularly, in the case of a catalyst subjected to accelerated leaching conditions in the presence of glycine as described in Example 18, typically from about 1 to about 3% by weight of the noble metal is removed from the catalyst and, more typically, from about 1 to about 2% by weight of the noble metal is removed from the catalyst.

By way of further example, in the case of a catalyst subjected to accelerated leaching conditions in the presence of AMPA as described in Example 18, typically from about 1 to about 4% by weight of the noble metal is removed from the catalyst, more typically from about 1.5 to about 4% by weight of the noble metal is removed and, still more typically, from about 2 to about 4% by weight of the noble metal is removed from the catalyst.

By way of still further example, in the case of a catalyst subjected to accelerated leaching conditions in the presence of N-(phosphonomethyl)glycine as described in Example 18, typically from about 1 to about 3% by weight of the noble metal is removed from the catalyst.

Use of the Oxidation Catalyst

Oxidation catalysts of the present invention may be used for liquid phase oxidation reactions. Examples of such reactions include the oxidation of alcohols and polyols to form aldehydes, ketones, and acids (e.g., the oxidation of 2-propanol to form acetone, and the oxidation of glycerol to form glyceraldehyde, dihydroxyacetone, or glyceric acid); the oxidation of aldehydes to form acids (e.g., the oxidation of formaldehyde to form formic acid, and the oxidation of furfural to form 2-furan carboxylic acid); the oxidation of tertiary amines to form secondary amines (e.g., the oxidation of nitrilotriacetic acid ("NTA") to form iminodiacetic acid ("IDA")); the oxidation of secondary amines to form primary amines (e.g., the oxidation of IDA to form glycine); and the oxidation of various acids (e.g., formic acid or acetic acid) to form carbon dioxide and water.

The oxidation catalyst disclosed herein is particularly suited for catalyzing the liquid phase oxidation of a tertiary amine to a secondary amine, for example in the preparation of glyphosate and related compounds and derivatives. For example, the tertiary amine substrate may correspond to a compound of Formula I having the structure

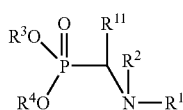

(Formula I)

wherein $R^1$ is selected from the group consisting of $R^5OC(O)CH_2$— and $R^5OCH_2CH_2$—, $R^2$ is selected from the group consisting of $R^5OC(O)CH_2$—, $R^5OCH_2CH_2$—, hydrocarbyl, substituted hydrocarbyl, acyl, —$CHR^6PO_3R^7R^8$, and —$CHR^9SO_3R^{10}$, $R^6$, $R^9$ and $R^{11}$ are selected from the group consisting of hydrogen, alkyl, halogen and —$NO_2$, and $R^3$, $R^4$, $R^5$, $R^7$, $R^8$ and are independently selected from the group consisting of hydrogen, hydrocarbyl, substituted hydrocarbyl and a metal ion. Preferably, $R^1$ comprises $R^5OC(O)CH_2$—, $R^{11}$ is hydrogen, $R^5$ is selected from hydrogen and an agronomically acceptable cation and $R^2$ is selected from the group consisting of $R^5OC(O)CH_2$—, acyl, hydrocarbyl and substituted hydrocarbyl. As noted above, the oxidation catalyst of the present invention is particularly suited for catalyzing the oxidative cleavage of a PMIDA substrate to form N-(phosphonomethyl)glycine product. In such an embodiment, the catalyst is effective for oxidation of by-product formaldehyde to formic acid, carbon dioxide and/or water.

The above-described catalysts are especially useful in liquid phase oxidation reactions at pH levels less than 7, and in particular, at pH levels less than 3. One such reaction is the oxidation of PMIDA or a salt thereof to form an N-(phosphonomethyl)glycine product in an environment having pH levels in the range of from about 1 to about 2. This reaction is often carried out in the presence of solvents which solubilize noble metals and, in addition, the reactants, intermediates, or products often solubilize noble metals.

As is recognized in the art, the liquid phase oxidation of N-(phosphonomethyl)iminodiacetic acid substrates may be carried out in a batch, semi-batch or continuous reactor system containing one or more oxidation reaction zones. The oxidation reaction zone(s) may be suitably provided by various reactor configurations, including those that have back-mixed characteristics, in the liquid phase and optionally in the gas phase as well, and those that have plug flow characteristics. Suitable reactor configurations having back-mixed characteristics include, for example, stirred tank reactors, ejector nozzle loop reactors (also known as venturi-loop reactors) and fluidized bed reactors. Suitable reactor configurations having plug flow characteristics include those having a packed or fixed catalyst bed (e.g., trickle bed reactors and packed bubble column reactors) and bubble slurry column reactors. Fluidized bed reactors may also be operated in a manner exhibiting plug flow characteristics. The configuration of the oxidation reactor system, including the number of oxidation reaction zones and the oxidation reaction conditions are not critical to the practice of the present invention. Suitable oxidation reactor systems and oxidation reaction conditions for liquid phase catalytic oxidation of an N-(phosphonomethyl)iminodiacetic acid substrate are well-known in the art and described, for example, by Ebner et al., U.S. Pat. No. 6,417,133, by Leiber et al., U.S. Pat. No. 6,586,621, and by Haupfear et al., International Publication No. WO 01/92272 and corresponding U.S. Publication No. US-2002-0068836-A1, the entire disclosures of which are incorporated herein by reference.

The description below discloses with particularity the use of catalysts described above acting as the catalyst to effect the oxidative cleavage of a PMIDA substrate to form an N-(phosphonomethyl)glycine product. It should be recognized, however, that the principles disclosed below are generally applicable to other liquid phase oxidative reactions, especially those at pH levels less than 7 and those involving solvents, reactants, intermediates, or products which solubilize noble metals.

To begin the PMIDA oxidation reaction, it is preferable to charge the reactor with the PMIDA substrate, catalyst, and a solvent in the presence of oxygen. The solvent is most preferably water, although other solvents (e.g., glacial acetic acid) are suitable as well.

The reaction may be carried out in a wide variety of batch, semi-batch, and continuous reactor systems. The configuration of the reactor is not critical. Suitable conventional reactor configurations include, for example, stirred tank reactors, fixed bed reactors, trickle bed reactors, fluidized bed reactors, bubble flow reactors, plug flow reactors, and parallel flow reactors.

When conducted in a continuous reactor system, the residence time in the reaction zone can vary widely depending on the specific catalyst and conditions employed. Typically, the residence time can vary over the range of from about 3 to about 120 minutes. Preferably, the residence time is from about 5 to about 90 minutes, and more preferably from about 5 to about 60 minutes. When conducted in a batch reactor, the reaction time typically varies over the range of from about 15 to about 120 minutes. Preferably, the reaction time is from about 20 to about 90 minutes, and more preferably from about 30 to about 60 minutes.

In a broad sense, the oxidation reaction may be practiced in accordance with the present invention at a wide range of temperatures, and at pressures ranging from sub-atmospheric to super-atmospheric. Use of mild conditions (e.g., room temperature and atmospheric pressure) have obvious commercial advantages in that less expensive equipment may be used. However, operating at higher temperatures and super-atmospheric pressures, while increasing capital requirements, tends to improve phase transfer between the liquid and gas phase and increase the PMIDA oxidation reaction rate.

Preferably, the PMIDA oxidation reaction is conducted at a temperature of from about 20 to about 180° C., more preferably from about 50 to about 140° C., and most preferably from about 80 to about 110° C. At temperatures greater than about 180° C., the raw materials tend to begin to slowly decompose.

The pressure used during the PMIDA oxidation generally depends on the temperature used. Preferably, the pressure is sufficient to prevent the reaction mixture from boiling. If an oxygen-containing gas is used as the oxygen source, the pressure also preferably is adequate to cause the oxygen to dissolve into the reaction mixture at a rate sufficient such that the PMIDA oxidation is not limited due to an inadequate oxygen supply. The pressure preferably is at least equal to atmospheric pressure. More preferably, the pressure is from about 30 to about 500 psig, and most preferably from about 30 to about 130 psig.

The catalyst concentration preferably is from about 0.1 to about 10% by weight ([mass of catalyst÷total reaction mass]× 100%). More preferably, the catalyst concentration preferably is from about 0.1 to about 5% by weight, still more preferably from about 0.2 to about 5% by weight and, most preferably, from about 0.3 to about 1.5% by weight. Concentrations greater than about 10% by weight are difficult to filter. On the other hand, concentrations less than about 0.1% by weight tend to produce unacceptably low reaction rates.

The concentration of PMIDA substrate in the feed stream is not critical. Use of a saturated solution of PMIDA substrate in water is preferred, although for ease of operation, the process is also operable at lesser or greater PMIDA substrate concentrations in the feed stream. If the catalyst is present in the reaction mixture in a finely divided form, it is preferred to use a concentration of reactants such that all reactants and the N-(phosphonomethyl)glycine product remain in solution so that the catalyst can be recovered for re-use, for example, by filtration. On the other hand, greater concentrations tend to increase reactor through-put. Alternatively, if the catalyst is present as a stationary phase through which the reaction medium and oxygen source are passed, it may be possible to use greater concentrations of reactants such that a portion of the N-(phosphonomethyl)glycine product precipitates.

It should be recognized that, relative to many commonly-practiced commercial processes, this invention allows for greater temperatures and PMIDA substrate concentrations to be used to prepare N-(phosphonomethyl)glycine while minimizing by-product formation. In the commonly practiced commercial processes using a carbon-only catalyst, it is economically beneficial to minimize the formation of the NMG by-product, which is formed by the reaction of N-(phosphonomethyl)glycine with the formaldehyde by-product. In processes based on carbon catalysts, temperatures are typically maintained between about 60 to 90° C., and PMIDA substrate concentrations are typically maintained below about 9% by weight ([mass of PMIDA substrate÷total reaction mass]×100%) to achieve cost effective yields and to minimize the generation of waste. At such temperatures, the maximum N-(phosphonomethyl)glycine solubility typically is less than 6.5%. However, with the oxidation catalyst and reaction process of this invention, formaldehyde is effectively oxidized, thereby allowing for reaction temperatures as high as 180° C. or greater with PMIDA substrate solutions and slurries of the PMIDA substrate. The use of higher temperatures and reactor concentrations permits reactor throughput to be increased, reduces the amount of water that must be removed before isolation of the solid N-(phosphonomethyl)glycine, and reduces the cost of manufacturing N-(phosphonomethyl)glycine. This invention thus provides economic benefits over many commonly-practiced commercial processes.

Normally, a PMIDA substrate concentration of up to about 50% by weight ([mass of PMIDA÷substrate total reaction mass]×100%) may be used (especially at a reaction temperature of from about 20 to about 180° C.). Preferably, a PMIDA substrate concentration of up to about 25% by weight is used (particularly at a reaction temperature of from about 60 to about 150° C.). More preferably, a PMIDA substrate concentration of from about 12 to about 18% by weight is used (particularly at a reaction temperature of from about 100 to about 130° C.). PMIDA substrate concentrations below 12% by weight may be used, but are less economical because a relatively low payload of N-(phosphonomethyl)glycine product is produced in each reactor cycle and more water must be removed and energy used per unit of N-(phosphonomethyl) glycine product produced. Relatively low reaction temperatures (i.e., temperatures less than 100° C.) often tend to be less advantageous because the solubility of the PMIDA substrate and N-(phosphonomethyl)glycine product are both relatively low at such temperatures.

The oxygen source for the PMIDA oxidation reaction may be any oxygen-containing gas or a liquid comprising dissolved oxygen. Preferably, the oxygen source is an oxygen-containing gas. As used herein, an "oxygen-containing gas" is any gaseous mixture comprising molecular oxygen which optionally may comprise one or more diluents which are non-reactive with the oxygen or with the reactant or product under the reaction conditions.

Examples of such gases are air, pure molecular oxygen, or molecular oxygen diluted with helium, argon, nitrogen, or other non-oxidizing gases. For economic reasons, the oxygen source most preferably is air, oxygen-enriched air, or pure molecular oxygen.

Oxygen may be introduced by any conventional means into the reaction medium in a manner which maintains the dissolved oxygen concentration in the reaction mixture at a desired level. If an oxygen-containing gas is used, it preferably is introduced into the reaction medium in a manner which maximizes the contact of the gas with the reaction solution. Such contact may be obtained, for example, by dispersing the gas through a diffuser such as a porous frit or by stirring, shaking, or other methods known to those skilled in the art.

The oxygen feed rate preferably is such that the PMIDA oxidation reaction rate is not limited by oxygen supply. If the dissolved oxygen concentration is too high, however, the catalyst surface tends to become detrimentally oxidized, which, in turn, tends to lead to more leaching of noble metal present in the catalyst and decreased formaldehyde activity (which, in turn, leads to more NMG being produced). Generally, it is preferred to use an oxygen feed rate such that at least about 40% of the oxygen is utilized. More preferably, the oxygen feed rate is such that at least about 60% of the oxygen is utilized. Even more preferably, the oxygen feed rate is such that at least about 80% of the oxygen is utilized. Most preferably, the rate is such that at least about 90% of the oxygen is utilized. As used herein, the percentage of oxygen utilized equals: (the total oxygen consumption rate÷oxygen feed rate)×100%. The term "total oxygen consumption rate" means the sum of: (i) the oxygen consumption rate ("$R_i$") of the oxidation reaction of the PMIDA substrate to form the N-(phosphonomethyl)glycine product and formaldehyde, (ii) the oxygen consumption rate ("$R_{ii}$") of the oxidation reaction of formaldehyde to form formic acid, and (iii) the oxygen consumption rate ("$R_{iii}$") of the oxidation reaction of formic acid to form carbon dioxide and water.

In various embodiments of this invention, oxygen is fed into the reactor as described above until the bulk of PMIDA substrate has been oxidized, and then a reduced oxygen feed rate is used. This reduced feed rate preferably is used after about 75% of the PMIDA substrate has been consumed. More preferably, the reduced feed rate is used after about 80% of the PMIDA substrate has been consumed. Where oxygen is supplied as pure oxygen or oxygen-enriched air, a reduced feed rate may be achieved by purging the reactor with (non-enriched) air, preferably at a volumetric feed rate which is no greater than the volumetric rate at which the pure molecular oxygen or oxygen-enriched air was fed before the air purge. The reduced oxygen feed rate preferably is maintained for from about 2 to about 40 minutes, more preferably from about 5 to about 20 minutes, and most preferably from about 5 to about 15 minutes. While the oxygen is being fed at the reduced rate, the temperature preferably is maintained at the same temperature or at a temperature less than the temperature at which the reaction was conducted before the air purge. Likewise, the pressure is maintained at the same or at a pressure less than the pressure at which the reaction was conducted before the air purge. Use of a reduced oxygen feed rate near the end of the PMIDA reaction allows the amount of residual formaldehyde present in the reaction solution to be reduced without producing detrimental amounts of AMPA by oxidizing the N-(phosphonomethyl)glycine product.

Reduced losses of noble metal may be observed with this invention if a sacrificial reducing agent is maintained or introduced into the reaction solution. Suitable reducing agents include formaldehyde, formic acid, and acetaldehyde. Most preferably, formic acid, formaldehyde, or mixtures thereof are used. Experiments conducted in accordance with this invention indicate that if small amounts of formic acid, formaldehyde, or a combination thereof are added to the reaction solution, the catalyst will preferentially effect the oxidation of the formic acid or formaldehyde before it effects the oxidation of the PMIDA substrate, and subsequently will be more active in effecting the oxidation of formic acid and formaldehyde during the PMIDA oxidation. Preferably from about 0.01 to about 5% by weight ([mass of formic acid, formaldehyde, or a combination thereof total reaction mass]×100%) of sacrificial reducing agent is added, more preferably from about 0.01 to about 3% by weight of sacrificial reducing agent is added, and most preferably from about 0.01 to about 1% by weight of sacrificial reducing agent is added.

In certain embodiments, unreacted formaldehyde and formic acid are recycled back into the reaction mixture for use in subsequent cycles. In this instance, an aqueous recycle stream comprising formaldehyde and/or formic acid also may be used to solubilize the PMIDA substrate in the subsequent cycles. Such a recycle stream may be generated by evaporation of water, formaldehyde, and formic acid from the oxidation reaction mixture in order to concentrate and/or crystallize product N-(phosphonomethyl)glycine. Overheads condensate containing formaldehyde and formic acid may be suitable for recycle.

Typically, the concentration of N-(phosphonomethyl)glycine in the product mixture may be as great as 40% by weight, or greater. Preferably, the N-(phosphonomethyl)glycine concentration is from about 5 to about 40%, more preferably from about 8 to about 30%, and still more preferably from about 9 to about 15%. Concentrations of formaldehyde in the product mixture are typically less than about 0.5% by weight, more preferably less than about 0.3%, and still more preferably less than about 0.15%.

Following the oxidation, the catalyst preferably is subsequently separated by filtration. The N-(phosphonomethyl)glycine product may then be isolated by precipitation, for example, by evaporation of a portion of the water and cooling.

In certain embodiments, it should be recognized that the catalyst of this invention has the ability to be reused over several cycles, depending on how oxidized its surface becomes with use. Even after the catalyst becomes heavily oxidized, it may be reused by being reactivated. To reactivate a catalyst having a heavily oxidized surface, the surface preferably is first washed to remove the organics from the surface. It then preferably is reduced in the same manner that a catalyst is reduced after the noble metal is deposited onto the surface of the support, as described above.

N-(phosphonomethyl)glycine product prepared in accordance with the present invention may be further processed in accordance with many well-known methods in the art to produce agronomically acceptable salts of N-(phosphonomethyl)glycine commonly used in herbicidal glyphosate compositions. As used herein, an "agronomically acceptable salt" is defined as a salt which contains a cation(s) that allows agriculturally and economically useful herbicidal activity of an N-(phosphonomethyl)glycine anion. Such a cation may be, for example, an alkali metal cation (e.g., a sodium or potassium ion), an ammonium ion, an isopropyl ammonium ion, a tetra-alkylammonium ion, a trialkyl sulfonium ion, a protonated primary amine, a protonated secondary amine, or a protonated tertiary amine.

In certain embodiments, the catalyst including a noble metal and optionally one or more promoters deposited on a carbon support is conditioned by using the catalyst to oxidize formaldehyde or formic acid prior to contacting the PMIDA substrate. It has been observed that such conditioning of the oxidation catalyst tends to inhibit the formation of IDA during subsequent oxidation of the PMIDA substrate.

The oxidation catalyst is typically conditioned after heat treatment following metal deposition as described above. Conditioning is suitably carried out by contacting the catalyst with an aqueous solution containing an oxidation substrate selected from the group consisting of formaldehyde, formic acid, and combinations thereof in the presence of an oxidizing agent (e.g., air or other molecular oxygen-containing gas). Typically, the aqueous solution used in the conditioning step consists essentially of water and the formaldehyde and/or formic acid oxidation substrate.

In a conditioning oxidation solution containing formaldehyde, formaldehyde is typically present at a concentration of from about 1000 parts per million (ppm) to about 10000 ppm, preferably from about 3000 to about 8000 ppm, and more preferably from about 4000 to about 6000 ppm. In certain embodiments, the conditioning oxidation solution contains formaldehyde at a concentration of about 5000 ppm. In the case of a conditioning oxidation solution containing formic acid, formic acid is typically present at a concentration of from about 1000 to about 25000 ppm, preferably from about 3000 to about 20000 ppm, from about 3000 to about 15000 ppm, and more preferably from about 8000 to about 12000 ppm. In certain embodiments, the conditioning oxidation solution contains formic acid at a concentration of about 10000 ppm.

The catalyst to be conditioned is typically present in the solution at a concentration of at least about 0.1% by weight, preferably at least about 0.15% by weight, more preferably from about 0.1 to about 2% by weight and, still more preferably, from about 0.15 to about 2% by weight.

Conditioning of the catalyst is typically carried out at temperatures above about 50° C., more typically above about 70° C. Preferably, conditioning of the catalyst is carried out at temperatures of from about 50 to about 85° C. and, more preferably, from about 75 to about 85° C. Suitable results are generally achieved by conditioning the oxidation catalyst including a noble metal and optionally one or more promoters for a period of about 20 minutes.

Conditioning of the oxidation catalyst may, for example, be conducted in the reactor system in which oxidation of a PMIDA substrate will subsequently be conducted using the conditioned catalyst. Alternatively, conditioning may take place in a vessel separate from the oxidation reactor system.

The present invention is illustrated by the following examples which are merely for the purpose of illustration and not to be regarded as limiting the scope of the invention or the manner in which it may be practiced.

Example 1

This example describes a method for preparing a catalyst precursor containing platinum and iron deposited on a carbon support.

Activated carbon support having a B.E.T. surface area of approximately 1200-1400 m$^2$/g (available from Norit Americas, Inc. (Atlanta, Ga.)) (approximately 22.5 g) was slurried in deionized water (approximately 150 ml) in a 500 ml baffled beaker for 45 minutes.

Hexachloroplatinic acid ($H_2PtCl_6$) (3.128 g) and iron chloride ($FeCl_3 \cdot 6H_2O$) (1.148 g) were mixed in deionized water (75 ml) and the platinum/iron mixture was added dropwise to the carbon support slurry over the course of 60 minutes. The pH of the resulting platinum/iron/carbon slurry was maintained at approximately 4.4 by co-addition of sodium hydroxide (NaOH) (0.5N). The platinum/iron/carbon slurry was stirred for approximately 60 minutes while its pH was maintained at approximately 4.4.

The platinum/iron/carbon slurry was heated to approximately 65° C. according the following pH/temperature profile:
Adjust pH to approximately 4.5 by addition of 0.5N sodium hydroxide and temperature to approximately 50° C. and maintain at these conditions for approximately 25 minutes.
Adjust pH to approximately 5.0 by addition of 0.5N sodium hydroxide and temperature to approximately 55° C. and maintain at these conditions for approximately 20 minutes.
Adjust pH to approximately 5.5 by addition of 0.5N sodium hydroxide and temperature to approximately 60° C. and maintain at these conditions for approximately 20 minutes.
Adjust pH to approximately 6.0 by addition of 0.5N sodium hydroxide and temperature to approximately 65° C. and maintain at these conditions for approximately 30 minutes.

Sodium borohydride ($NaBH_4$) (0.0524 g) dissolved in deionized water (75 ml) was added to the platinum/iron/carbon slurry over the course of 60 minutes during which time the temperature of the slurry was maintained at approximately 65° C. and the pH was maintained at approximately 6.0.

After addition of the sodium borohydride solution was complete, the platinum/iron/carbon slurry was filtered and the resulting wet cake was washed with approximately 400 ml of nitrogen ($N_2$) sparged deionized water at approximately 50° C. for approximately 20 minutes.

The washed cake was placed in a vacuum oven commercially available from Fisher Scientific International which was purged twice with an $N_2$-containing vacuum. The washed cake was then dried at approximately 120° C. under a vacuum and $N_2$ flow for approximately 8 hours.

This method produced a catalyst precursor containing 5% platinum and 1% iron (5% Pt/1% Fe) deposited on an activated carbon support.

Catalyst precursors containing varying contents of platinum and iron (for example, a 7.5% Pt/3% Fe precursor, described below) were prepared using this method by varying the amounts of hexachloroplatinic acid ($H_2PtCl_6$) (e.g., 4.692 g to provide 7.5% Pt) and iron chloride ($FeCl_3.6H_2O$) (e.g., 3.444 g to provide 3% Fe).

Example 2

This example describes a method for heat treatment of a catalyst precursor prepared as described in Example 1.

A 7.5% Pt/3% Fe catalyst precursor prepared as described in Example 1 (2.5 g) was placed into a tube reactor connected to a gas stream containing hydrogen (5%, by volume) in argon. The catalyst precursor was then heated from approximately 20° C. to 850° C. over the course of approximately 30 to 60 minutes and heated at approximately 850° C. for approximately 30 to 120 minutes.

Example 3

This example demonstrates the effect of the total amount of carbon support on aminomethylphosphonic acid (AMPA) and methyl aminomethylphosphonic acid (MAMPA) formation during the oxidation of N-(phosphonomethyl)iminodiacetic acid (PMIDA) to N-(phosphonomethyl)glycine ("glyphosate").

A 7.5% Pt/3% Fe catalyst, prepared as described above in Examples 1 and 2, was used to catalyze the oxidation of PMIDA to glyphosate.

One PMIDA oxidation run was conducted in a 200 ml glass reactor commercially available from Ace Glass, Inc. (Vineland, N.J.) containing a reaction mass (139.62 g) which included water (128 g), approximately 8.2% by weight PMIDA (11.48 g) and a catalyst loading of 0.1% by weight (0.14 g). The oxidation was conducted at a temperature of 100° C., a pressure of 60 psig, and an oxygen flow rate of 100 $cm^3$/minute. Another run in which the reaction mass (139.69 g) included water (128 g), approximately 8.2% by weight PMIDA (11.48 g) and a catalyst loading of 0.15% by weight (0.21 g) was conducted under the conditions set forth above. Two additional runs at catalyst loadings of 0.1% by weight (0.14 g) and 0.15% by weight (0.21 g) in which activated carbon support (0.072 g) was introduced to the reaction mass along with the catalyst were also conducted under the conditions set forth above. A final run in which the catalyst loading was 0.15% by weight (0.21 g) and activated carbon support (0.144 g) was introduced to the reaction mass was also conducted. Each run consisted of 10 60 minute reaction cycles.

The total combined amounts of AMPA/MAMPA generated during each reaction cycle of each of the runs, as determined by High Performance Liquid Chromatography (HPLC) using a system commercially available from Varian, Inc. (Palo Alto, Calif.), are shown in FIG. 1.

As shown in FIG. 1, AMPA/MAMPA levels increased with the catalyst loading. For example, from the 5th cycle on, a catalyst loading of 0.15% by weight resulted in a combined AMPA/MAMPA level approximately 300 ppm higher than that observed at a catalyst loading of 0.1% by weight. Furthermore, combined AMPA/MAMPA levels were approximately 100 ppm higher for the 0.1% and 0.15% catalyst loading runs in which activated carbon support (0.072 g) was added. At 0.15% by weight catalyst loading, the presence of additional activated carbon support (i.e., addition of 0.144 g of activated carbon support to a reaction mass containing catalyst at a loading of 0.15% by weight) further increased the AMPA/MAMPA make by approximately 100 ppm.

Example 4

This example demonstrates the effect of increased metal loading on the carbon support on combined AMPA/MAMPA formation during the oxidation of PMIDA to glyphosate.

The performance of a 7.5% Pt/3% Fe catalyst in the oxidation of PMIDA to glyphosate was compared to that of each of two 5% Pt/0.5% Fe catalysts (A and B). All three catalysts were prepared as described above in Examples 1 and 2. To prepare the 5% Pt/0.5% Fe catalysts, 0.574 g of iron chloride was present in the platinum/iron mixture.

The PMIDA oxidation was conducted as described above in Example 3. Three runs, consisting of 10 60 minute reaction cycles each, were conducted using each of the catalysts.

For the runs using the 7.5% Pt/3% Fe catalyst, catalyst loading was 0.1% by weight (0.14 g). For the runs using the 5% Pt/0.5% Fe catalysts, catalyst loading was 0.15% by weight (0.21 g). The varied catalyst loadings provided a constant platinum loading while varying the amount of carbon present (i.e., loadings of 0.15% by weight of the 5% Pt/0.5% Fe catalysts provided higher carbon loadings than 0.1% loadings of the 7.5% Pt/3% Fe catalyst).

Figure 2:
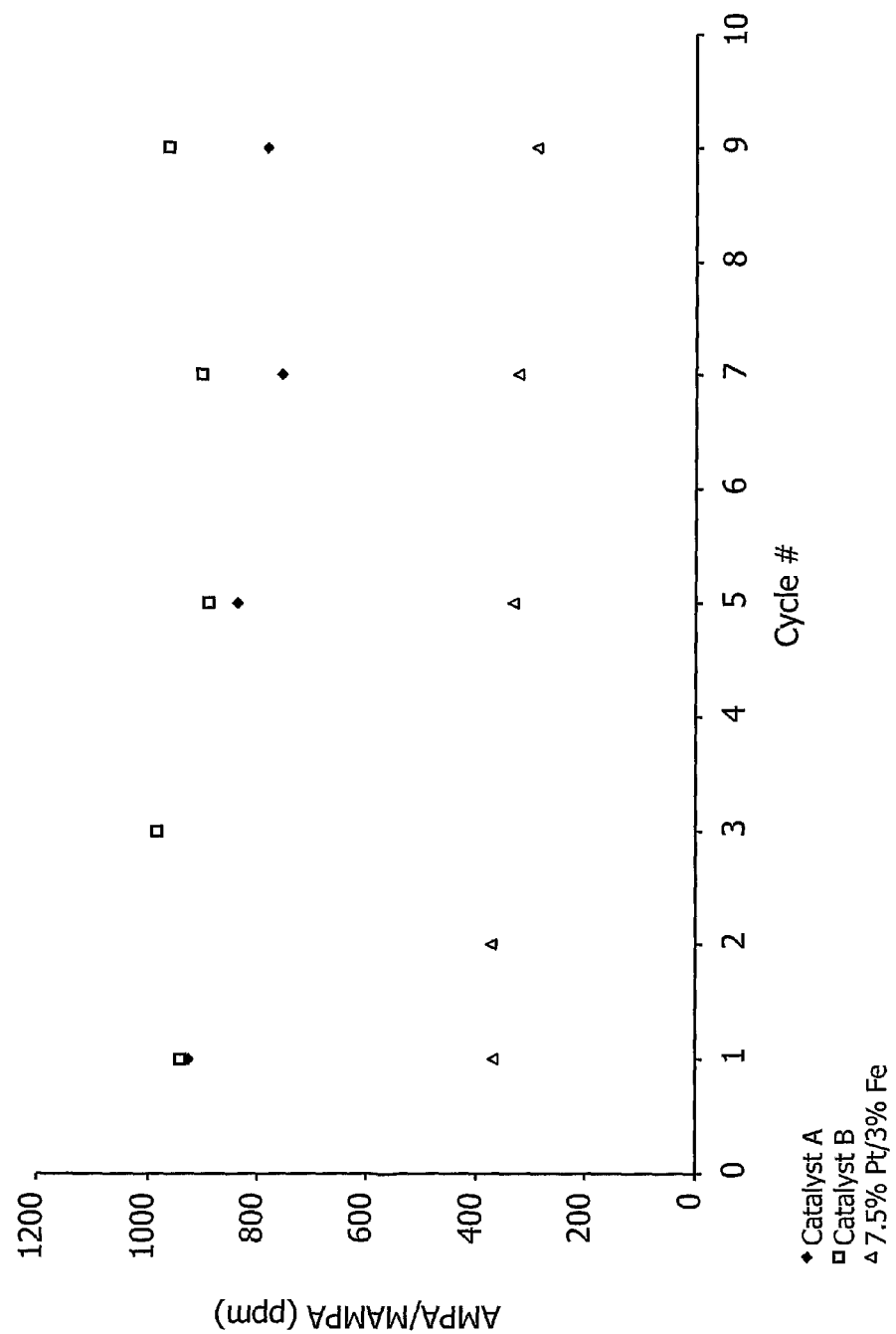
FIG. 2 shows the AMPA and MAMPA levels during PMIDA oxidation conducted using various catalysts as described in Example 4.

As shown in FIG. 2, the 7.5% Pt/3% Fe catalyst provided AMPA/MAMPA levels approximately 400 to 500 ppm lower than the 5% Pt/0.5% Fe catalysts.

Figure 3:
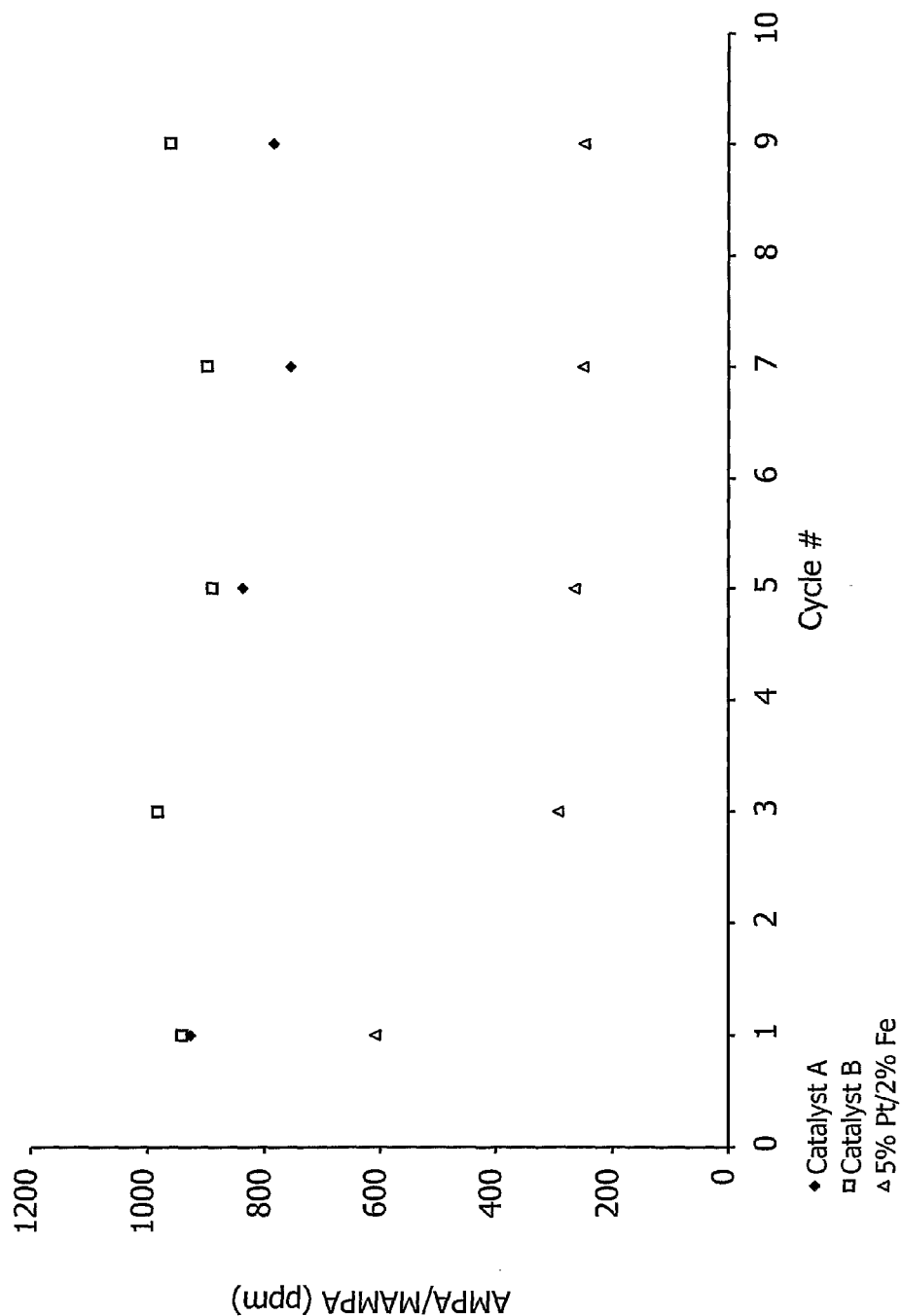
FIG. 3 shows the AMPA and MAMPA levels during PMIDA oxidation conducted using various catalysts as described in Example 4.

A 5% Pt/2% Fe catalyst on an activated carbon support having a B.E.T. surface area of approximately 600 $m^2$/g (available from Norit Americas, Inc. (Atlanta, Ga.)) was prepared as described in Examples 1 and 2. During precursor preparation, 2.296 g of iron chloride was present in the platinum/iron mixture. The catalyst was used to catalyze PMIDA oxidation under the conditions described in Example 3. A run consisting of 10 reaction cycles at a catalyst loading of 0.15% by weight was conducted. As shown in FIG. 3, from the 3rd cycle on, the combined AMPA/MAMPA levels observed using the 5% Pt/2% Fe catalyst were approximately 500 to 600 ppm less than the combined AMPA/MAMPA levels observed during the runs conducted using the 5% Pt/0.5% Fe catalysts.

These results suggest AMPA/MAMPA formation during PMIDA oxidation can be reduced by increasing the metal loading of the catalyst and/or decreasing the amount of exposed carbon present (e.g., by using a carbon support having a lower surface area).

Example 5

This example demonstrates the effect of heat treatment temperature during catalyst preparation on AMPA/MAMPA formation during PMIDA oxidation.

Two 5% Pt/1.5% Fe catalyst precursors were prepared as described in Example 1; the platinum/iron mixture contained 1.722 g of iron chloride.

Catalyst precursor (approximately 2 g) was heat treated as described in Example 2 except the catalyst precursor was heated to a maximum temperature of approximately 950° C. over the course of from approximately 30 to 60 minutes and heated at the maximum temperature for approximately 1 to 2 hours. A second 5% Pt/1.5% Fe catalyst was prepared as described in Example 2 by heating catalyst precursor (approximately 2 g) at a maximum temperature of approximately 850° C.

Each catalyst was used to catalyze the oxidation of PMIDA under the conditions described in Example 3. Two separate runs, consisting of 10 60 minute reaction cycles each, were conducted using each of the catalysts. The catalyst loading for all four runs was 0.15% by weight (0.21 g).

Figure 4:
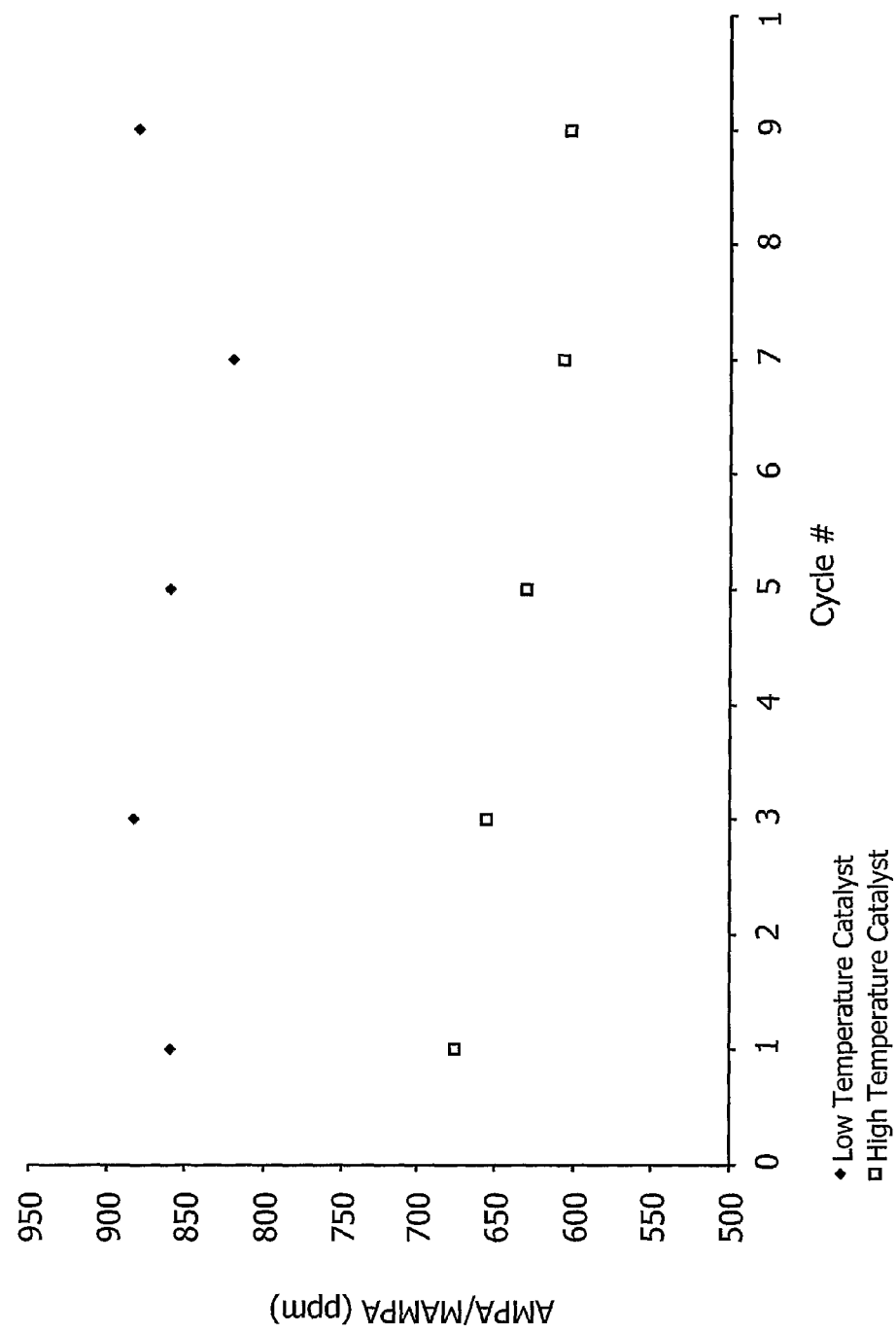
FIG. 4 shows the AMPA and MAMPA levels during PMIDA oxidation conducted using two catalysts prepared under varying conditions as described in Example 5.

As shown in FIG. 4, use of the catalyst heat treated at approximately 950° C. resulted in combined AMPA/MAMPA levels of from approximately 150 to 300 ppm lower than observed when the catalyst heat treated at 850° C. was utilized.

Example 6

This example demonstrates the effect of lowering the proportion of carbon support surface area in the reaction mixture on AMPA/MAMPA formation during PMIDA oxidation.

Figure 5:
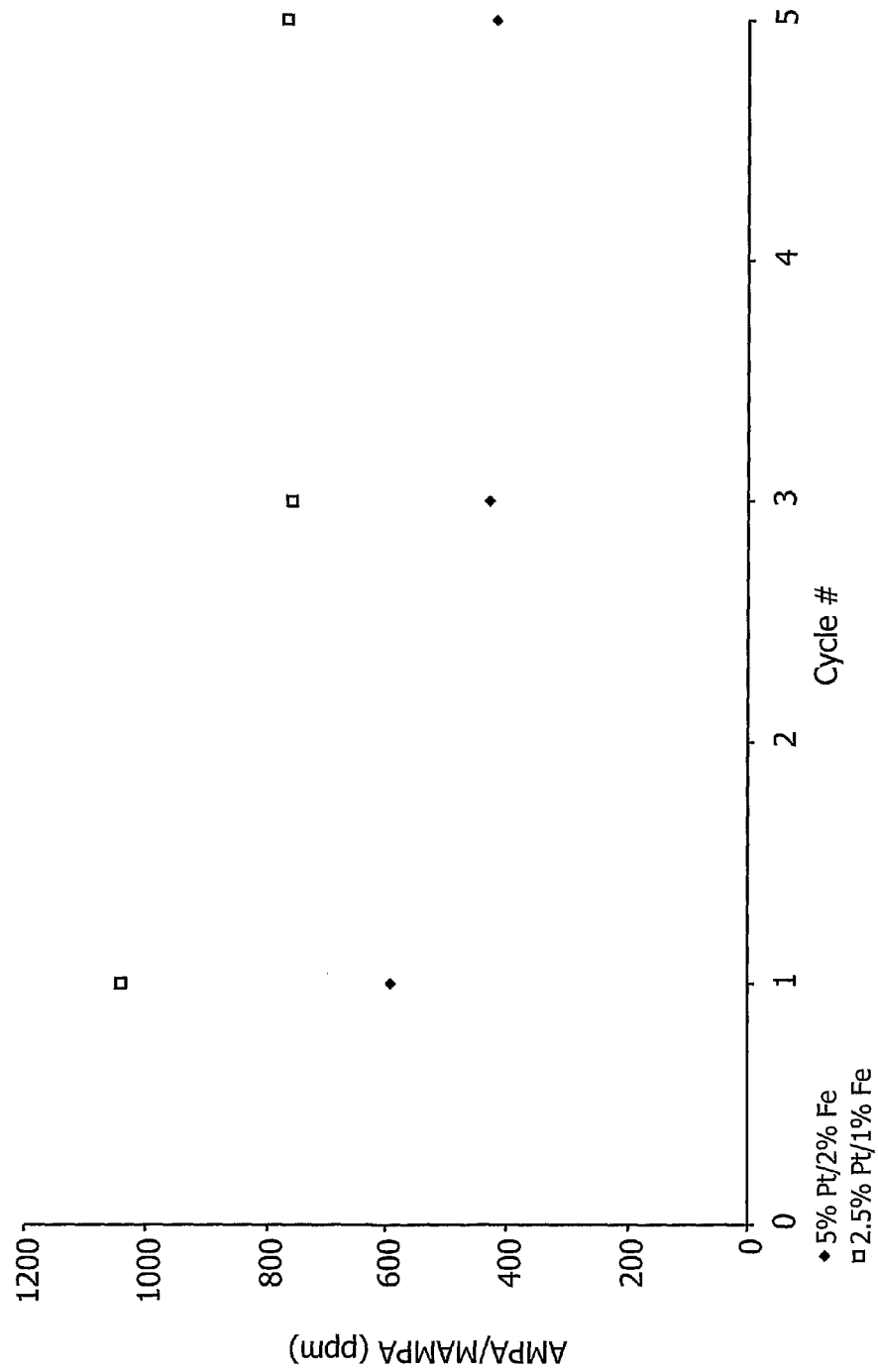
FIG. 5 shows the AMPA and MAMPA levels during PMIDA oxidation conducted using two catalysts having varying metal loadings as described in Example 6.

A 5% Pt/2% Fe catalyst was prepared as described in Example 4 using an activated carbon support having a B.E.T. surface area of approximately 600 $m^2/g$ (available from Norit Americas, Inc. (Atlanta, Ga.)). A 2.5% Pt/1% Fe catalyst was prepared as described in Examples 1 and 2 using an activated carbon support having a B.E.T. surface area of approximately 600 $m^2/g$ (available from Norit Americas, Inc. (Atlanta, Ga.)). During precursor preparation, 1.564 g of hexachloroplatinic acid and 0.574 g of iron chloride were present in the platinum/iron mixture. Each catalyst was used in the oxidation of PMIDA under the reaction conditions described in Example 3 at varied catalyst loadings. One reaction run, consisting of 10 60 minute reaction cycles, was conducted using each catalyst. The first run was conducted using the 5% Pt/2% Fe catalyst at a catalyst loading of 0.15% by weight and the second run was conducted using the 2.5% Pt/1% Fe catalyst at a loading of 0.3% by weight. The varied catalyst loadings provided a constant Pt loading while varying the carbon loading (i.e., the 0.3% by weight loading of the 2.5% Pt/1% Fe catalyst provided higher carbon loading than the 0.15% loading of the 5% Pt/2% Fe catalyst). As shown in FIG. 5, the combined AMPA/MAMPA levels produced during the run using the 5% Pt/2% Fe catalyst (i.e., lower carbon loading) were approximately 400 ppm lower than those observed during the run using the 2.5% Pt/1% Fe catalyst.

Example 7

This example demonstrates the effect of increasing metal loading on the carbon support on the stability of the catalyst (e.g., resistance to deactivation through platinum loss) during PMIDA oxidation.

A 7.5% Pt/3% Fe catalyst prepared as described in Examples 1 and 2 was used to catalyze the oxidation of PMIDA under the conditions described in Example 3. Catalyst loading was 0.15% by weight (0.216 g). A 5% Pt/0.5% Fe catalyst prepared as described in Example 4 (including heat treatment to a maximum temperature of approximately 850° C.) was also used to catalyze the oxidation of PMIDA under the conditions described in Example 3. Catalyst loading was 0.23% by weight (0.324 g). Each reaction run consisted of 10 60 minute cycles. The varied catalyst loadings provided constant platinum loadings.

Deactivation slopes, an indicator of catalyst stability, were determined by plotting the time required to generate approximately 1900 $cm^3$ of carbon dioxide during each 60 minute reaction cycle versus the cycle to provide a deactivation curve. Carbon dioxide generation was monitored throughout each reaction cycle using a Rosemont carbon dioxide detector.

As shown in Table 1, the deactivation slope of the 7.5% Pt/3% Fe catalyst was less than half that of the 5% Pt/0.5% Fe catalyst, indicating that the 7.5% Pt/3% Fe catalyst was at least twice as stable as the 5% Pt/0.5% Fe catalyst.

Initial activity, which is inversely proportional to the value of the time axis intercept of the deactivation curve, was lower for the 7.5% Pt/3% Fe catalyst (i.e., an intercept of 36.8 observed with the 7.5% Pt/3% Fe catalyst versus an intercept of 30.9 observed with the 5% Pt/0.5% Fe catalyst). However, the 7.5% Pt/3% Fe catalyst exhibited greater long term stability than the 5% Pt/0.5% Fe catalyst (i.e., provided a lower deactivation slope).

Conversion of PMIDA and oxidation of C1 byproducts of PMIDA oxidation (i.e., formaldehyde and formic acid) were determined by measuring the PMIDA and carbon dioxide content of the reaction mixture, respectively, at the end of the reaction cycle using HPLC.

Table 1 includes carbon dioxide generation results for the first and ninth cycles. After 9 reaction cycles, the 7.5% Pt/3% Fe catalyst maintained a higher activity as indicated by a higher carbon dioxide generation of approximately 100 $cm^3$ than the 5% Pt/0.5% Fe catalyst.

TABLE 1

| Catalyst | Catalyst Loading (g) | Deactivation Slope | Intercept (minutes) | 1st cycle $CO_2$ generation ($cm^3$) | 9th cycle $CO_2$ generation ($cm^3$) |
| --- | --- | --- | --- | --- | --- |
| 7.5% Pt/3% Fe | 0.216 | 0.27 | 36.8 | 2457 | 2428 |
| 5% Pt/0.5% Fe | 0.324 | 0.71 | 30.9 | 2557 | 2321 |

Table 2 shows C1 and PMIDA conversion results at 38 minutes of reaction time during the 5th and 10th reaction cycles. As shown in Table 2, on this basis, the 7.5% Pt/3% Fe catalyst provided increased oxidation of formaldehyde and formic acid by-products as compared to the 5% Pt/0.5% Fe catalyst.

TABLE 2

| Catalyst | Catalyst Loading (g) | After 38 minutes of 5th cycle | | After 38 minutes of 10th cycle | |
|---|---|---|---|---|---|
| | | % C1 Conversion | % PMIDA Conversion | % C1 Conversion | % PMIDA Conversion |
| 7.5% Pt/3% Fe | 0.216 | 51.5 | 97.6 | 52.2 | 95.5 |
| 5% Pt/0.5% Fe | 0.324 | 46 | 98.9 | 44.9 | 100 |

Example 8

This example demonstrates the effect of washing the catalyst precursor with aqueous ammonia prior to heat treatment on catalyst stability.

5% Pt/1.5% Fe catalyst precursors were prepared as described in Example 1; the platinum/iron mixture contained 1.722 g of iron chloride.

One catalyst was prepared as described in Example 2, including heat treatment to a temperature of approximately 850° C. A second 5% Pt/1.5% Fe catalyst was prepared as described in Examples 1 and 2 except the catalyst precursor was washed with an aqueous mixture of ammonia (approximately 10% ammonia, by volume) having a pH of approximately 7.5 before heat treatment. For the ammonia washing, catalyst precursor (approximately 10 g) was slurried in water (approximately 150 g) and aqueous ammonia mixture was added to the slurry to adjust its pH to approximately 7.5. The slurry was stirred for approximately 30 to 60 minutes with the aqueous ammonia added periodically to maintain the pH at approximately 7.5. The slurry was filtered and the resulting wet cake was washed with approximately 150 ml of water. The wet cake was then dried at approximately 120° C. under vacuum for approximately 8 hours. The ammonia-washed catalyst precursor was then heat-treated as described above in Example 2.

Additional 5% Pt/1.5% Fe catalysts were prepared by washing catalyst precursors with aqueous ammonia mixtures as described above having pHs of approximately of 8.5 and approximately 9.5.

Each of the four catalysts was tested in PMIDA oxidation under the reaction conditions described in Example 3. The catalyst loading in each run was 0.15% by weight (0.21 g). Each run consisted of 10 60 minute reaction cycles.

Table 3 shows the 1st cycle Pt loss (as determined by Inductively Coupled Plasma (ICP) analysis (as described in Example 18), formic acid (HCOOH) content of the reaction mixture after at the end of the 9th reaction cycle (as determined by HPLC), formaldehyde (HCHO) content of the reaction mixture after at the end of the 9th reaction cycle (as determined by HPLC), the drop in carbon dioxide generation over the course of 9 reaction cycles (i.e., the difference between $CO_2$ generation during the first reaction cycle and during the ninth cycle as determined by HPLC) and the deactivation slope determined as described above in Example 7.

TABLE 3

| Pre-Treatment | 1st Cycle Pt loss (ppm) | HCOOH concentration at end of 9th cycle (ppm) | HCHO concentration at end of 9th cycle (ppm) | $CO_2$ Drop in nine Cycles ($cm^3$) | De-activation Slope |
|---|---|---|---|---|---|
| $NH_3$ mixture, pH 7.5 | 0.08 | 4298 | 839 | 112 | 0.58 |
| $NH_3$ mixture, pH 8.5 | 0.08 | 4460 | 914 | 112 | 0.70 |
| $NH_3$ mixture, pH 9.5 | 0.08 | 4574 | 1008 | 67 | 0.42 |
| no wash | 0.11 | 4412 | 1051 | 196 | 0.78 |

As shown in Table 3, during the first cycle, the catalysts prepared including washing the precursor with aqueous ammonia exhibited approximately 27% less platinum loss than the catalyst prepared from the unwashed precursor. As indicated by the lower reduction in carbon dioxide generation over the course of 9 cycles, catalysts prepared from ammonia-washed precursors also exhibited higher stability than the catalyst prepared from the un-washed precursor. The catalyst prepared from a precursor washed in aqueous ammonia at a pH of 9.5 exhibited the highest stability overall as indicated by its having the lowest deactivation slope.

The iminodiacetic acid (IDA) content (% by weight) of the product mixture from the first cycle of the reaction runs conducted using each of the four catalyst samples was determined by HPLC. The results are shown in Table 4.

TABLE 4

| Catalyst | pH of $NH_3$ Treatment | IDA (% by weight, 1st Cycle) |
|---|---|---|
| 5% Pt/1.5% Fe | no treatment | 0.22 |
| 5% Pt/1.5% Fe | 7.5 | 0.23 |
| 5% Pt/1.5% Fe | 8.5 | 0.19 |
| 5% Pt/1.5% Fe | 9.5 | 0.19 |

As shown in Table 4, use of catalysts prepared from precursors pre-washed with aqueous ammonia at pHs of approximately 8.5 and 9.5 resulted in less IDA generation in the first cycle than use of an un-washed precursor or a precursor washed with an aqueous ammonia mixture having a pH of 7.5.

Example 9

This example demonstrates the effect of the water vapor content of the heat treatment atmosphere on catalyst stability during PMIDA oxidation.

A 5% Pt/1.5% Fe catalyst precursor was prepared as described in Example 5. The catalyst precursor was subjected to heat treatment generally as described above in Example 2; the catalyst precursor (1 g) was placed into the tube reactor described above which was connected to a hydrogen (5%, by volume) in helium gas stream. The catalyst precursor was heated from approximately 20° C. to 900° C. over the course of approximately 83 minutes and heated at approximately 900° C. for approximately 30 minutes.

Additional 5% Pt/1.5% Fe catalysts were prepared by heat treatment of catalyst precursors prepared as described in Example 5 at varying heat treatment atmosphere moisture levels. For one sample, the heat treatment gas stream was saturated with water vapor by passing the gas stream through a water trap at room temperature. The saturated gas stream was passed through the catalyst for 120 seconds. A dry heat treatment gas stream was then contacted with the catalyst for 60 seconds. The alternating periods of contacting the catalyst with a saturated gas stream followed by contacting the catalyst with a dry gas atmosphere were continued throughout the approximately 113 minutes of heat treatment. Three additional catalysts were prepared by contacting the catalyst precursor with the moisture-doped heat treatment gas for intermittent periods of 60 seconds, 20 seconds, and 6 seconds, respectively, followed by passage of a dry gas stream for 60 seconds through the catalyst after each period of contact with the moisture-doped atmosphere during the approximately 113 minutes of heat treatment.

The five catalyst samples (control sample and 4 catalysts prepared using a moisture-doped heat treatment atmosphere on various intervals during heat treatment) were used to catalyze PMIDA oxidation under the conditions described in Example 3 at a catalyst loading of 0.15% by weight (0.21 g). Each run consisted of 10 60 minute reaction cycles.

Table 5 shows the slope of the deactivation curve, intercept of the deactivation curve, $CO_2$ generation during the ninth reaction cycle, and the carbon dioxide drop over the course of the 9 reaction cycles determined as described in Example 7 during PMIDA oxidation carried out using each of the catalysts.

TABLE 5

| Catalyst | Repetitive doping time | Deactivation slope | Intercept (minutes) | $CO_2$ generation at 9th cycle ($cm^3$) | $CO_2$ drop in nine cycles ($cm^3$) |
|---|---|---|---|---|---|
| 1 | 120 sec. | 0.90 | 35.5 | 2257 | 228 |
| 2 | 60 sec. | 0.68 | 37.2 | 2255 | 179 |
| 3 | 20 sec. | 0.65 | 37.9 | 2207 | 186 |
| 4 | 6 sec. | 0.61 | 36.7 | 2265 | 161 |
| 5 | 0 sec. (control) | 0.89 | 36.7 | 2188 | 238 |

As indicated by lower deactivation slopes and smaller drops in $CO_2$ generation over the course of the nine reaction cycles, the catalysts prepared using a moisture-doped heat treatment gas for intervals of 6, 20 and 60 seconds exhibited increased stability as compared to the catalysts prepared without moisture doping and with moisture doping for 120 second intervals.

Example 10

This example demonstrates the effect of injecting carbon dioxide into the heat treatment atmosphere on catalyst stability.

A 5% Pt/1.5% Fe catalyst precursor was prepared as described in Example 5. The catalyst precursor (1 g) was placed into the tube reactor described in Example 2 to which a hydrogen (5%, by volume) in helium gas stream was introduced at a flow rate of approximately 60 $cm^3$/min. The catalyst precursor was heated from approximately 20° C. to approximately 900° C. over the course of 88 minutes and at approximately 900° C. for approximately 25 minutes. Carbon dioxide was introduced to the reactor at a rate of approximately 120 $cm^3$/hour during heating of the catalyst precursor to the maximum temperature and heating at the maximum holding temperature of 900° C.

A second 5% Pt/1.5% Fe catalyst precursor was prepared as described in Example 5. The catalyst precursor (1 g) was placed into the tube reactor described above which was connected to a hydrogen (5%, by volume) in helium gas stream at a flow rate of 60 $cm^3$/min. The catalyst precursor was heated from approximately 20° C. to approximately 900° C. over the course of 88 minutes and heated at approximately 900° C. for approximately 25 minutes. Carbon dioxide (approximately 50 $cm^3$ over the course of 25 minutes) was introduced to the heat treatment atmosphere while the catalyst precursor was heated at the maximum holding temperature of approximately 900° C.

A third 5% Pt/1.5% Fe catalyst precursor was prepared as described in Example 5 and the catalyst precursor (1 g) was heated from approximately 20° C. to approximately 900° C. over the course of 88 minutes and heated at approximately 900° C. for approximately 25 minutes, but without addition of carbon dioxide to the heat treatment atmosphere.

The three catalyst samples (continuous carbon dioxide introduction, carbon dioxide introduced during heating at the maximum temperature, and no carbon dioxide introduced) were used to catalyze the oxidation of PMIDA under the conditions described above in Example 3. Runs consisting of five 60 minute reaction cycles were conducted using each of the three catalysts.

Table 6 shows the slope of the deactivation curve, time axis intercept of the deactivation curve, $CO_2$ generation during the fourth reaction cycle for the control sample and $CO_2$ generation during the fifth reaction cycle for the two samples prepared using a carbon dioxide-doped heat treatment atmosphere, and the drop in carbon dioxide generation between the 1st and 4th reaction cycles for the control sample and between the 1st and 5th reaction cycles for the two samples prepared using a carbon dioxide-doped heat treatment atmosphere.

TABLE 6

| Catalyst | Gas Dopant | Injection | Deactivation slope | Intercept (minutes) | $CO_2$ generation at 4th or 5th cycle ($cm^3$) | Drop in $CO_2$ generation ($cm^3$) |
|---|---|---|---|---|---|---|
| 1 | None | none | 1.53 | 32.8 | 2348 (4th) | 135 |
| 2 | $CO_2$ | continuous from room temperature | 0.85 | 35.2 | 2358 (5th) | 104 |
| 3 | $CO_2$ | at maximum temperature | 1.64 | 32.6 | 2305 (5th) | 161 |

As indicated by a decrease in the deactivation slope (1.53 vs. 0.85), the catalyst heat-treated in a continuously $CO_2$- doped atmosphere exhibited improved catalyst stability as compared to the control sample.

Example 11

This example describes the effect of heat treatment residence time during catalyst preparation on IDA yield during PMIDA oxidation.

Two 5% Pt catalyst precursors were prepared generally as described in Example 1 with a mixture of $H_2PtCl_6$ (3.128 g) in deionized water (75 ml) being contacted with the carbon support slurry. The two catalyst precursors were subjected to heat treatment generally as described in Example 2 with the precursors heated to a temperature of approximately 875° C. over the course of approximately 30 to 60 minutes and heated at approximately 875° C. for 1 hour and 2 hours, respectively.

Each catalyst was used to catalyze the oxidation of PMIDA under the conditions described in Example 3. The catalyst loading of each catalyst was 0.15% by weight (0.21 g).

The amount of iminodiacetic acid (IDA) in the reaction product mixture (% by weight) was determined by HPLC after a reaction time of 60 minutes using each catalyst. The results are shown in Table 7.

TABLE 7

| Catalyst | Residence Time | IDA (% by weight) 60 minutes reaction time |
| --- | --- | --- |
| 5% Pt/C | 1 hour | 0.031 |
| 5% Pt/C | 2 hours | 0.025 |

As shown in Table 7, the product mixture of the reaction conducted using the catalyst prepared by heat treatment which included a holding time at the maximum temperature of approximately 875° C. for approximately 2 hours contained approximately 20% less IDA than the product mixture of the reaction conducted using the catalyst prepared by heat treatment which included a holding time at the maximum temperature of approximately 1 hour.

Example 12

This example demonstrates the effect of catalyst heat treatment temperature on formation of IDA during PMIDA oxidation.

A 5% Pt catalyst precursor prepared as described in Example 11 was heated in the presence of a hydrogen (10%, by volume) in argon atmosphere in the tube reactor described in Example 2 from approximately 20° C. to approximately 830° C. over the course of 2 hours. The catalyst precursor was then heated at 830° C. for approximately 1 hour.

A second 5% Pt catalyst precursor prepared as described in Example 11 was heated in the presence of a hydrogen (10%, by volume) in argon atmosphere in the tube reactor described above from approximately 20° C. to approximately 875° C. over the course of 2 hours. The catalyst precursor was then heated at 875° C. for approximately 1 hour.

Each of the catalysts and a 5% Pt catalyst precursor prepared as described in Example 11 (i.e., no heat treatment) were used to catalyze the oxidation of PMIDA under the conditions described in Example 3. For each oxidation, the catalyst or catalyst precursor loading was 0.15% by weight (0.21 g).

The amount of iminodiacetic acid (IDA) in the reaction product (% by weight) was determined by HPLC after a reaction time of 60 minutes using each catalyst. The results are shown in Table 8.

TABLE 8

| Catalyst | Heat Treatment Temperature | IDA (% by weight) at 1st cycle |
| --- | --- | --- |
| 5% Pt/C | N/A | 0.047 |
| 5% Pt/C | 830° C. | 0.038 |
| 5% Pt/C | 875° C. | 0.031 |

As shown in Table 8, less IDA was generated during the oxidations conducted using the two heat-treated catalysts than during the oxidation conducted using the catalyst precursor. Use of the catalyst prepared by heat treatment at approximately 875° C. provided about 19% less IDA as compared to use of the catalyst prepared by heat treatment at approximately 830° C.

Example 13

This example demonstrates the effect of catalyst iron content on formation of IDA during PMIDA oxidation.

A 7.5% Pt/1.5% Fe catalyst was prepared as described in Example 1; the platinum/iron mixture contained 1.722 g of iron chloride. A 7.5% Pt/3% Fe catalyst precursor was prepared as described in Example 1. Each precursor was heated in the tube reactor described in Example 2 in the presence of a hydrogen (10%, by volume) in argon atmosphere from approximately 20° C. to approximately 950° C. over the course of approximately 2 hours. The precursors were each then heated at approximately 950° C. for approximately 1 hour.

The catalysts were used to catalyze the oxidation of PMIDA under the conditions described in Example 3. One 60 minute reaction cycle was conducted using each catalyst. The IDA content (% by weight) of the product mixture was determined by HPLC after a reaction time of 60 minutes. The results are shown in Table 9.

TABLE 9

| Catalyst | IDA (% by weight) 1st cycle |
| --- | --- |
| 7.5% Pt/1.5% Fe | 0.125 |
| 7.5% Pt/3.0% Fe | 0.205 |

As shown in Table 9, use of the catalyst containing 1.5% by weight iron resulted in approximately 39% less IDA than use of the catalyst containing 3% by weight iron. These results suggest a positive correlation between catalyst iron content and IDA formation during the oxidation of PMIDA.

Example 14

This example demonstrates the effect of introducing gaseous ammonia to the catalyst heat treatment atmosphere on formation of IDA during PMIDA oxidation.

Four 5% Pt/1.5% Fe catalyst precursors were prepared as described in Example 5 and heat treated generally in accordance with the procedure described in Example 2 using varying heat treatment atmospheres.

The first precursor, the control, was heat treated in a hydrogen (5%, by volume) in helium atmosphere in the tube reactor described in Example 2 from approximately 20° C. to approximately 900° C. over the course of approximately 88 minutes. The catalyst precursor was then heated at approximately 900° C. for approximately 25 minutes. The hydrogen in helium atmosphere flowed through the reactor at a rate of approximately 60 cm³/min.

The second catalyst was prepared by heating the precursor in a hydrogen (5%, by volume), ammonia (0.03%, by volume) and helium atmosphere in the tube reactor described in Example 2 described above from approximately 20° C. to approximately 900° C. over the course of approximately 88 minutes. The catalyst precursor was then heated at approximately 900° C. for approximately 25 minutes. The hydrogen, ammonia and helium atmosphere flowed through the reactor at a rate of approximately 60 cm³/min.

The third catalyst was prepared by heating the precursor in a hydrogen (5%, by volume), ammonia (0.1%, by volume) and helium atmosphere in the tube reactor described in Example 2 from approximately 20° C. to approximately 900° C. over the course of approximately 88 minutes. The catalyst precursor was then heated at approximately 900° C. for approximately 25 minutes. The hydrogen, ammonia and helium atmosphere flowed through the reactor at a rate of approximately 60 cm³/min.

The fourth catalyst was prepared by heating the precursor in a hydrogen (5%, by volume), ammonia (0.33%, by volume) and helium atmosphere from approximately 20° C. to approximately 900° C. over the course of approximately 88 minutes. The catalyst was then heated at approximately 900° C. for approximately 25 minutes. The hydrogen, ammonia and helium atmosphere flowed through the reactor at a rate of approximately 60 cm³/min.

Each of the catalysts was used to catalyze the oxidation of PMIDA under the conditions described in Example 3 in a 60 minute reaction cycle. Catalyst loading was 0.15% (by weight) (0.21 g). The amount of IDA in each product mixture (% by weight) was determined by HPLC after a reaction time of 60 minutes. The results are shown in Table 10. As shown in Table 10, IDA production decreased as the amount of ammonia introduced into the catalyst heat treatment atmosphere increased.

TABLE 10

| $NH_3$ in heat treatment atmosphere | IDA (% by weight) 1st cycle |
|---|---|
| No $NH_3$ added (control) | 0.25 |
| 0.03% $NH_3$ | 0.156 |
| 0.1% $NH_3$ | 0.141 |
| 0.33% $NH_3$ | 0.135 |

Example 15

This example demonstrates the effect of modifying the catalyst heat treatment atmosphere on IDA yield during PMIDA oxidation.

5% Pt/1% Fe catalyst precursors prepared as described in Example 1 were heat treated generally in accordance with the procedure described in Example 2 using varying heat treatment atmospheres.

A first catalyst, the control, was prepared by heating the precursor (approximately 2 g) in a hydrogen (5%, by volume) in argon atmosphere in the tube reactor described in Example 2 from approximately 20° C. to approximately 900° C. over the course of approximately 2 hours. The catalyst precursor was then heated at approximately 900° C. for approximately 1 hour.

A second catalyst was prepared by heating the precursor in a hydrogen (5%, by volume) in argon atmosphere in the tube reactor described above from approximately 20° C. to approximately 900° C. over the course of approximately 1 hour. The catalyst precursor was then heated at approximately 900° C. for approximately 1 hour. Prior to contact with the catalyst precursor, the heat treatment gas was passed through a water trap set at approximately 70° C.

A third catalyst was prepared by heating the precursor in a hydrogen (5%, by volume) in argon atmosphere in the tube reactor described above from approximately 20° C. to approximately 900° C. over the course of approximately 2 hours. The catalyst precursor was then heated at approximately 900° C. for approximately 1 hour. Prior to contact with the catalyst precursor, the heat treatment gas was passed through a 1M aqueous ammonium carbonate $((NH_4)_2CO_3)$ solution at approximately 20° C.

A fourth catalyst was prepared by heating the precursor in the presence of a hydrogen (5%, by volume), nitrous oxide $(N_2O)$ (1%, by volume) and argon atmosphere in the tube reactor described above from approximately 20° C. to approximately 900° C. over the course of approximately 2 hours. The catalyst precursor was then heated at approximately 900° C. for approximately 1 hour.

Each of the catalysts was used to catalyze the oxidation of PMIDA under the conditions described in Example 3. Catalyst loading was 0.15% by weight (0.21 g). The amount of IDA (% by weight) in the product mixture after a reaction time of 60 minutes was determined by HPLC. The results are shown in Table 11. As shown in Table 11, use of the catalysts prepared by each of the three modifications to the catalyst heat treatment atmosphere resulted in lower IDA production than use of the control sample.

TABLE 11

| Heat treatment atmosphere modification | IDA (% by weight) after 60 minutes |
|---|---|
| None | 0.24 |
| Bubbling through water at 70° C. | 0.158 |
| Bubbling through 1M $(NH_4)_2CO_3$ solution at room temp. | 0.176 |
| Blending with 1% $N_2O$ | 0.125 |

Example 16

This example demonstrates the effect of pre-soaking a catalyst in formaldehyde (HCHO) on IDA formation during PMIDA oxidation.

Two 5% Pt/1% Fe catalysts, A and B, were prepared as described in Examples 1 and 2 (including heat treatment at a maximum temperature of approximately 850° C.). Samples of catalyst A (0.21 g) and catalyst B (0.21 g) were each contacted with approximately 100 ml of a mixture of formaldehyde and water containing 5000 parts per million (ppm) of formaldehyde under nitrogen and at approximately 80° C. for approximately 20 minutes.

Four catalyst samples (pre-soaked catalyst A, un-soaked catalyst A control, pre-soaked catalyst B, and un-soaked catalyst B control) were each used to catalyze the oxidation of PMIDA under the conditions of Example 3. Catalyst loading was 0.15% by weight (0.21 g). The amount of IDA in the product mixture (% by weight) after a reaction time of 60 minutes was determined by HPLC. The results are shown in Table 12. As shown in Table 12, use of the presoaked catalysts resulted in lower IDA production than use of their corresponding controls.

TABLE 12

| Catalyst | IDA (% by weight) after 60 minutes |
|---|---|
| A, pre-soaked in HCHO | 0.22 |
| A, control | 0.24 |
| B, pre-soaked in HCHO | 0.19 |
| B, control | 0.25 |

Example 17

This example demonstrates the effect of conditioning a catalyst by oxidation of formaldehyde (HCHO) or formic acid (HCOOH) in the presence of the catalyst on IDA production during PMIDA oxidation catalyzed by the conditioned catalyst.

A 5% Pt/1% Fe catalyst prepared as described in Examples 1 and 2 (0.21 g) was slurried in an aqueous mixture (100 g) of formaldehyde and water having a formaldehyde concentration of 5000 ppm. The slurry was contacted with oxygen at a rate of approximately 100 cm$^3$/min at approximately 80° C. for approximately 20 minutes to oxidize formaldehyde. The formaldehyde oxidation mixture was then filtered to isolate the catalyst.

A 5% Pt/1% Fe catalyst prepared as described in Examples 1 and 2 (0.21 g) was slurried in an aqueous mixture (100 g) containing formic acid at a concentration of 10,000 ppm. The slurry was contacted with oxygen at a rate of approximately 100 cm$^3$/min at approximately 80° C. for approximately 20 minutes to oxidize formic acid. The formic acid oxidation mixture was then filtered to isolate the catalyst.

The conditioned catalysts and a control 5% Pt/1% Fe catalyst prepared as described in Examples 1 and 2 were used to catalyze the oxidation of PMIDA under the conditions of Example 3 at a catalyst loading of 0.15% by weight (0.21 g). The amount of IDA (% by weight) in the PMIDA oxidation product mixture after a reaction time of 60 minutes was determined by HPLC for each run.

The IDA contents of the PMIDA oxidation product mixtures are summarized in Table 13. As shown in Table 13, use of the conditioned catalysts resulted in lower IDA production than use of the control catalyst.

TABLE 13

| Pre-Treatment Condition | IDA (% by weight) after 1st cycle |
|---|---|
| oxidation of HCHO | 0.19 |
| oxidation of HCOOH | 0.18 |
| Control | 0.24 |

Example 18

This example details the effect of leaching agents on platinum leaching from catalysts prepared at varying heat treatment temperatures.

Three mixtures containing a 5% Pt/1.5% Fe catalyst prepared in accordance with Examples 1, 2 and 5, including heat treatment at a maximum temperature of approximately 850° C., (2.5 g) and each of three leaching agents (glycine (0.803 g), AMPA (1.1875 g) or N-(phosphonomethyl)glycine (22.5 g)) and water were prepared. Three mixtures containing a 5% Pt/1.5% Fe catalyst also prepared in accordance with Examples 1, 2 and 5, including heat treatment at a maximum temperature of approximately 950° C., (2.5 g) and each of three leaching agents (glycine (0.803 g), AMPA (1.1875 g) or N-(phosphonomethyl)glycine (22.5 g)) and water were also prepared. The total mass of each of the 6 mixtures was approximately 250 grams.

Each of the 6 mixtures was heated while stirred at approximately 100° C. for approximately 2 hours in the presence of an oxygen flow of approximately 200 cm$^3$/min (i.e., approximately 0.8 cm$^3$/minute/gram aqueous mixture) and under a pressure of approximately 75 psig. The mixture was filtered to recover the catalyst. The platinum content of this first filtrate was determined by Inductively Coupled Plasma (ICP) analysis to determine the amount of platinum removed from the catalyst. ICP analysis was carried out using a VG PQ ExCell Inductively Coupled Plasma-Mass Spectrometer (ICP-MS), or an IRIS Advantage Inductively Coupled Plasma Optical Emission Spectrometer (ICP-OES) (commercially available from Thermo Jarrell Ash Corp., Thermo Elemental, Franklin, Mass.).

The recovered catalyst was then vacuum dried and subjected to ammonia extraction to determine the amount of platinum which was removed from the catalyst but subsequently re-deposited onto the carbon support and thus not detected in the initial ICP analysis. Ammonia extraction was carried out by heating a mixture of the recovered catalyst sample (0.75 g) and a 1% by weight aqueous mixture of ammonia (75 g) to approximately 100° C. while stirring under a $N_2$-atmosphere at a pressure of 75 psig for 1 hour. The heated mixture was filtered and this second filtrate was analyzed by ICP analysis to determine its platinum content as described above.

The combined platinum content of the first and second filtrates is then used to determine the proportion of platinum originally present which was leached from the carbon support. The total platinum leaching for each of the six mixtures are summarized below in Table 14. As shown in Table 14, catalysts prepared at higher heat treatment temperatures exhibited lower platinum leaching.

TABLE 14

| Leaching agent | Total platinum leaching (%) |
|---|---|
| Glycine | |
| 850° C. | 1.9714 |
| 950° C. | 1.0962 |
| AMPA | |
| 850° C. | 3.994 |
| 950° C. | 2.344 |
| N-(phosphonomethyl)glycine | |
| 850° C. | 1.814 |
| 950° C. | 1.006 |

Example 19

Electron Microscopy Characterization of Catalysts

Electron microscopy techniques were used to analyze the size distribution, spatial distribution, and composition of the metal particles of various catalysts prepared in accordance with the present invention.

A catalyst sample was first embedded in an EM Bed 812 resin (Electron Microscopy Sciences, Fort Washington, Pa.). The resin was then polymerized at about 60° C. for approximately 24 hours. The resulting cured block was ultramicrotomed into slices having a thickness of about 50 nm. These slices were then transferred to 200 mesh copper grids for electron microscopy observation.

High-resolution analytical electron microscopy analyses were carried out using a Vacuum Generators dedicated scanning transmission electron microscope (Model No. VG HB501, Vacuum Generators, East Brinstead, Sussex, England) with an image resolution of less than 0.3 nm. The microscope was operated at 100 kV. The vacuum in the specimen chamber area was below about 106 Pa. A digital image acquisition system (ES Vision Data Acquisition System, EmiSpec Sys., Inc., Tempe, Ariz.) was used to obtain high-resolution electron microscopy images. A windowless energy dispersive X-ray spectrometer (Link LZ-5 EDS Windowless Detector, Model E5863, High Wycombe, Bucks, England) was used to acquire high energy resolution X-ray spectra from individual metal particles. Because of its high atomic-number sensitivity, high-angle annular dark-field (HAADF) microscopy was used to observe the metal particles. An electron probe size of less than about 0.5 nm was used to obtain the HAADF images, and a probe size of less than about 1 nm was used to obtain high energy resolution X-ray spectra.

Compositional analysis of bimetallic nanoparticles was determined by quantification of X-ray energy dispersive spectrum (XEDS). The XEDS spectrum was analyzed and quantified to provide compositional information of individual bimetallic nanoparticles. The Cliff-Lorimer method is used to determine the composition of the individual bimetallic nanoparticles:

$$C_{Pt}/C_{Fe} = k_{PtFe}(I_{Pt}/I_{Fe})$$

$$C_{Pt} + C_{Fe} = 1$$

For example, where $C_{Pt}$ and $C_{Fe}$ represent the weight percent of Pt and Fe, respectively, in the individual PtFe bimetallic nanoparticles; $I_{Pt}$ and $I_{Fe}$ represent the integrated characteristic X-ray intensity of the Pt and Fe peaks in the XEDS spectrum (corrected for background), respectively; and $k_{PtFe}$ is the "K ratio" which is a constant for a fixed experiment and its value is determined by using known standards. After the composition of the individual bimetallic nanoparticles was determined a composition-size plot displayed in FIGS. 10 and 13 was prepared.

Example 20

Catalysts containing approximately 5% platinum and approximately 0.5% iron (5% Pt/0.5% Fe) were prepared in a manner similar to that described in one or more of the Examples provided herein (e.g., Examples 2 and 7), including heat treatment in a non-oxidizing environment following noble metal deposition at a maximum temperature of approximately 850° C. Other 5% Pt/0.5% Fe were prepared in essentially the same manner, but at a maximum heat treatment temperature of approximately 950° C. The particle size of metal particles of the catalysts of various sizes present on the carbon support surface (e.g., up to 10 nm or 15 nm, in their largest dimension) were analyzed using electron microscopy techniques as described above in Example 19.

Figure 6:
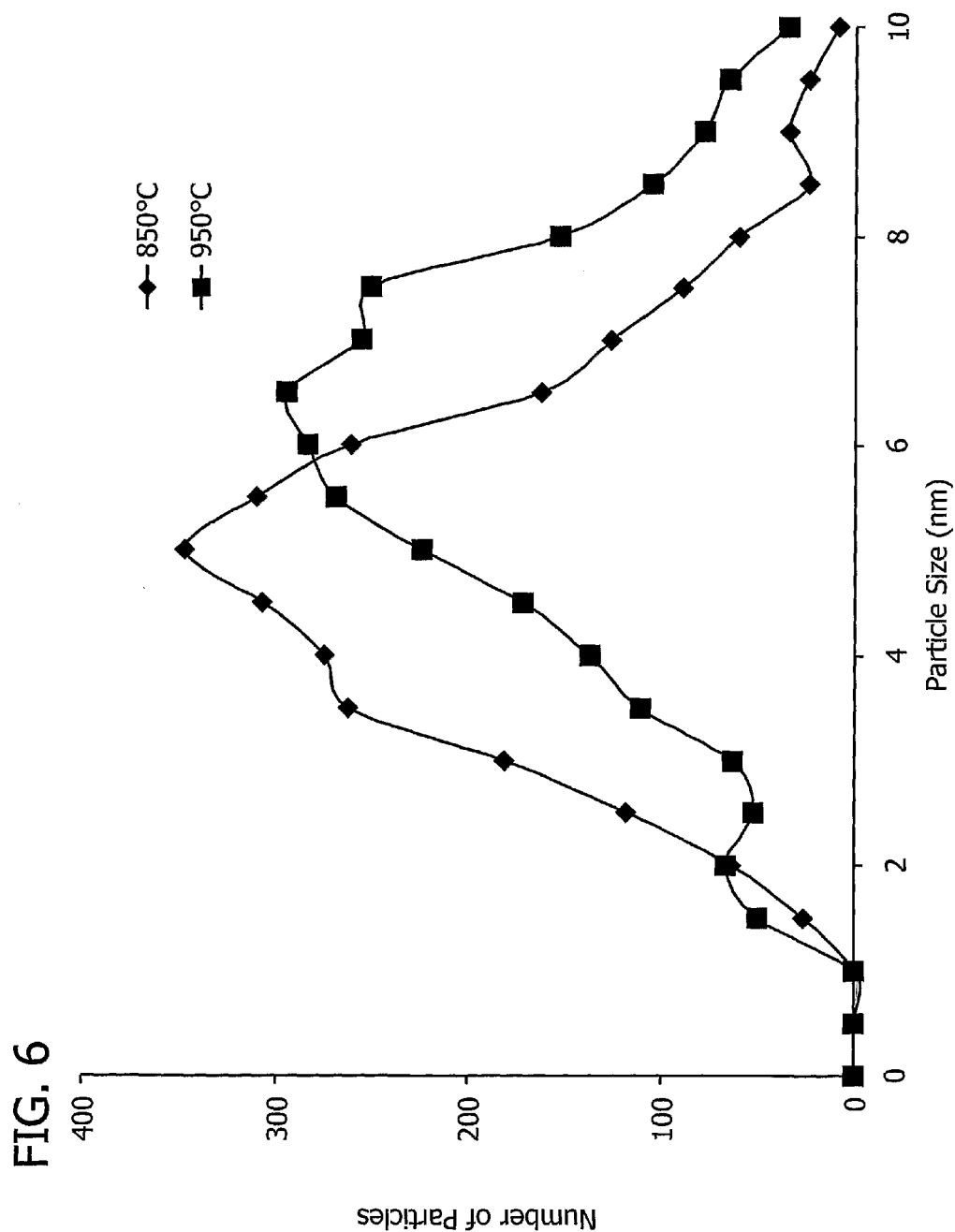
FIG. 6 shows the particle size distributions of certain metal particles of the catalysts described in Example 20.
Figure 7:
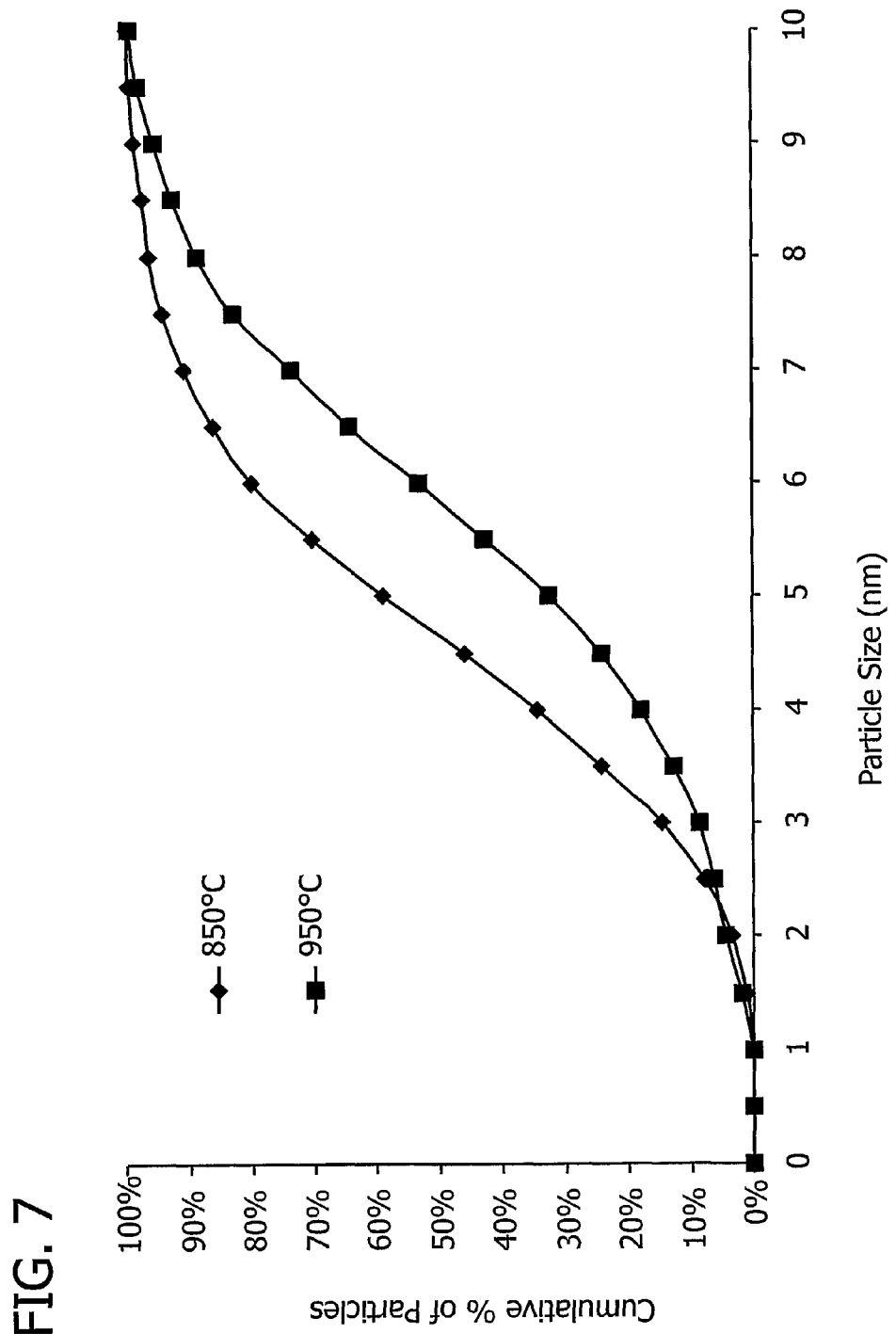
FIG. 7 shows the cumulative percentage of metal particles analyzed as described in Example 20 versus particle size.

FIGS. 6 and 7 show results for a 5% Pt/0.5% Fe catalyst prepared at each maximum heat treatment temperature.

FIG. 6 shows the particle size distributions for metal particles of the two catalysts, in terms of the number of particles of various sizes analyzed. A total of 2,691 particles were analyzed for each sample.

FIG. 7 shows the cumulative percentage of the various metal particles analyzed at particle sizes ranging from 0 to 10 nm. As shown in FIG. 7, the catalyst prepared at a maximum heat treatment temperature of approximately 950° C. generally contained a reduced proportion of smaller metal particles than the catalyst prepared at a maximum heat treatment temperature of approximately 850° C. For example, less than 20% of the particles of the catalyst prepared at a maximum heat treatment temperature of approximately 950° C. had a particle size of less than 4 nm whereas approximately 35% of the particles of the catalyst prepared at a maximum heat treatment temperature of approximately 850° C. had a particle size of less than 4 nm. Also shown in FIG. 7, approximately 15% of the particles of the catalyst prepared at a maximum heat treatment temperature of approximately 950° C. analyzed had a particle size of from about 2 to about 4 nm.

The average particle size for metal particles of the catalyst prepared at a maximum heat treatment temperature of approximately 950° C. was about 5.8 nm; the average particle size for metal particles of the catalyst prepared at a maximum heat treatment temperature of approximately 850° C. was about 5 nm.

Figure 19:
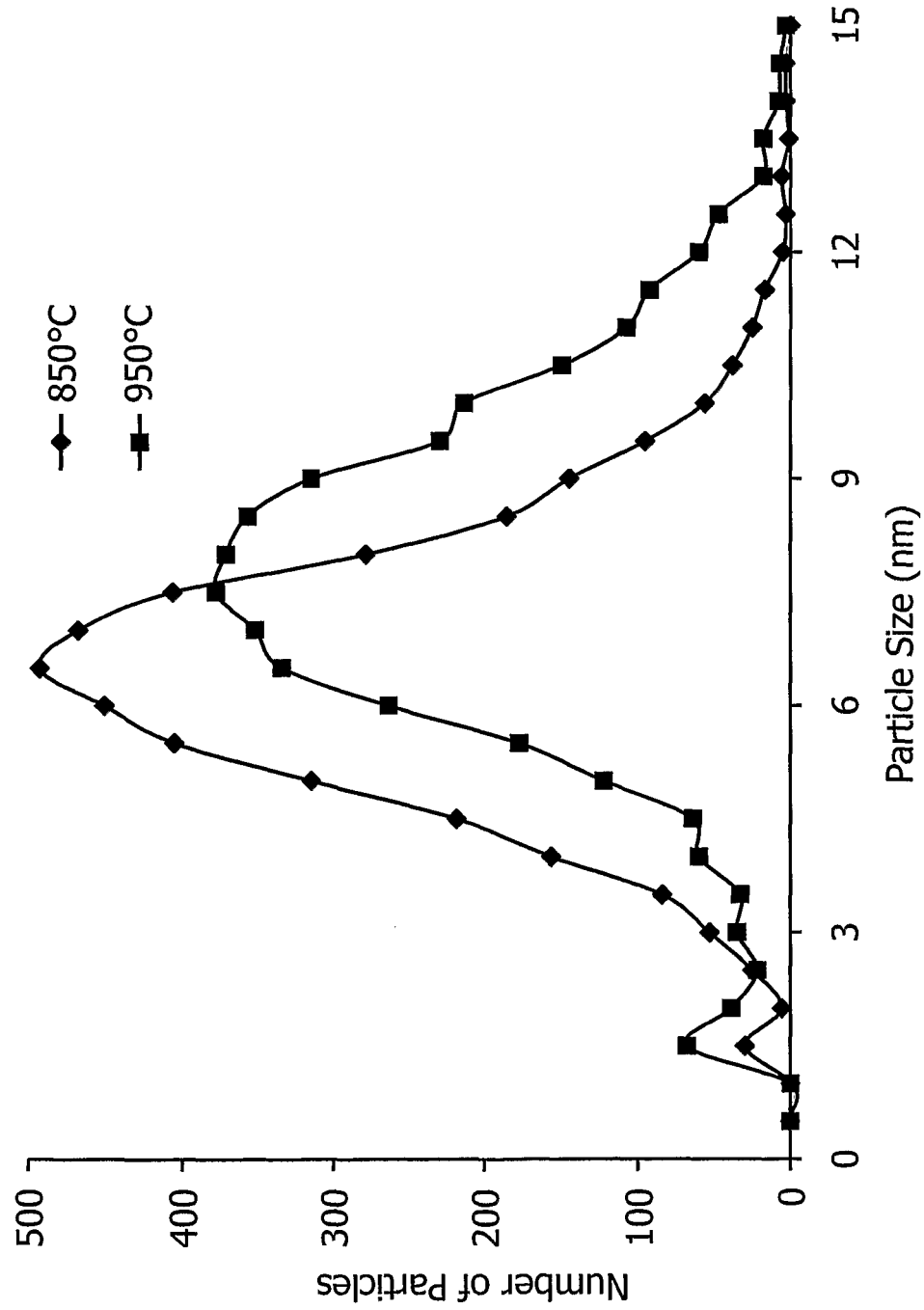
FIG. 19 shows the particle size distributions of certain metal particles of the catalysts described in Example 20.
Figure 20:
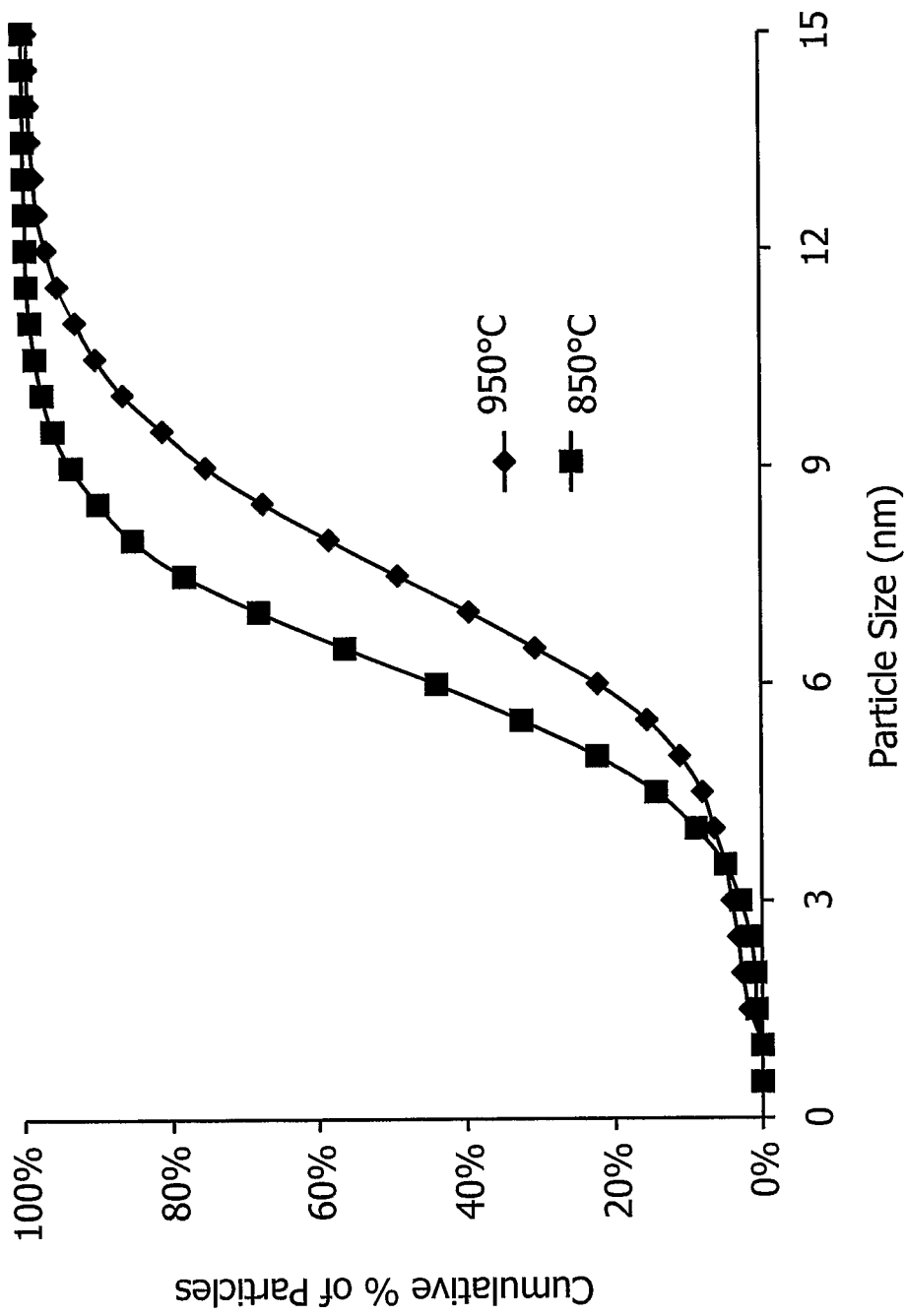
FIG. 20 shows the cumulative percentage of metal particles analyzed as described in Example 20 versus particle size.

FIGS. 19 and 20 also show electron microscopy results for 5% Pt/0.5% Fe catalysts prepared as described above by heat treatment in a non-oxidizing environment at maximum temperatures of approximately 850° C. and approximately 950° C. FIG. 19 shows the particle size distributions for the two catalysts, in terms of the number of particles analyzed, at sizes ranging from 0 to 15 nm. FIG. 20 shows the cumulative percentage of the various metal particles analyzed at particle sizes ranging from 0 to 15 nm. As shown in FIG. 20, the catalyst prepared at a maximum heat treatment temperature of approximately 950° C. generally contained a reduced proportion of smaller metal particles. For example, approximately 10% of the particles of the catalyst prepared at a maximum heat treatment temperature of approximately 950° C. had a particle size of less than 5 nm whereas approximately 22% of the particles of the catalyst prepared at a maximum heat treatment temperature of approximately 850° C. had a particle size of less than 5 nm.

Example 21

This example demonstrates the effect of heat treatment temperature and atmosphere on platinum/iron metal catalyst particles.

A 5% Pt/1% Fe catalyst was prepared in a manner similar to that described in one or more of the Examples provided herein (e.g., Examples 2 and 7), including heat treatment at a maximum temperature of approximately 900° C. for approximately 1 hour except, prior to contact with the sample, the heat treatment gas (hydrogen (5%, by volume) in argon) was passed through a water trap to saturate the gas with water vapor. (Sample 1)

A second 5% Pt/1% Fe catalyst was prepared in a manner similar to that described in one or more of the Examples provided herein (e.g., Examples 2 and 7), including heat treatment at a maximum temperature of approximately 900° C. for approximately 1 hour. (Sample 2)

Figure 8:
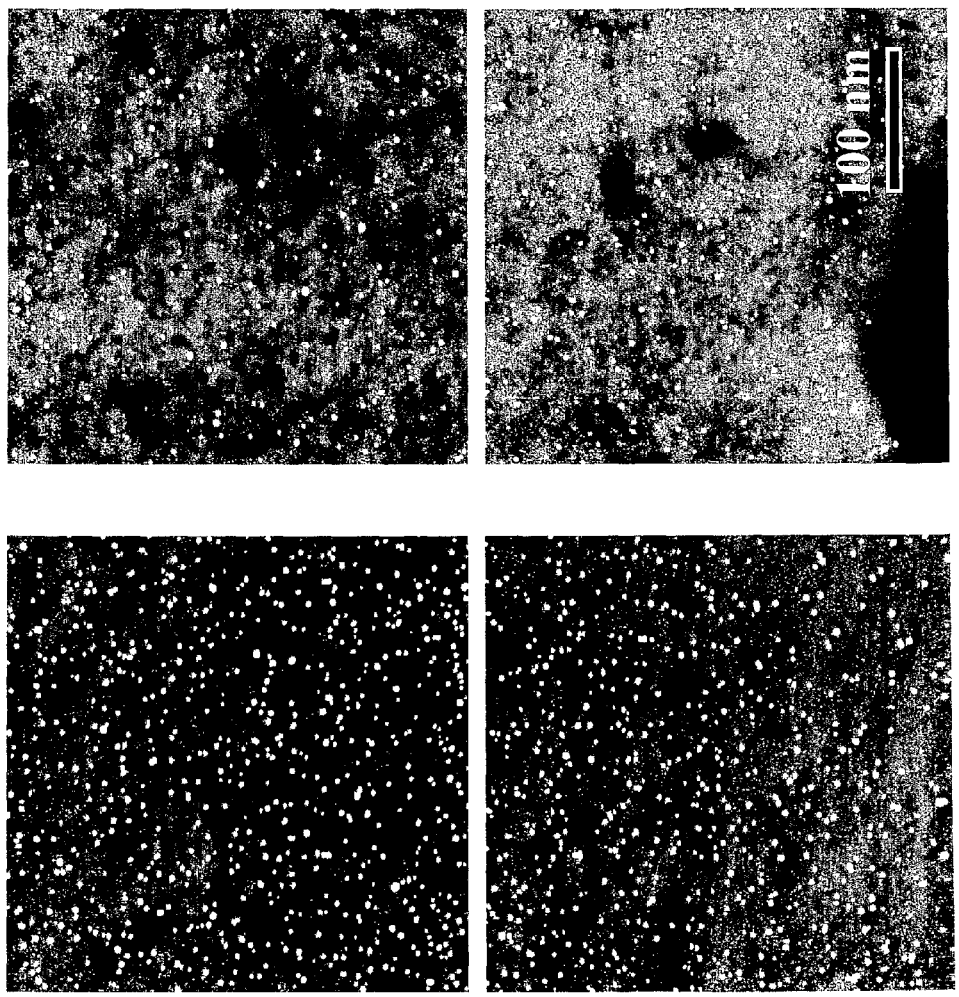
FIGS. 8 and 9 are high-angle dark-field images of different regions of a catalyst prepared as described in Example 21.
Figure 9:
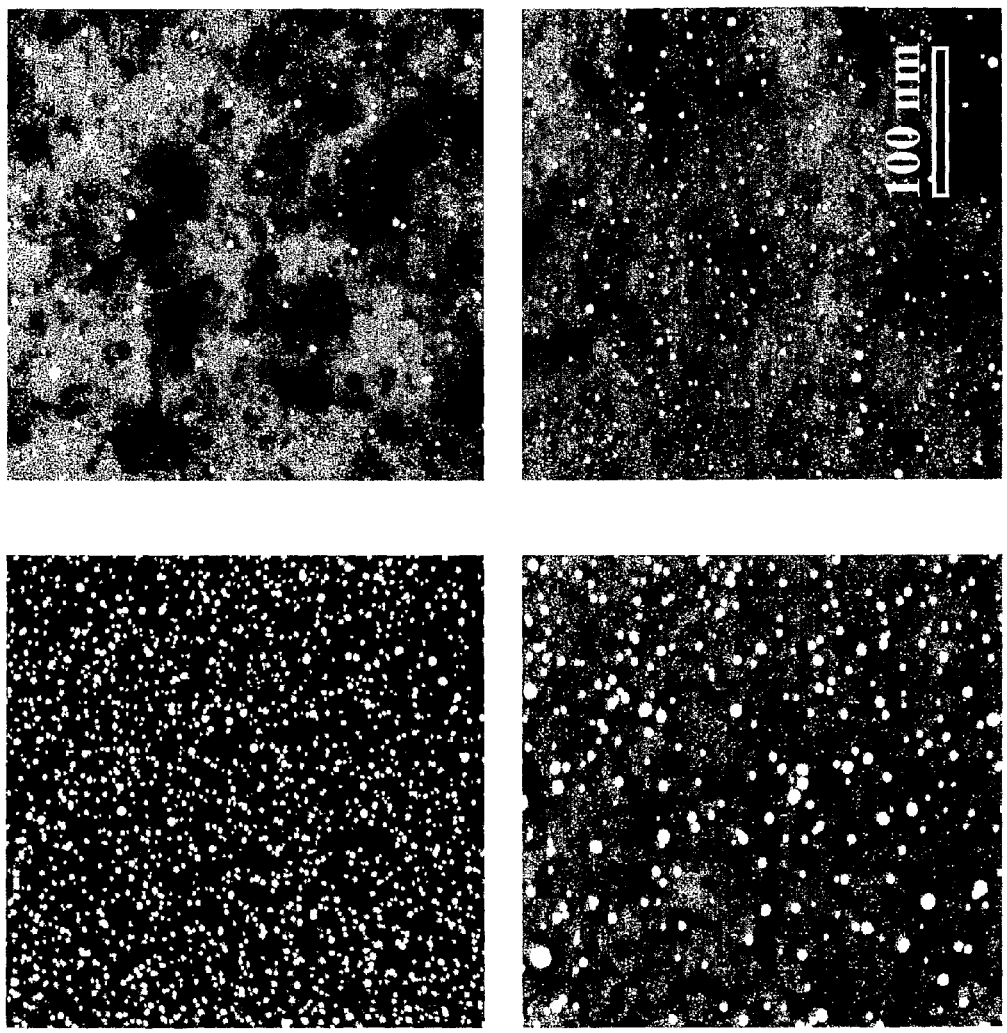

FIGS. 8 and 9 are high angle dark-field images of Sample 1 (water vapor introduced to the heat treatment atmosphere) showing the size and spatial distributions of Pt/Fe nanoparticles in different regions of the carbon support. These images were obtained as described above in Example 19.

Figure 10:
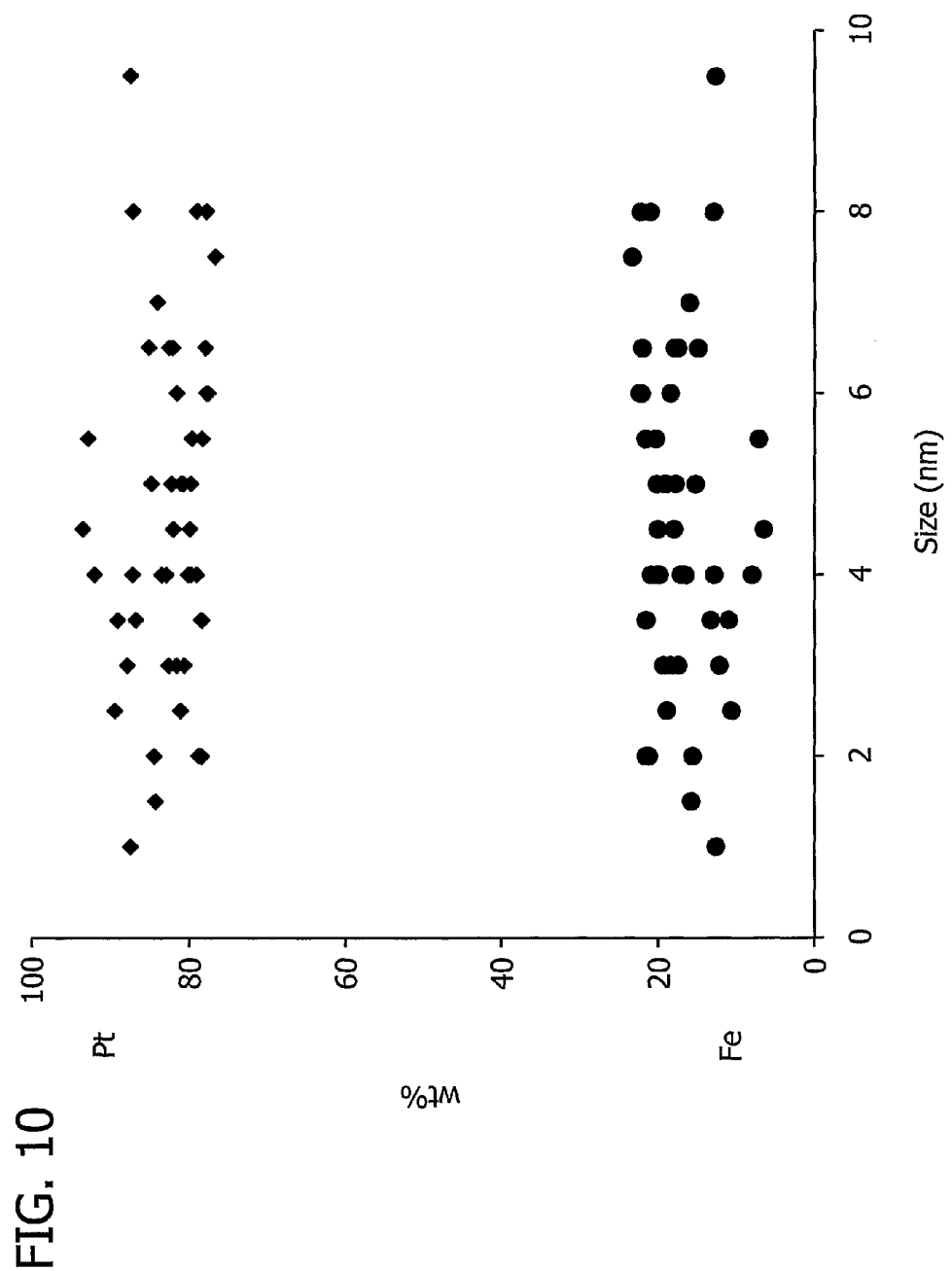
FIG. 10 is a size-composition plot of various metal particles of a catalyst prepared as described in Example 21.

FIG. 10 is a size-composition plot of individual Pt/Fe nanoparticles present in different regions of the carbon support of Sample 1. The Pt/Fe compositions of the nanoparticles were determined as described in Example 19.

Figure 11:
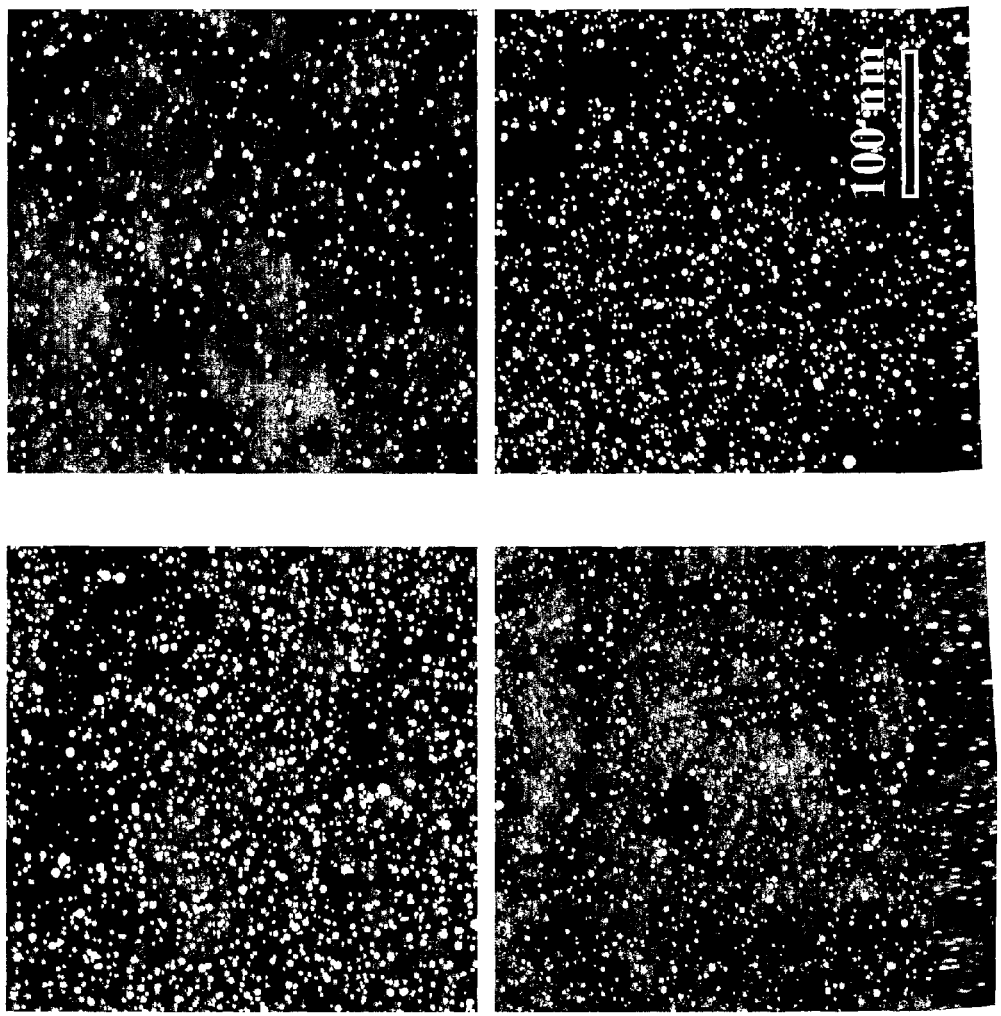
FIGS. 11 and 12 are high-angle dark-field images of different regions of a catalyst prepared as described in Example 21.
Figure 12:
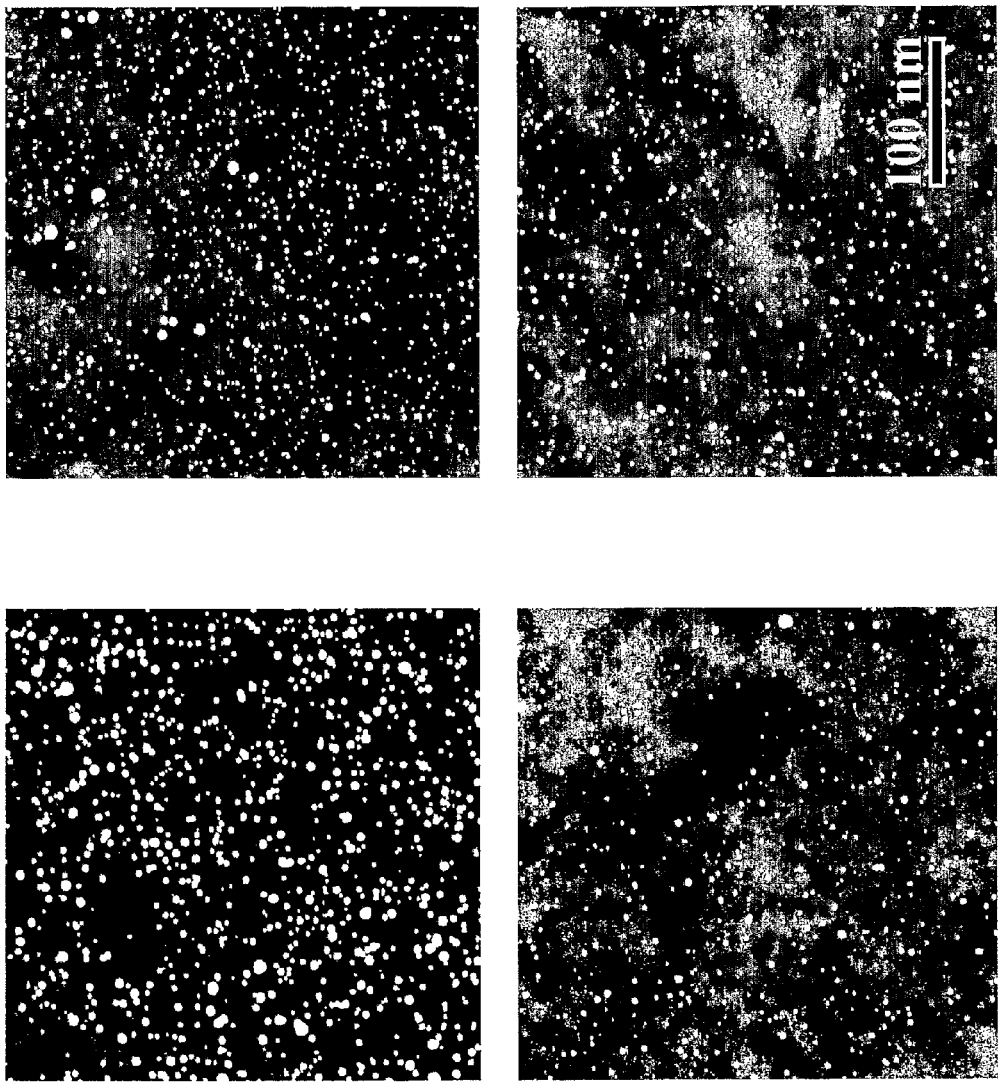

FIGS. 11 and 12 are high angle dark-field images of Sample 2 showing the size and spatial distributions of Pt/Fe nanoparticles present in different regions of the carbon support. These images were obtained as described above in Example 19.

Figure 13:
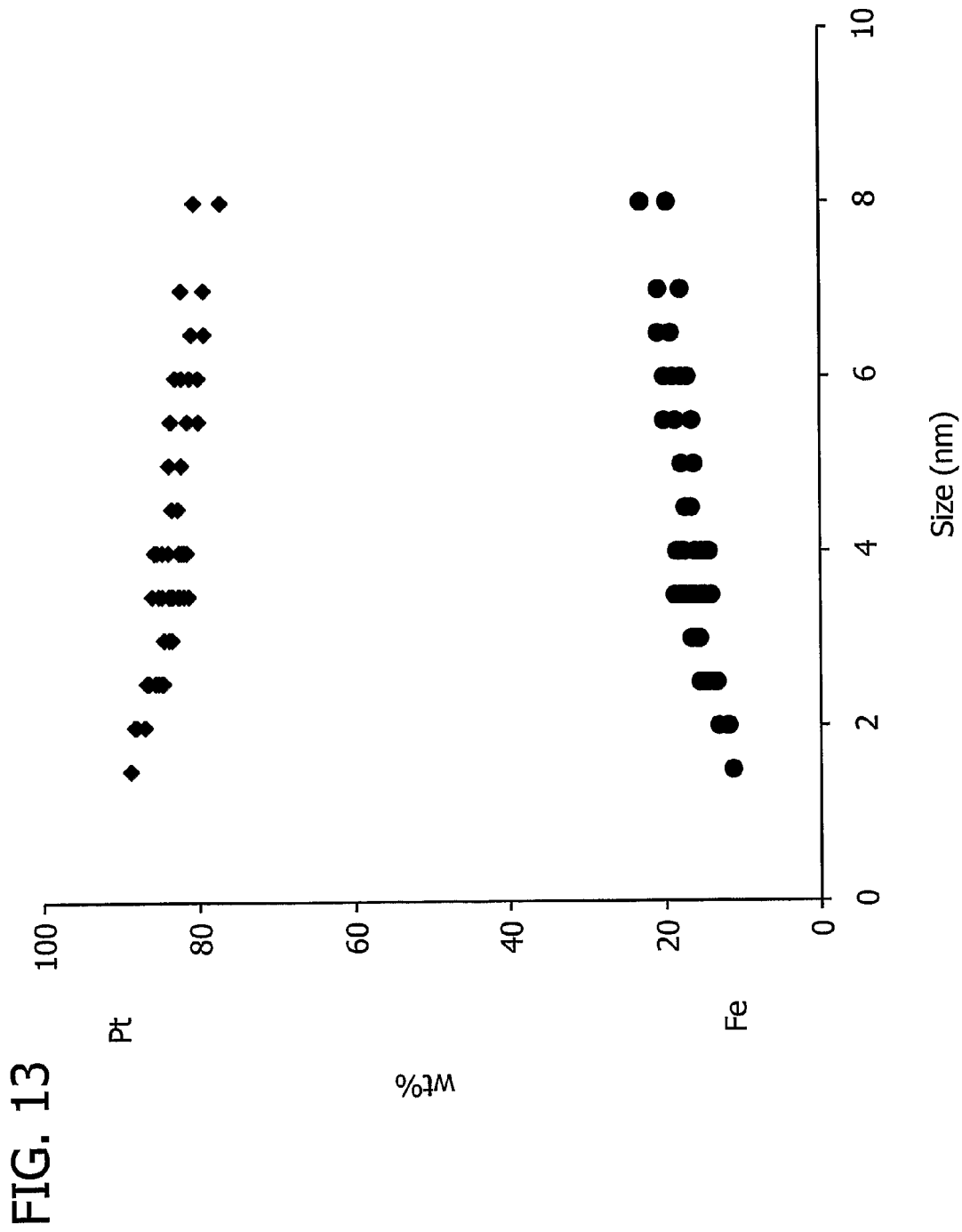
FIG. 13 is a size-composition plot of various metal particles of a catalyst prepared as described in Example 21.

FIG. 13 is a size-composition plot of individual Pt/Fe nanoparticles found in different regions of the carbon support of Sample 2. The Pt/Fe compositions of the nanoparticles were determined as described in Example 19.

Figure 14:
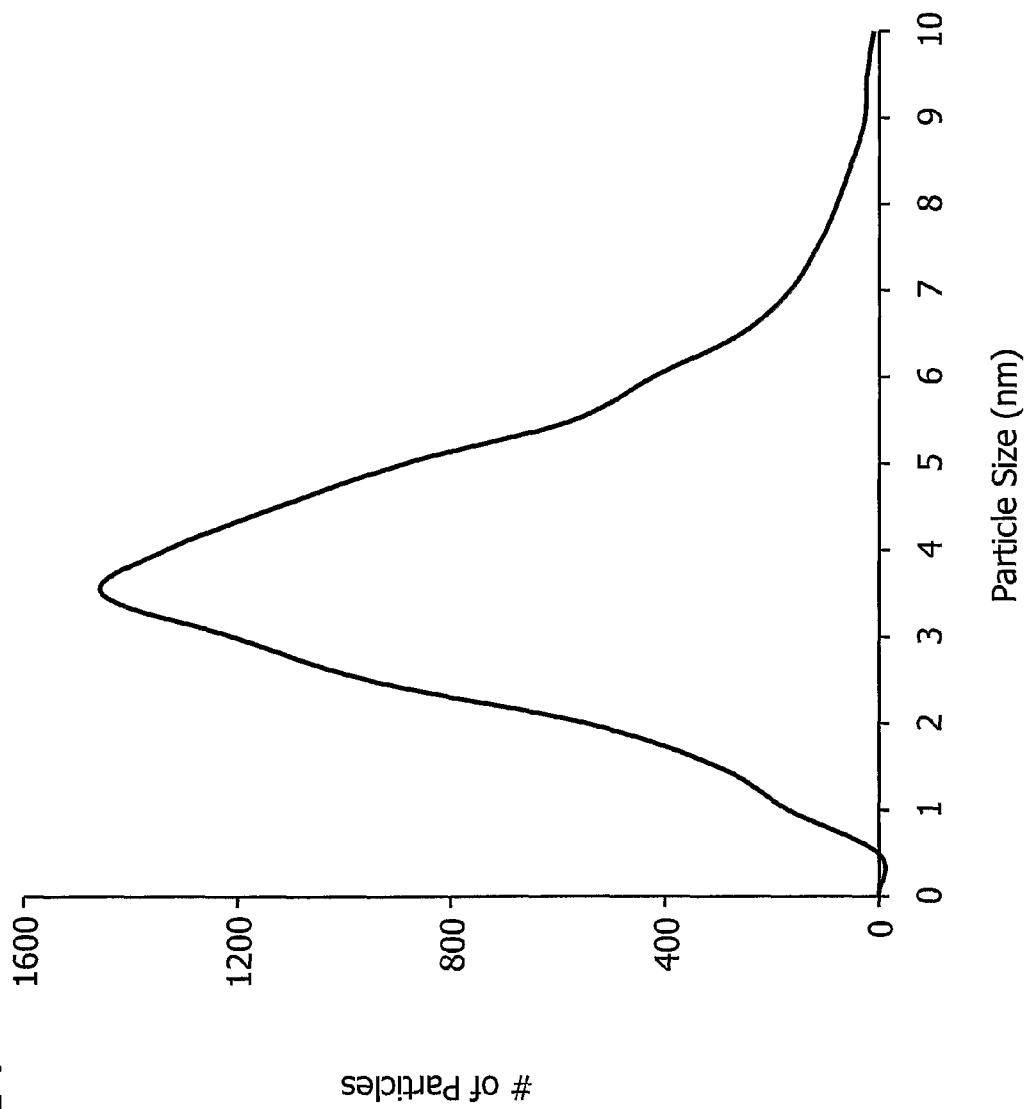
FIGS. 14 and 15 show the particle size distribution of certain metal particles of catalysts described in Example 21.

FIG. 14 shows the particle size distribution of Pt/Fe particles of Sample 1 (water vapor introduced to the heat treatment atmosphere). A total of 9,716 particles were analyzed using a scanning transmission electron microscope as described in Example 19. The median particle size was 3.6 nm.

Figure 15:

FIG. 15 shows the particle size distribution of Pt/Fe particles of Sample 2. A total of 14,320 particles were analyzed using a scanning transmission electron microscope as described in Example 19. The median particle size was 3.0 nm.

Figure 16:
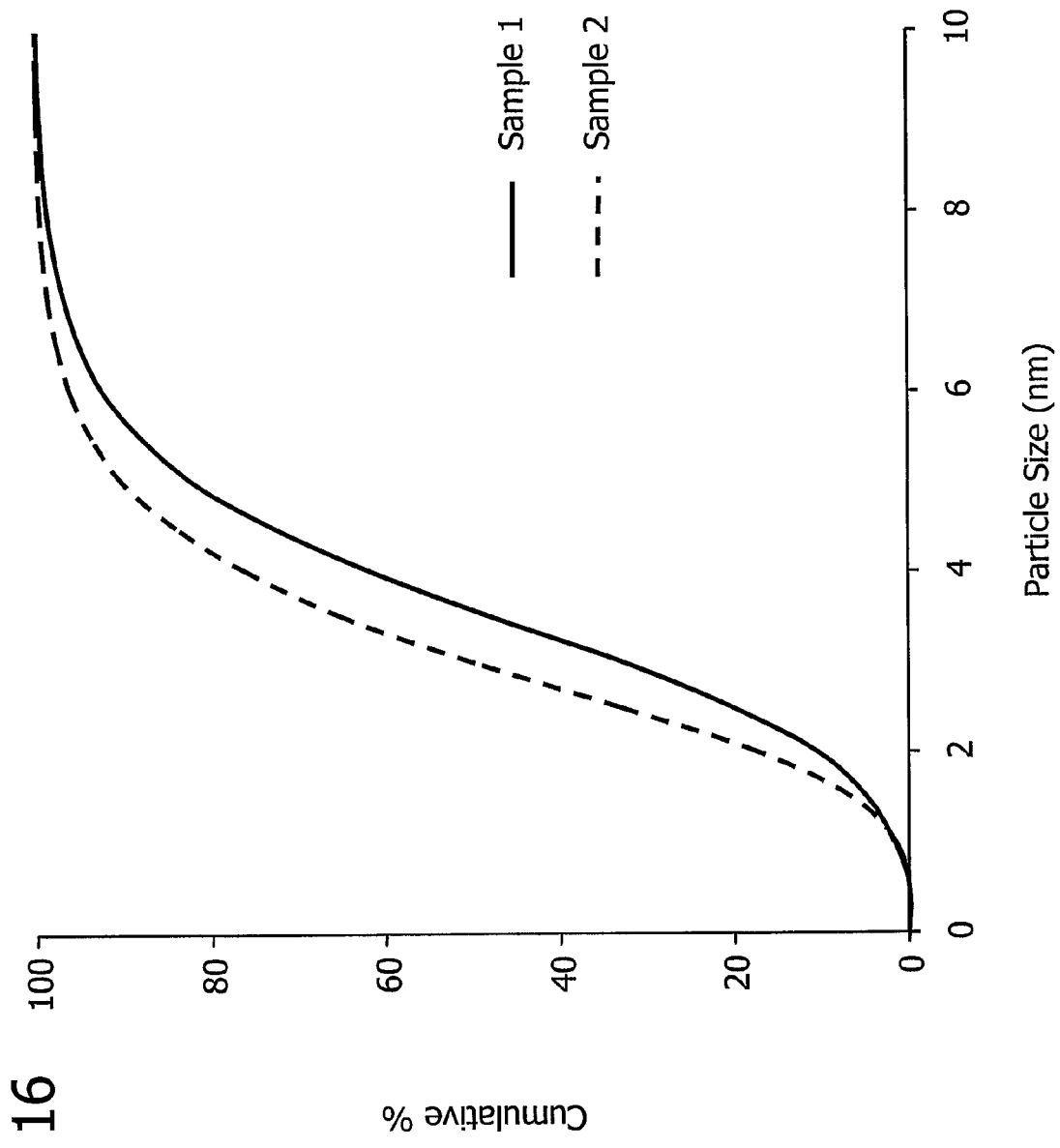
FIG. 16 is a comparison of the individual particle size distributions of certain metal particles of catalysts described in Example 21.

FIG. 16 is a comparison of the particle size distribution obtained for Sample 1 (water vapor introduced to the heat treatment atmosphere) and Sample 2. As shown in FIG. 16, Sample 1 generally contained a reduced proportion of smaller particles. For example, approximately 60% of the particles of Sample 1 analyzed had a particle size, in their largest dimension, of less than 4 nm whereas approximately 75% of the particles of Sample 2 had a particle size of less than 4 nm.

Example 22

Two 5% Pt/1.5% Fe catalyst precursors were prepared as described in Example 5.

Sample 1 was heat treated as described in Example 2 at a maximum temperature of approximately 900° C.; the sample was heated at approximately 900° C. for approximately 30 minutes. Prior to contact with the sample, the heat treatment gas was passed through a water trap set at approximately 20° C. to saturate the gas with water vapor. The heat treatment gas was passed through the water trap for 6 second intervals, followed by 60 second intervals in which the heat treatment gas bypassed the water trap.

A control sample, Sample 2, was prepared in the same manner as Sample 1 but without intermittent saturation of the heat treatment gas with water vapor.

Example 23

Protocol A

The following example details CO chemisorption analysis used to determine the exposed metal surface areas of catalysts prepared as described herein. The method described in this example is referenced in this specification and appended claims as "Protocol A."

This protocol subjects a single sample to two sequential CO chemisorption cycles.

Cycle 1 measures initial exposed noble metal at zero valence state. The sample is vacuum degassed and treated with oxygen. Next, residual, un-adsorbed oxygen is removed and the catalyst is then exposed to CO. The volume of CO taken up irreversibly is used to calculate initial noble metal (e.g., $Pt^0$) site density.

Cycle 2 measures total exposed noble metal. Without disturbing the sample after cycle 1, it is again vacuum degassed and then treated with flowing hydrogen, and again degassed. Next the sample is treated with oxygen. Finally, residual, non-adsorbed oxygen is removed and the catalyst is then again exposed to CO. The volume of CO taken up irreversibly is used to calculate total exposed noble metal (e.g., $Pt^0$) site density. See, for example, Webb et al., Analytical Methods in Fine Particle Technology, Micromeritics Instrument Corp., 1997, for a description of chemisoprtion analysis. Sample preparation, including degassing, is described, for example, at pages 129-130.

Equipment:

Micromeritics (Norcross, Ga.) ASAP 2010~ static chemisorption instrument; Required gases: UHP hydrogen; carbon monoxide; UHP helium; oxygen (99.998%); Quartz flow through sample tube with filler rod; two stoppers; two quartz wool plugs; Analytical balance.

Preparation:

Insert quartz wool plug loosely into bottom of sample tube. Obtain tare weight of sample tube with 1st wool plug. Pre-weigh approximately 0.25 grams of sample then add this on top of the 1st quartz wool plug. Precisely measure initial sample weight. Insert 2nd quartz wool plug above sample and gently press down to contact sample mass, then add filler rod and insert two stoppers. Measure total weight (before degas): Transfer sample tube to degas port of instrument then vacuum to <10 μm Hg while heating under vacuum to 150° C. for approximately 8-12 hours. Release vacuum. Cool to ambient temperature and reweigh. Calculate weight loss and final degassed weight (use this weight in calculations).

Cycle 1:

Secure sample tube on analysis port of static chemisorption instrument. Flow helium (approximately 85 $cm^3$/minute) at ambient temperature and atmospheric pressure through sample tube, then heat to 150° C. at 5° C./minute. Hold at 150° C. for 30 minutes. Cool to 30° C.

Evacuate sample tube to <10 μm Hg at 30° C. Hold at 30° C. for 15 minutes. Close sample tube to vacuum pump and run leak test. Evacuate sample tube while heating to 70° C. at 5° C./min. Hold for 20 minutes at 70° C.

Flow oxygen (approximately 75 $cm^3$/minute) through sample tube at 70° C. and atmospheric pressure for 50 minutes.

Evacuate sample tube at 70° C. for 5 minutes.

Flow helium (approximately 85 $cm^3$/minute) through sample tube at atmospheric pressure and increase to 80° C. at 5° C./minute. Hold at 80° C. for 15 minutes.

Evacuate sample tube at 80° C. for 60 minutes and hold under vacuum at 80° C. for 60 minutes. Cool sample tube to 30° C. and continue evacuation at 30° C. for 30 minutes. Close sample tube to vacuum pump and run leak test.

Evacuate sample tube at 30° C. for 30 minutes and hold under vacuum at 30° C. for 30 minutes.

For a first CO analysis, CO uptakes are measured under static chemisorption conditions at 30° C. and starting manifold pressures of 50, 100, 150, 200, 250, 300, 350 and 400 mm Hg (gauge) to determine the total amount of CO adsorbed (i.e., both chemisorbed and physisorbed).

Pressurize manifold to the starting pressure (e.g., 50 mm Hg). Open valve between manifold and sample tube allowing CO to contact the sample in the sample tube. Allow the pressure in the sample tube to equilibrate. The reduction in pressure from the starting manifold pressure to equilibrium pressure in the sample tube indicates the volume of CO uptake by the sample.

Close valve between the manifold and sample tube and pressurize the manifold to the next starting pressure (e.g., 100 mm Hg). Open valve between manifold and sample tube allowing CO to contact the sample in the sample tube. Allow the pressure in the sample tube to equilibrate to determine the volume of CO uptake by the sample. Perform for each starting manifold pressure.

Evacuate sample tube at 30° C. for 30 minutes.

For a second CO analysis, CO uptakes are measured under static chemisorption conditions at 30° C. and starting manifold pressures of 50, 100, 150, 200, 250, 300, 350 and 400 mm Hg (gauge) as described above for the first CO analysis to determine the total amount of CO physisorbed.

Cycle 2:

After the second CO analysis of Cycle 1, flow helium (approximately 85 cm$^3$/minute) at 30° C. and atmospheric pressure through sample tube then heat to 150° C. at 5° C./minute. Hold at 150° C. for 30 minutes.

Cool to 30° C. Evacuate sample tube to <10 μm Hg at 30° C. for 15 minutes. Hold at 30° C. for 15 minutes.

Close sample tube to vacuum pump and run leak test.

Evacuate sample tube at 30° C. for 20 minutes.

Flow hydrogen (approximately 150 cm$^3$/minute) through sample tube at atmospheric pressure while heating to 150° C. at 10° C./min. Hold at 150° C. for 15 minutes.

Evacuate sample tube at 150° C. for 60 minutes. Cool sample tube to 70° C. Hold at 70° C. for 15 minutes.

Flow oxygen (approximately 75 cm$^3$/minute) through sample tube at atmospheric pressure and 70° C. for 50 minutes.

Evacuate sample tube at 70° C. for 5 minutes.

Flow helium (approximately 85 cm$^3$/minute) through sample tube at atmospheric pressure and increase temperature to 80° C. at 5° C./minute. Hold at 80° C. for 15 minutes. Evacuate sample tube at 80° C. for 60 minutes. Hold under vacuum at 80° C. for 60 minutes.

Cool sample tube to 30° C. and continue evacuation at 30° C. for 30 minutes. Close sample tube to vacuum pump and run leak test.

Evacuate sample tube at 30° C. for 30 minutes and hold for 30 minutes.

For a first CO analysis, CO uptakes are measured under static chemisorption conditions at 30° C. and starting manifold pressures of 50, 100, 150, 200, 250, 300, 350 and 400 mm Hg (gauge) to determine the total amount of CO adsorbed (i.e., both chemisorbed and physisorbed).

Pressurize manifold to the starting pressure (e.g., 50 mm Hg). Open valve between manifold and sample tube allowing CO to contact the sample in the sample tube. Allow the pressure in the sample tube to equilibrate. The reduction in pressure from the starting manifold pressure to equilibrium pressure in the sample tube indicates the volume of CO uptake by the sample.

Close valve between the manifold and sample tube and pressurize the manifold to the next starting pressure (e.g., 100 mm Hg). Open valve between manifold and sample tube allowing CO to contact the sample in the sample tube. Allow the pressure in the sample tube to equilibrate to determine the volume of CO uptake by the sample. Perform for each starting manifold pressure.

Evacuate sample tube at 30° C. for 30 minutes.

For a second CO analysis, CO uptakes are measured under static chemisorption conditions at 30° C. and starting manifold pressures of 50, 100, 150, 200, 250, 300, 350 and 400 mm Hg (gauge) as described above for the first CO analysis to determine the total amount of CO physisorbed.

Calculations:

Plot first and second analysis lines in each cycle: volume CO physically adsorbed and chemisorbed (1st analysis) and volume CO physically adsorbed (2nd analysis) (cm$^3$/g at STP) versus target CO pressures (mm Hg). Plot the difference between First and Second analysis lines at each target CO pressure. Extrapolate the difference line to its intercept with the Y-axis. In Cycle 1, total exposed Pt$_0$ (μmole CO/g)=Y-intercept of difference line/22.414×1000. In Cycle 2, total exposed Pt (μmole CO/g)=Y-intercept of difference line/22.414×1000.

Example 24

This example shows CO chemisorption results for various catalyst samples analyzed as described in Example 23. The results are shown in Table 15. Catalyst samples analyzed included:

(1) 5% Pt/0.5% Fe catalyst prepared in a manner similar to that described in one or more of the Examples provided herein (e.g., Examples 2 and 7), including heat treatment in a non-oxidizing environment at a maximum temperature of approximately 850° C.;

(2) 5% Pt/0.5% Fe catalyst prepared in a manner similar to that described in one or more of the Examples provided herein (e.g., Examples 2 and 7), including heat treatment in a non-oxidizing environment at a maximum temperature of approximately 950° C.; and (3) 5% Pt/0.5% Fe catalysts prepared as described in Example 22 (with and without water vapor introduction to the heat treatment atmosphere).

TABLE 15

| Catalyst | Initial Pt$_0$ (Cycle 1) (μmol CO/g) | Total Pt (Cycle 2) (μmol CO/g) |
|---|---|---|
| 5% Pt/0.5% Fe (maximum heat treatment temperature of approximately 850° C.) | 36.6 42.3 | 43.1 47 |
| 5% Pt/0.5% Fe (maximum heat treatment temperature of approximately 950° C.) | 17 | 23 |
| 5% Pt/1.5% Fe (Example 22, without water vapor) | 36 | 48.2 |
| 5% Pt/1.5% Fe (Example 22, with water vapor) | 19.2 | 29.1 |

Table 16 shows CO chemisorption results for various other catalyst samples analyzed as described in Example 23.

Catalyst samples analyzed included 4 5% Pt/0.5% Fe catalysts prepared in a manner similar to that described in one or more of the Examples provided herein (e.g., Examples 2 and 7), including heat treatment in a non-oxidizing environment at a maximum temperature of approximately 850° C., and 3 5% Pt/0.5% Fe catalysts prepared in essentially the same manner, but at a maximum heat treatment temperature of approximately 950° C.

TABLE 16

| Catalyst | Initial Pt$_0$ (Cycle 1) (μmol CO/g) | Total Pt (Cycle 2) (μmol CO/g) |
|---|---|---|
| 5% Pt/0.5% Fe (850° C.) | 33.3 | 28.8 |
| 5% Pt/0.5% Fe (850° C.) | 20.7 | 31 |
| 5% Pt/0.5% Fe (850° C.) | 15.5 | 22.7 |
|  | 17.7* | 21.5* |
| 5% Pt/0.5% Fe (850° C.) | 20.7 | 21.4 |
| 5% Pt/0.5% Fe (950° C.) | 24.4 | 27.7 |
| 5% Pt/0.5% Fe (950° C.) | 13.5 | 21.4 |
| 5% Pt/0.5% Fe (950° C.) | 17.3 | 18.8 |

*Replicate analysis.

Example 25

PMIDA oxidation was conducted under the conditions described in Example 3 using two different catalyst samples: a catalyst containing approximately 5% platinum and approximately 0.5% iron (5% Pt/0.5% Fe) prepared in a manner similar to that described in one or more of the Examples provided herein (e.g., Examples 2 and 7), including heat treatment in a non-oxidizing environment at a maximum temperature of approximately 850° C. and a 5% Pt/0.5% Fe catalyst prepared in essentially the same manner but at a maximum heat treatment temperature of approximately 950° C.

Each catalyst was tested in a run consisting of three 60 minute cycles. Using each catalyst, one cycle was conducted as described above in Example 3 while in the second and third cycles using each catalyst glycine was introduced to the reaction mixture at concentrations of 400 ppm and 800 ppm, respectively.

Figure 17:
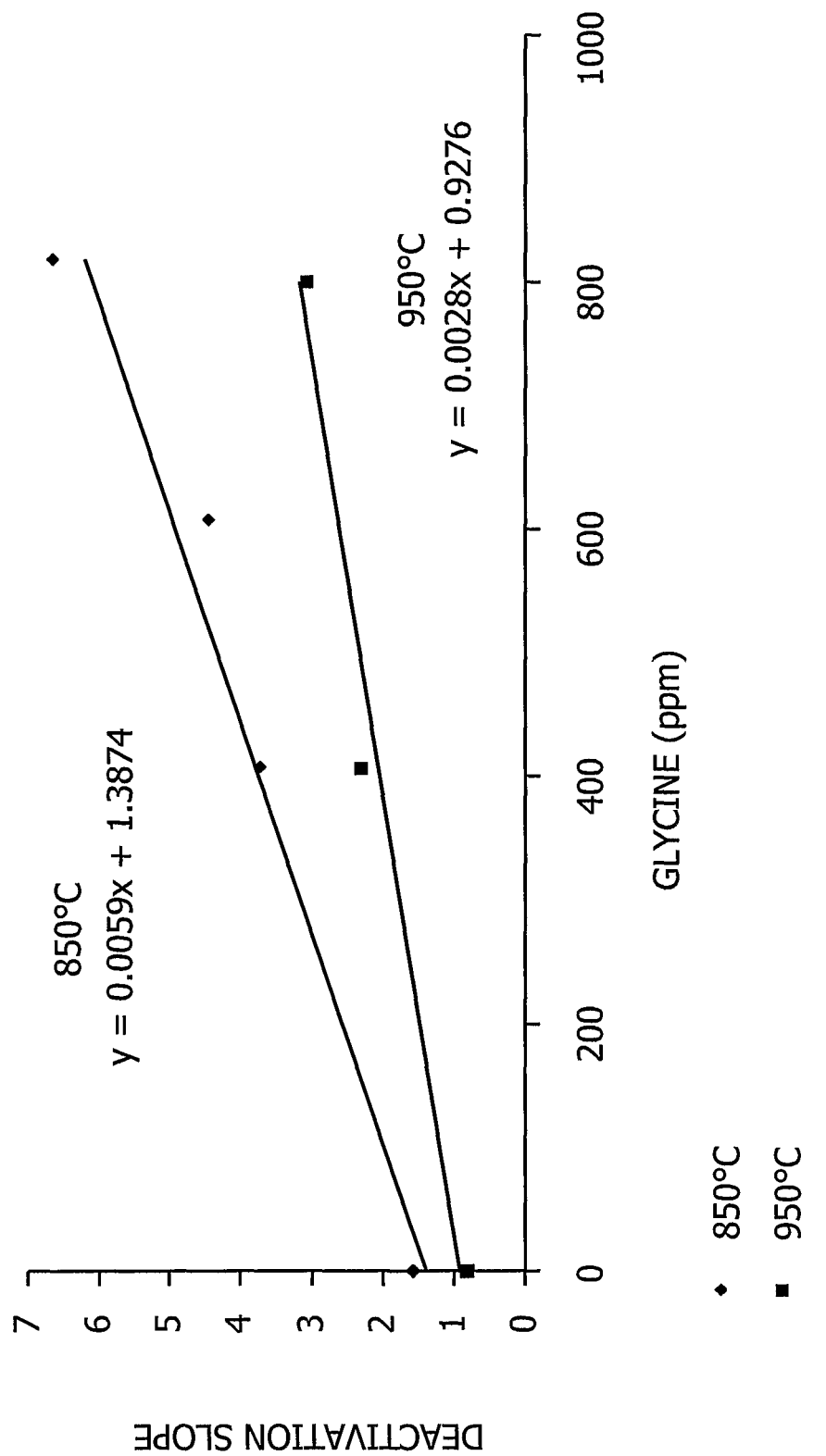
FIG. 17 shows the glycine index plot for catalysts prepared and used in N-(phosphonomethyl)iminodiacetic acid (PMIDA) oxidation as described in Example 24.

The time required to generate 1900 cm$^3$ of carbon dioxide (as determined by HPLC) in each cycle versus reaction cycle was plotted for each catalyst and the slope of this deactivation curve (i.e., the deactivation slope) was determined. The deactivation slope for each catalyst was plotted versus the concentration of glycine in the reaction mixture (0, 400, and 800 ppm); the slope of this curve is referred to herein as the glycine index. Increasing glycine index indicates increasing deactivation of the catalyst. These curves for each catalyst are shown in FIG. 17. As shown in FIG. 17, the catalyst prepared at a maximum heat treatment temperature of approximately 950° C. exhibited greater resistance to glycine-induced deactivation as indicated by a glycine index of approximately 0.0028 as compared to a glycine index of approximately 0.0059 for the catalyst prepared at a maximum heat treatment temperature of approximately 850° C.

Example 26

PMIDA oxidation was conducted under the conditions described in Example 3 using two different catalyst samples: a 5% Pt/0.5% Fe catalyst prepared in accordance with Example 20 (i.e., heat treatment at a maximum temperature of approximately 950° C.) and a 5% Pt/1% Fe catalyst prepared from a precursor prepared in accordance with Example 1 in accordance with Example 20 (i.e., heat treatment at a maximum temperature of approximately 950° C.).

Each catalyst was tested in three 60 minute cycles. Using each catalyst, one cycle was conducted as described in Example 3 while in the second and third cycles glycine was introduced to the reaction mixture at concentrations of 400 ppm and 800 ppm, respectively.

Figure 18:
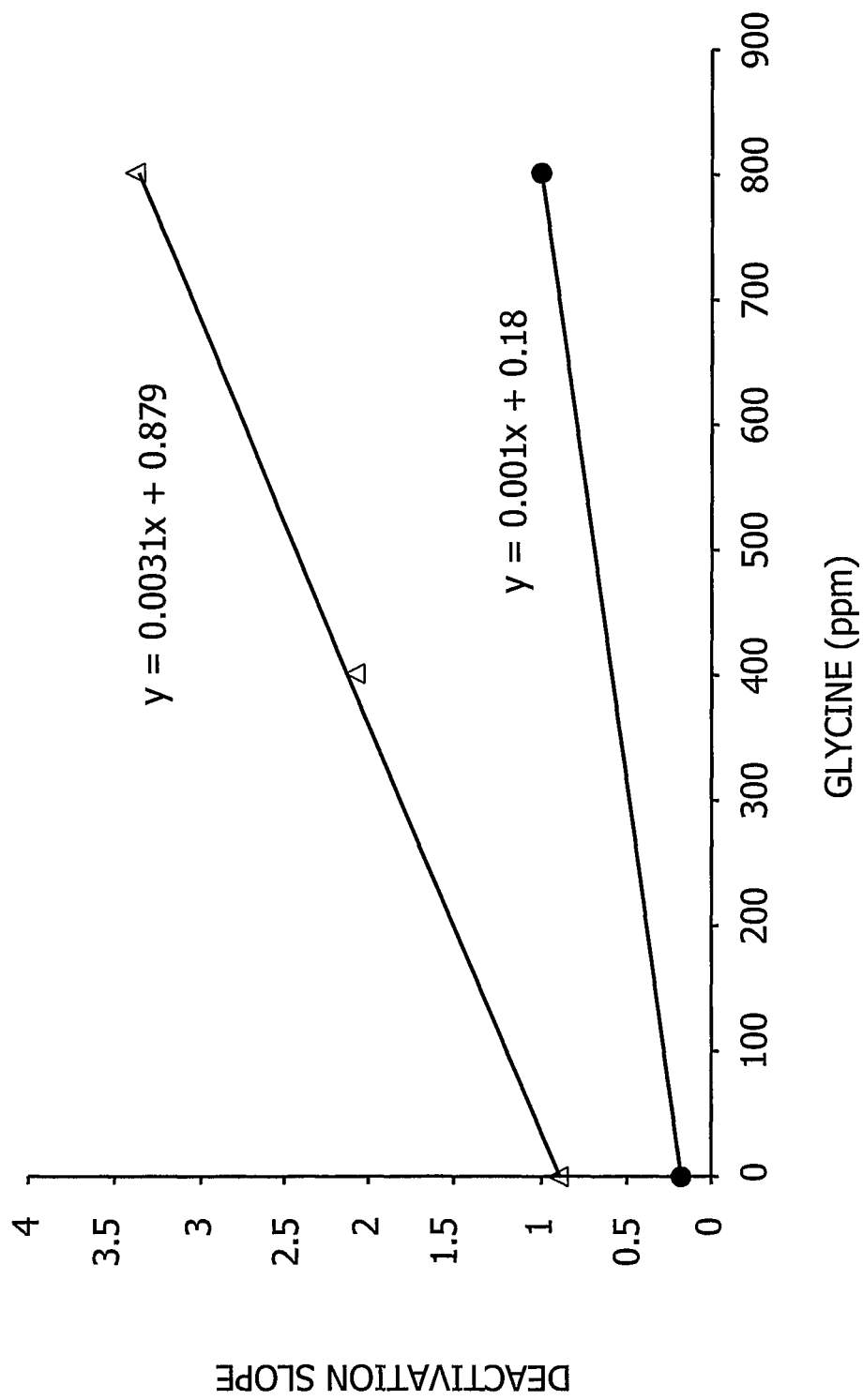
FIG. 18 shows the glycine index plot for catalysts prepared and used in N-(phosphonomethyl)iminodiacetic acid (PMIDA) oxidation as described in Example 25.

The glycine index for each catalyst was determined as described in Example 25. The results are shown in FIG. 18. The glcyine index for the 5% Pt/0.5% Fe catalyst was 0.0031 while the glycine index for the 5% Pt/1% Fe was 0.001, indicating reduced deactivation of the 5% Pt/1% Fe under the testing conditions.

Example 27

PMIDA oxidation was conducted under the conditions described in Example 3 over the course of 10 reaction cycles using each of two 5% Pt/0.5% Fe catalysts prepared in accordance with Example 20, including heat treatment at maximum temperatures of approximately 950° C. and 975° C., respectively.

Deactivation slopes were determined by plotting the time required to generate approximately 1900 cm$^3$ of carbon dioxide (determined by HPLC) versus reaction cycle. The time axis intercepts of the deactivation slopes were also determined.

Carbon dioxide generation during the 1st cycle and 9th cycle was determined using HPLC. IDA formation during the first reaction cycle was also determined using HPLC.

Platinum leaching during the first reaction cycle was determined using ICP analysis generally in accordance with Example 18.

The results are shown in Table 17.

TABLE 17

| Temp | Slope | Intercept (minutes) | CO$_2$ (1st Cycle) | CO$_2$ (9th Cycle) | IDA (9th Cycle) | Pt leaching (1st Cycle) (ppm) |
|---|---|---|---|---|---|---|
| 950° C. | 0.43 | 45.2 | 2159 | 2062 | 0.054 | 0.05 |
| 975° C. | 0.6 | 45.6 | 2133 | 2014 | 0.053 | 0.06 |

Example 28

This example details Small Angle X-ray Scattering (SAXS) results for catalysts prepared in accordance with the description herein.

Catalysts analyzed included two 5% Pt/0.5% Fe catalysts (1 and 1a) prepared in a manner similar to that described in one or more of the Examples provided herein (e.g., Examples 2 and 7), including heat treatment in a non-oxidizing environment at a maximum temperature of approximately 850° C., and two 5% Pt/0.5% Fe catalysts (2 and 2a) prepared in essentially the same manner, but at a maximum heat treatment temperature of approximately 950° C.

SAXS is a technique for studying structural features of nanoparticles. It is performed by focusing a low divergence x-ray beam onto a sample and observing a coherent scattering pattern that arises from electron density inhomogeneities within the sample. Since the dimensions typically analyzed are much larger than the wavelength of the typical x-ray used (e.g., 1.54 Å, for Cu), dimensions from tens to thousands of angstroms can be analyzed within a narrow angular scattering range. This angular range or pattern is analyzed using the inverse relationship between particle size and scattering angle to distinguish characteristic shape and size features within a given sample.

The instrument used for the SAXS analysis was the Rigaku Ultima III X-ray diffraction and/or scattering system configured with a line source for standard and high-resolution materials analysis. The system has variable slits, which are ideal for low angle diffraction or scattering. The stages include a six position sample changer, thin-film stage and a small-angle transmission stage. A two-bounce germanium monochromator makes the system suitable for high resolution rocking curves and reflectivity, and a multilayer mirror for grazing incident studies or reflectomatry can also condition the incident beam. For the SAXS analysis, the X-ray is generated from a copper target operated at 40 kV and 100 mA, and the irradiated area is approximately 100 mm$^2$. The scanning speed of the X-ray beam is 0.1 degree per minute. The dry catalyst powder can be directly analyzed and no special sample preparation is required.

Figure 21:
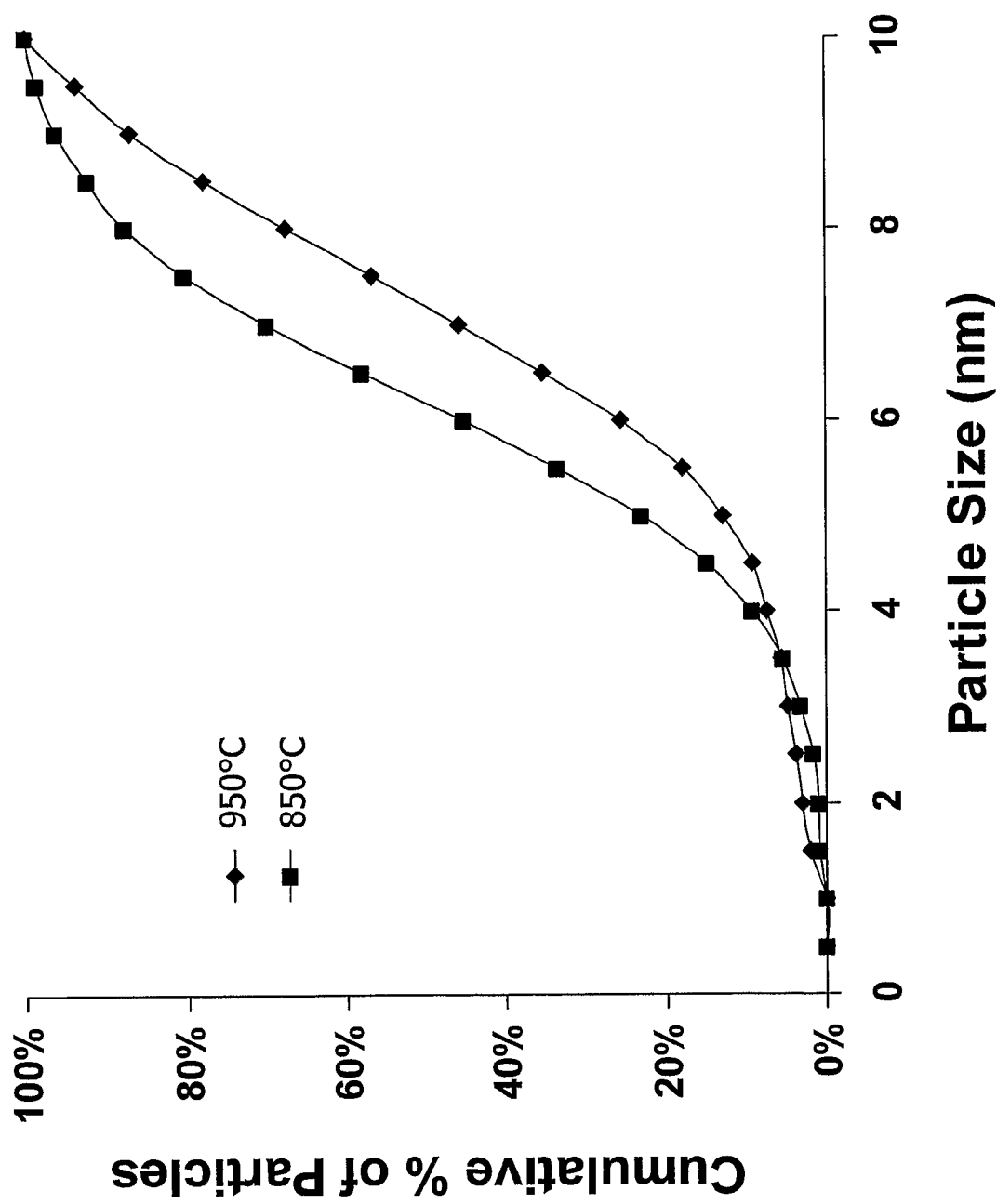
FIG. 21 shows the cumulative percentage of metal particles analyzed as described in Example 20 versus particle size.
Figure 22:
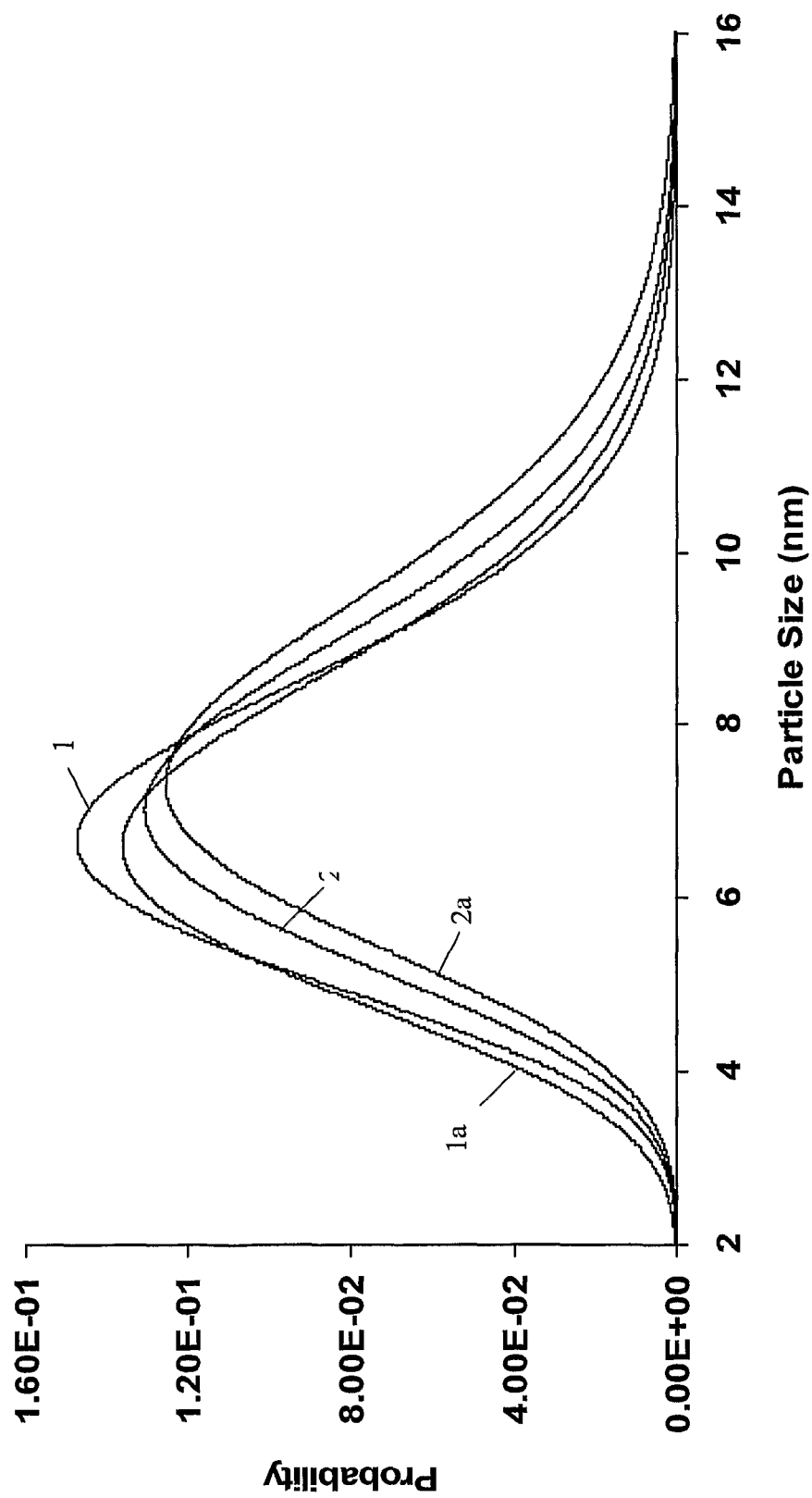
FIG. 22 shows Small Angle X-ray Scattering (SAXS) results for catalysts analyzed as described in Example 28.

FIG. 21 is a plot showing the particle size distributions of the samples analyzed. As shown, catalysts prepared at a higher heat treatment temperature (2 and 2a) generally contained a reduced portion of smaller particles than the catalysts prepared at the lower heat treatment temperature (1 and 1a). The maximum particle sizes (i.e., peaks of particle size distribution curves) and average particle sizes are summarized in Table 18.

TABLE 18

| Sample | Peak of curve (nm) | Average particle size (nm) |
|---|---|---|
| 1: 5% Pt/0.5% Fe (850° C.) | 6.67 | 7.13 |
| 1a: 5% Pt/0.5% Fe (850° C.) | 6.61 | 7.15 |
| 2: 5% Pt/0.5% Fe (950° C.) | 7.02 | 7.54 |
| 2a: 5% Pt/0.5% Fe (950° C.) | 7.33 | 7.88 |

Example 29

This example describes use of various catalysts containing platinum and cobalt or platinum, iron and cobalt deposited on a carbon support prepared generally in accordance with the disclosure herein (e.g., Examples 2 and 7) in PMIDA oxidation. Catalysts having varied platinum, cobalt and/or iron contents and/or heat treated at different heat treatment temperatures were prepared and used to catalyze PMIDA oxidation. The compositions of the catalysts and maximum heat treatment temperatures are summarized in Table 19.

TABLE 19

| Catalyst | Heat Treatment Temp. (° C.) |
|---|---|
| 4.86% Pt/0.47% Co | 850° C. |
| 4.78% Pt/0.24% Co | 900° C. |
| 5% Pt/0.25% Co* | 950° C. |
| 4.8% Pt/0.25% Fe/0.23% Co | 850° C. |
| 4.63% Pt/0.24% Fe/0.24% Co | 900° C. |
| 5% Pt/0.1% Fe/0.4% Co* | 850° C. |
| 4.89% Pt/0.19% Fe/0.39% Co | 900° C. |
| 5% Pt/0.22% Fe/0.4% Co | 950° C. |
| 4.8% Pt/0.41% Fe/0.097% Co | 850° C. |
| 4.82% Pt/0.5% Fe/0.09% Co | 850° C. |
| 4.96% Pt/0.11% Fe/0.44% Co | 850° C. |
| 4.86% Pt/0.76% Fe/0.22% Co | 850° C. |
| 4.96% Pt/0.32% Fe/0.2% Co | 900° C. |

*Not determined, approximate.

The PMIDA oxidation was conducted in a tube reactor containing a total reaction mass (180 g) which included deionized water (164.3 g), 8.2% by weight PMIDA (14.8 g) and 0.5% by weight catalyst (0.9 g). The oxidation was conducted at a temperature of approximately 90° C., a pressure of approximately 65 psig, and an oxygen flow rate of approximately 72 cm$^3$/minute. The reaction mixture was agitated at a stir rate of approximately 900 revolutions per minute (rpm).

The catalyst was tested during each of six runs. Each reaction run was allowed to proceed until at least approximately 95% of the PMIDA was consumed.

The results of PMIDA oxidation using each catalyst, including the contents of the reaction mixtures (e.g., % by weight PMIDA and % by weight Glyphosate product), as determined by HPLC, are summarized in Tables 20-32.

TABLE 20

4.86% Pt/0.47% Co catalyst prepared by heat treatment at a maximum temperature of 850° C.

| | Run | | | | | |
|---|---|---|---|---|---|---|
| | 1 | 2 | 3 | 4 | 5 | 6 |
| Run Time (minutes) | 43.7 | 44.1 | 44.2 | 43.2 | 44.2 | 43.1 |
| Glyphosate (% by weight) | 5.398 | 5.604 | 5.611 | 5.722 | 5.726 | 5.711 |
| PMIDA (% by weight) | 0.004 | 0.006 | 0.003 | 0.005 | 0.005 | 0.004 |
| HCHO (% by weight) | 0.031 | 0.030 | 0.025 | 0.032 | 0.036 | 0.040 |
| HCOOH (% by weight) | 0.089 | 0.087 | 0.082 | 0.099 | 0.092 | 0.110 |
| IDA (% by weight) | 0.169 | 0.092 | 0.066 | 0.052 | 0.047 | 0.041 |
| Platinum (ppm) | 0.09 | 0.08 | | | | 0.09 |
| Cobalt (ppm) | 7.99 | 0.49 | | | | 0.14 |
| Platinum lost (%) | 0.036% | 0.032% | | | | 0.036% |
| Cobalt lost (%) | 31.96% | 1.96% | | | | 0.56% |

TABLE 21

4.78% Pt/0.24% Co catalyst prepared by heat treatment at a maximum temperature of 900° C.

| | Run | | | | | |
|---|---|---|---|---|---|---|
| | 1 | 2 | 3 | 4 | 5 | 6 |
| Run Time (minutes) | 42.1 | 41.6 | 42.8 | 42.5 | 41.6 | 41.6 |
| Glyphosate (% by weight) | 5.382 | 5.715 | 5.686 | 5.717 | 5.757 | 5.671 |
| PMIDA (% by weight) | 0.006 | 0.004 | 0.002 | 0.003 | 0.005 | 0.003 |
| HCHO (% by weight) | 0.023 | 0.025 | 0.034 | 0.031 | 0.033 | 0.031 |
| HCOOH (% by weight) | 0.173 | 0.200 | 0.206 | 0.208 | 0.224 | 0.231 |
| IDA (% by weight) | 0.098 | 0.051 | 0.042 | 0.040 | 0.036 | 0.033 |
| Platinum (ppm) | 0.04 | 0.08 | | | | 0.06 |

TABLE 21-continued 4.78% Pt/0.24% Co catalyst prepared by heat treatment at a maximum temperature of 900° C.

| | Run | | | | | |
|---|---|---|---|---|---|---|
| | 1 | 2 | 3 | 4 | 5 | 6 |
| Cobalt (ppm) | 1.73 | 0.30 | | | | 0.06 |
| Platinum lost (%) | 0.02 | 0.03 | | | | 0.02 |
| Cobalt lost (%) | 13.8 | 2.4 | | | | 0.5 |

TABLE 22

5% Pt/0.25% Co catalyst prepared by heat treatment at a maximum temperature of 950° C.

| | Run | | | | | |
|---|---|---|---|---|---|---|
| | 1 | 2 | 3 | 4 | 5 | 6 |
| Run Time (minutes) | 41.8 | 41.4 | 41.6 | 41.8 | 42.1 | 42.0 |
| Glyphosate (% by weight) | 5.650 | 5.717 | 5.797 | 5.739 | 5.785 | 5.768 |
| PMIDA (% by weight) | 0.001 | ND | ND | ND | ND | ND |
| HCHO (% by weight) | 1.649 | 1.573 | 1.628 | 1.689 | 1.756 | 1.618 |
| HCOOH (% by weight) | 0.401 | 0.436 | 0.438 | 0.428 | 0.449 | 0.441 |
| IDA (% by weight) | 0.051 | 0.030 | 0.026 | 0.026 | 0.024 | 0.023 |
| Platinum (ppm) | 0.05 | 0.05 | | | | 0.06 |
| Cobalt (ppm) | 1.67 | 0.21 | | | | 0.06 |
| Platinum lost (%) | 0.02 | 0.02 | | | | 0.024 |
| Cobalt lost (%) | 13.36 | 1.68 | | | | 0.48 |

ND = not detected.

TABLE 23

4.8% Pt/0.25% Fe/0.23% Co catalyst prepared by heat treatment at a maximum temperature of 850° C.

| | Run | | | | | |
|---|---|---|---|---|---|---|
| | 1 | 2 | 3 | 4 | 5 | 6 |
| Run Time (minutes) | 41.8 | 42.4 | 42.2 | 42.6 | 42.4 | 41.2 |
| Glyphosate (% by weight) | 5.310 | 5.590 | 5.600 | 5.690 | 5.700 | 5.470 |
| PMIDA (% by weight) | 0.005 | 0.005 | 0.003 | 0.002 | 0.006 | 0.009 |
| HCHO (% by weight) | 0.018 | 0.019 | 0.015 | 0.045 | 0.030 | 0.033 |
| HCOOH (% by weight) | 0.100 | 0.109 | 0.148 | 0.126 | 0.158 | 0.135 |
| IDA (% by weight) | 0.168 | 0.083 | 0.072 | 0.061 | 0.058 | 0.043 |
| Platinum (ppm) | 0.09 | 0.09 | | | | 0.10 |
| Iron (ppm) | 2.50 | 0.30 | | | | <0.3 |
| Cobalt (ppm) | 5.04 | 0.38 | | | | 0.06 |
| Platinum lost (%) | 0.036 | 0.036 | | | | 0.04 |
| Iron lost (%) | 20 | 2.4 | | | | <0.48 |
| Cobalt lost (%) | 40.32 | 3.04 | | | | 0.48 |

TABLE 24

4.63% Pt/0.24% Fe/0.24% Co catalyst prepared by heat treatment at a maximum temperature of 900° C.

| | Run | | | | | |
|---|---|---|---|---|---|---|
| | 1 | 2 | 3 | 4 | 5 | 6 |
| Run Time (minutes) | 42.5 | 41.5 | 41.3 | 42.4 | 41.1 | 42.0 |
| Glyphosate (% by weight) | 5.433 | 5.650 | 5.774 | 5.729 | 5.719 | 5.759 |
| PMIDA (% by weight) | DBNQ | 0.004 | 0.003 | 0.002 | 0.004 | 0.004 |
| HCHO (% by weight) | 0.042 | 0.047 | 0.054 | 0.047 | 0.050 | 0.058 |
| HCOOH (% by weight) | 0.148 | 0.189 | 0.198 | 0.193 | 0.218 | 0.227 |
| IDA (% by weight) | 0.113 | 0.058 | 0.053 | 0.054 | 0.046 | 0.042 |
| Platinum (ppm) | 0.05 | 0.05 | | | | 0.07 |
| Iron (ppm) | 1.60 | 0.30 | | | | <0.3 |
| Cobalt (ppm) | 3.960 | 0.300 | | | | 0.06 |
| Platinum lost (%) | 0.02 | 0.02 | | | | 0.028 |
| Iron lost (%) | 12.8 | 2.4 | | | | <2.4 |
| Cobalt lost (%) | 31.68 | 2.4 | | | | 0.48 |

DBNQ = Detected but not quantified.

TABLE 25

5% Pt/0.1% Fe/0.4% Co catalyst prepared by heat treatment at a maximum temperature of 850° C.

| | Run | | | | | |
|---|---|---|---|---|---|---|
| | 1 | 2 | 3 | 4 | 5 | 6 |
| Run Time (minutes) | 40.6 | 40.5 | 40.4 | 41.7 | 40.8 | 40.9 |
| Glyphosate (% by weight) | 5.316 | 5.507 | 5.636 | 5.633 | 5.737 | 5.639 |
| PMIDA (% by weight) | 0.003 | 0.004 | 0.003 | 0.003 | 0.003 | 0.003 |
| HCHO (% by weight) | 0.027 | 0.030 | 0.031 | 0.042 | 0.028 | 0.033 |
| HCOOH (% by weight) | 0.159 | 0.186 | 0.193 | 0.221 | 0.218 | 0.240 |
| IDA (% by weight) | 0.154 | 0.084 | 0.073 | 0.065 | 0.060 | 0.055 |
| Platinum (ppm) | 0.02 | 0.05 | | | | 0.05 |
| Iron (ppm) | 0.8 | <0.3 | | | | 2.5 |
| Cobalt (ppm) | 5.34 | 0.46 | | | | 0.10 |
| Platinum lost (%) | 0.008 | 0.02 | | | | 0.02 |
| Iron lost (%) | 16 | <6.0 | | | | 50 |
| Cobalt lost (%) | 26.7 | 2.3 | | | | 0.5 |

TABLE 26

4.89% Pt/0.19% Fe/0.39% Co catalyst prepared by heat treatment at a maximum temperature of 900° C.

| | Run | | | | | |
|---|---|---|---|---|---|---|
| | 1 | 2 | 3 | 4 | 5 | 6 |
| Run Time (minutes) | 41.9 | 42.7 | 41.9 | 43.0 | 42.0 | 42.0 |
| Glyphosate (% by weight) | 5.417 | 5.545 | 5.572 | 5.626 | 5.619 | 5.658 |

TABLE 26-continued 4.89% Pt/0.19% Fe/0.39% Co catalyst prepared by heat treatment at a maximum temperature of 900° C.

| | Run | | | | | |
|---|---|---|---|---|---|---|
| | 1 | 2 | 3 | 4 | 5 | 6 |
| PMIDA (% by weight) | 0.004 | 0.002 | 0.002 | 0.001 | 0.002 | 0.003 |
| HCHO (% by weight) | 0.027 | 0.023 | 0.022 | 0.041 | 0.028 | 0.034 |
| HCOOH (% by weight) | 0.104 | 0.103 | 0.109 | 0.121 | 0.116 | 0.134 |
| IDA (% by weight) | 0.131 | 0.093 | 0.084 | 0.075 | 0.076 | 0.070 |
| Platinum (ppm) | 0.03 | 0.02 | | | | 0.04 |
| Iron (ppm) | 0.80 | 1.00 | | | | <0.3 |
| Cobalt (ppm) | 4.48 | 0.32 | | | | 0.060 |
| Platinum lost (%) | 0.012 | 0.008 | | | | 0.016 |
| Iron lost (%) | 16 | 20 | | | | <6.0 |
| Cobalt lost (%) | 22.4 | 1.6 | | | | 0.3 |

TABLE 27

5% Pt/0.22% Fe/0.4% Co catalyst prepared by heat treatment at a maximum temperature of 950° C.

| | Run | | | | | |
|---|---|---|---|---|---|---|
| | 1 | 2 | 3 | 4 | 5 | 6 |
| Run Time (minutes) | 42.6 | 42.5 | 42.8 | 42.7 | 42.7 | 42.2 |
| Glyphosate (% by weight) | 5.635 | 5.658 | 5.710 | 5.718 | 5.754 | 5.730 |
| PMIDA (% by weight) | 0.003 | 0.002 | 0.002 | 0.002 | 0.002 | 0.002 |
| HCHO (% by weight) | 0.055 | 0.045 | 0.039 | 0.050 | 0.060 | 0.046 |
| HCOOH (% by weight) | 0.209 | 0.233 | 0.225 | 0.259 | 0.260 | 0.239 |
| IDA (% by weight) | 0.089 | 0.057 | 0.049 | 0.042 | 0.040 | 0.039 |
| Platinum (ppm) | 0.04 | 0.02 | | | | 0.03 |
| Iron (ppm) | 0.70 | 0.30 | | | | <0.3 |
| Cobalt (ppm) | 3.38 | 0.35 | | | | 0.09 |
| Platinum lost (%) | 0.016 | 0.008 | | | | 0.012 |
| Iron lost (%) | 14 | 6 | | | | <6.0 |
| Cobalt lost (%) | 16.9 | 1.75 | | | | 0.45 |

TABLE 28

4.8% Pt/0.41% Fe/0.097% Co catalyst prepared by heat treatment at a maximum temperature of 850° C.

| | Run | | | | | |
|---|---|---|---|---|---|---|
| | 1 | 2 | 3 | 4 | 5 | 6 |
| Run Time (minutes) | 43.5 | 42.0 | 42.9 | 42.1 | 41.9 | 41.8 |
| Glyphosate (% by weight) | 5.378 | 5.684 | 5.678 | 5.715 | 5.902 | 5.620 |
| PMIDA (% by weight) | 0.002 | 0.003 | 0.003 | 0.005 | 0.004 | 0.003 |
| HCHO (% by weight) | 0.020 | 0.020 | 0.020 | 0.021 | 0.025 | 0.023 |
| HCOOH (% by weight) | 0.094 | 0.107 | 0.110 | 0.129 | 0.140 | 0.137 |
| IDA (% by weight) | 0.180 | 0.085 | 0.082 | 0.065 | 0.056 | 0.060 |
| Platinum (ppm) | 0.07 | 0.07 | | | | 0.10 |
| Iron (ppm) | 4.50 | 0.50 | | | | <0.3 |
| Cobalt (ppm) | 2.37 | 0.14 | | | | 0.02 |
| Platinum lost (%) | 0.028 | 0.028 | | | | 0.04 |
| Iron lost (%) | 22.5 | 2.5 | | | | <1.5 |
| Cobalt lost (%) | 47.4 | 2.8 | | | | 0.4 |

TABLE 29

4.82% Pt/0.5% Fe/0.09% Co catalyst prepared by heat treatment at a maximum temperature of 850° C.

| | Run | | | | | |
|---|---|---|---|---|---|---|
| | 1 | 2 | 3 | 4 | 5 | 6 |
| Run Time (minutes) | 41.9 | 42.2 | 43.2 | 42.6 | 42.5 | 41.8 |
| Glyphosate (% by weight) | 5.195 | 5.463 | 5.542 | 5.519 | 5.635 | 5.610 |
| PMIDA (% by weight) | DBNQ | 0.003 | 0.003 | 0.004 | 0.002 | 0.003 |
| HCHO (% by weight) | 0.014 | 0.009 | 0.010 | 0.008 | 0.025 | 0.015 |
| HCOOH (% by weight) | 0.073 | 0.075 | 0.090 | 0.087 | 0.111 | 0.104 |
| IDA (% by weight) | 0.193 | 0.095 | 0.077 | 0.068 | 0.061 | 0.059 |
| Platinum (ppm) | 0.04 | 0.03 | | | | 0.10 |
| Iron (ppm) | 6.70 | 0.90 | | | | <0.3 |
| Cobalt (ppm) | 2.53 | 0.14 | | | | 0.02 |
| Platinum lost (%) | 0.016 | 0.012 | | | | 0.04 |
| Iron lost (%) | 26.8 | 3.6 | | | | <1.2 |
| Cobalt lost (%) | 50.6 | 2.8 | | | | 0.4 |

DBNQ = Detected but not quantified.

TABLE 30

4.96% Pt/0.11% Fe/0.44% Co catalyst prepared by heat treatment at a maximum temperature of 850° C.

| | Run | | | | | |
|---|---|---|---|---|---|---|
| | 1 | 2 | 3 | 4 | 5 | 6 |
| Run Time (minutes) | 41.8 | 42.5 | 42.4 | 42.5 | 42.1 | 42.8 |
| Glyphosate (% by weight) | 5.573 | 5.560 | 5.598 | 5.500 | 5.693 | 5.627 |
| PMIDA (% by weight) | 0.001 | 0.002 | 0.002 | 0.004 | 0.003 | 0.005 |
| HCHO (% by weight) | 0.038 | 0.038 | 0.026 | 0.018 | 0.014 | 0.012 |
| HCOOH (% by weight) | 0.105 | 0.122 | 0.118 | 0.122 | 0.128 | 0.127 |
| IDA (% by weight) | 0.176 | 0.098 | 0.093 | 0.076 | 0.068 | 0.060 |
| Platinum (ppm) | 0.06 | 0.08 | | | | 0.08 |
| Iron (ppm) | 0.9 | <0.3 | | | | <0.3 |

TABLE 30-continued 4.96% Pt/0.11% Fe/0.44% Co catalyst prepared by heat treatment at a maximum temperature of 850° C.

| | Run | | | | | |
|---|---|---|---|---|---|---|
| | 1 | 2 | 3 | 4 | 5 | 6 |
| Cobalt (ppm) | 6.88 | 0.62 | | | | 0.14 |
| Platinum lost (%) | 0.024 | 0.032 | | | | 0.032 |
| Iron lost (%) | 18 | <6.0 | | | | <6.0 |
| Cobalt lost (%) | 27.52 | 2.48 | | | | 0.56 |

TABLE 31

4.86% Pt/0.76% Fe/0.22% Co catalyst prepared by heat treatment at a maximum temperature of 850° C.

| | Run | | | | | |
|---|---|---|---|---|---|---|
| | 1 | 2 | 3 | 4 | 5 | 6 |
| Run Time (minutes) | 43.2 | 44.4 | 44.0 | 43.8 | 44.2 | 45.0 |
| Glyphosate (% by weight) | 5.096 | 5.465 | 5.522 | 5.623 | 5.696 | 5.798 |
| PMIDA (% by weight) | 0.001 | 0.004 | 0.005 | 0.007 | 0.010 | 0.010 |
| HCHO (% by weight) | 0.026 | 0.005 | 0.007 | 0.019 | 0.017 | 0.031 |
| HCOOH (% by weight) | 0.067 | 0.055 | 0.057 | 0.072 | 0.063 | 0.085 |
| IDA (% by weight) | 0.332 | 0.176 | 0.132 | 0.096 | 0.060 | 0.047 |
| Platinum (ppm) | 0.15 | 0.1 | | | | 0.09 |
| Iron (ppm) | 12.9 | 1.4 | | | | 0.6 |
| Cobalt (ppm) | 6.7 | 0.38 | | | | 0.06 |
| Platinum lost (%) | 0.06 | 0.04 | | | | 0.04 |
| Iron lost (%) | 34.4 | 3.7 | | | | 1.6 |
| Cobalt lost (%) | 53.6 | 3.0 | | | | 0.48 |

TABLE 32

4.96% Pt/0.32% Fe/0.2% CO catalyst prepared by heat treatment at a maximum temperature of 900° C.

| | Run | | | | | |
|---|---|---|---|---|---|---|
| | 1 | 2 | 3 | 4 | 5 | 6 |
| Run Time (minutes) | 40.9 | 41.1 | 42.2 | 41.6 | 41.7 | 41.6 |
| Glyphosate (% by weight) | 5.644 | 5.624 | 5.809 | 5.728 | 5.794 | 5.801 |
| PMIDA (% by weight) | 0.003 | 0.001 | 0.001 | 0.002 | 0.002 | 0.002 |
| HCHO (% by weight) | 0.060 | 0.058 | 0.059 | 0.062 | 0.060 | 0.059 |
| HCOOH (% by weight) | 0.249 | 0.287 | 0.273 | 0.293 | 0.299 | 0.322 |
| IDA (% by weight) | 0.074 | 0.045 | 0.040 | 0.035 | 0.033 | 0.029 |
| Platinum (ppm) | 0.04 | 0.03 | | | | 0.05 |
| Iron (ppm) | 1.10 | 1.30 | | | | <0.3 |
| Cobalt (ppm) | 2.04 | 0.19 | | | | 0.04 |
| Platinum lost (%) | 0.016 | 0.012 | | | | 0.02 |
| Iron lost (%) | 11 | 13 | | | | <3.0 |
| Cobalt lost (%) | 20.4 | 1.9 | | | | 0.4 |

Based on the above results, IDA production and the total amount of iron and cobalt of the catalyst appear to be directly related (i.e., lower total iron and cobalt contents tend to produce lower amounts of IDA).

Example 30

This example describes use of various catalysts containing platinum and cobalt or platinum, iron and cobalt deposited on a carbon support prepared generally in accordance with the disclosure herein (e.g., Examples 2 and 7) in PMIDA oxidation. Catalysts having varied platinum, cobalt and/or iron contents and/or heat treated at different heat treatment temperatures were prepared and used to catalyze PMIDA oxidation. The compositions of the catalysts and maximum heat treatment temperatures are summarized in Table 33.

TABLE 33

| Catalyst | Heat Treatment Temp. (° C.) |
|---|---|
| 5.03% Pt/0.27% Co | 850° C. |
| 5% Pt/0.5% Fe/0.1% Co* | 850° C. |
| 4.82% Pt/0.49% Fe/0.093% Co | 850° C. |
| 4.87% Pt/0.11% Fe/0.37% Co | 850° C. |
| 5.17% Pt/0.13% Fe/0.42% Co | 850° C. |
| 5.03% Pt/0.11% Fe/0.39% Co | 950° C. |
| 4.98% Pt/0.11% Fe/0.39% Co | 950° C. |
| 5% Pt/0.1% Fe/0.4% Co* | 950° C. |
| 5.01% Pt/0.12% Fe/0.47% Co | 850° C. |
| 4.92% Pt/0.11% Fe/0.51% Co | 950° C. |
| 4.88% Pt/0.26% Fe/0.27% Co | 850° C. |
| 4.97% Pt/0.27% Fe/0.18% Co | 950° C. |
| 4.93% Pt/0.11% Fe/0.09% Co | 850° C. |

*Not determined, approximate.

Each of the catalysts described in Table 33 were used to catalyze PMIDA oxidation under the conditions described in Example 29. The results of PMIDA oxidation using each catalyst, including the contents of the reaction mixtures, are summarized in Tables 34-46.

TABLE 34

5.03% Pt/0.27% Co catalyst prepared by heat treatment at a maximum temperature of 850° C.

| | Run | | | | | |
|---|---|---|---|---|---|---|
| | 1 | 2 | 3 | 4 | 5 | 6 |
| Run Time (minutes) | 42.0 | 42.0 | 42.1 | 42.3 | 41.9 | 41.7 |
| Glyphosate (% by weight) | 5.739 | 5.768 | 5.772 | 5.759 | 5.800 | 5.819 |
| PMIDA (% by weight) | 0.003 | 0.003 | 0.003 | 0.002 | 0.002 | 0.002 |
| HCHO (% by weight) | 0.051 | 0.053 | 0.053 | 0.059 | 0.060 | 0.064 |
| HCOOH (% by weight) | 0.223 | 0.268 | 0.264 | 0.269 | 0.273 | 0.277 |
| IDA (% by weight) | 0.048 | 0.029 | 0.026 | 0.024 | 0.022 | 0.021 |
| Platinum (ppm) | 0.07 | 0.06 | | | | 0.06 |
| Cobalt (ppm) | 1.36 | 0.19 | | | | 0.05 |
| Platinum lost (%) | 0.03 | 0.02 | | | | 0.02 |
| Cobalt lost (%) | 10.88 | 1.52 | | | | 0.4 |

TABLE 35

5% Pt/0.5% Fe/0.1% Co catalyst prepared by heat treatment at a maximum temperature of 850° C.

| | Run | | | | | |
|---|---|---|---|---|---|---|
| | 1 | 2 | 3 | 4 | 5 | 6 |
| Run Time (minutes) | 43.0 | 42.3 | 42.6 | 45.4 | 43.5 | 42.9 |
| Glyphosate (% by weight) | 5.560 | 5.680 | 5.700 | 5.700 | 5.690 | 5.740 |
| PMIDA (% by weight) | 0.002 | 0.006 | 0.005 | 0.003 | 0.006 | 0.005 |
| HCHO (% by weight) | 0.039 | 0.034 | 0.024 | 0.026 | 0.027 | 0.029 |
| HCOOH (% by weight) | 0.130 | 0.139 | 0.148 | 0.142 | 0.153 | 0.151 |
| IDA (% by weight) | 0.113 | 0.073 | 0.055 | 0.059 | 0.052 | 0.050 |
| Platinum (ppm) | 0.08 | 0.06 | | | | 0.05 |
| Iron (ppm) | 6.7 | 0.8 | | | | 0.3 |
| Cobalt (ppm) | 1.67 | 0.09 | | | | 0.02 |
| Platinum lost (%) | 0.032 | 0.024 | | | | 0.02 |
| Iron lost (%) | 26.8 | 3.2 | | | | 1.2 |
| Cobalt lost (%) | 33.4 | 1.8 | | | | 0.4 |

TABLE 36

4.82% Pt/0.49% Fe/0.093% Co catalyst prepared by heat treatment at a maximum temperature of 850° C.

| | Run | | | | | |
|---|---|---|---|---|---|---|
| | 1 | 2 | 3 | 4 | 5 | 6 |
| Run Time (minutes) | 42.5 | 43.6 | 43.4 | 42.9 | 43.0 | 43.9 |
| Glyphosate (% by weight) | 5.388 | 5.569 | 5.604 | 5.662 | 5.643 | 5.720 |
| PMIDA (% by weight) | 0.003 | 0.004 | 0.003 | 0.007 | 0.006 | 0.003 |
| HCHO (% by weight) | 0.026 | 0.024 | 0.014 | 0.016 | 0.012 | 0.024 |
| HCOOH (% by weight) | 0.147 | 0.145 | 0.135 | 0.142 | 0.139 | 0.144 |
| IDA (% by weight) | 0.141 | 0.083 | 0.083 | 0.070 | 0.062 | 0.063 |
| Platinum (ppm) | 0.03 | 0.07 | | | | 0.06 |
| Iron (ppm) | 6.7 | 1.2 | | | | <0.3 |
| Cobalt (ppm) | 2.03 | 0.13 | | | | 0.02 |
| Platinum lost (%) | 0.012 | 0.028 | | | | 0.024 |
| Iron lost (%) | 26.8 | 4.8 | | | | <1.2 |
| Cobalt lost (%) | 40.6 | 2.6 | | | | 0.4 |

TABLE 37

4.87% Pt/0.11% Fe/0.37% Co catalyst prepared by heat treatment at a maximum temperature of 850° C.

| | Run | | | | | |
|---|---|---|---|---|---|---|
| | 1 | 2 | 3 | 4 | 5 | 6 |
| Run Time (minutes) | 41.9 | 41.6 | 42.4 | 41.6 | 41.6 | 41.1 |
| Glyphosate (% by weight) | 5.617 | 5.746 | 5.825 | 5.720 | 5.774 | 5.774 |
| PMIDA (% by weight) | 0.003 | 0.003 | 0.002 | 0.004 | 0.004 | 0.003 |
| HCHO (% by weight) | 0.035 | 0.027 | 0.036 | 0.027 | 0.026 | 0.026 |
| HCOOH (% by weight) | 0.181 | 0.192 | 0.198 | 0.201 | 0.213 | 0.211 |
| IDA (% by weight) | 0.078 | 0.047 | 0.044 | 0.041 | 0.035 | 0.034 |
| Platinum (ppm) | 0.07 | 0.05 | | | | 0.05 |
| Iron (ppm) | 1.20 | 0.40 | | | | 0.50 |
| Cobalt (ppm) | 4.50 | 0.51 | | | | 0.14 |
| Platinum lost (%) | 0.03 | 0.02 | | | | 0.02 |
| Iron lost (%) | 24 | 8 | | | | 10 |
| Cobalt lost (%) | 22.5 | 2.55 | | | | 0.7 |

TABLE 38

5.17% Pt/0.13% Fe/0.42% Co catalyst prepared by heat treatment at a maximum temperature of 850° C.

| | Run | | | | | |
|---|---|---|---|---|---|---|
| | 1 | 2 | 3 | 4 | 5 | 6 |
| Run Time (minutes) | 40.5 | 40.4 | 40.4 | 40.9 | 41.1 | 41.0 |
| Glyphosate (% by weight) | 5.380 | 5.560 | 5.570 | 5.570 | 5.590 | 5.580 |
| PMIDA (% by weight) | 0.003 | 0.002 | 0.003 | 0.003 | 0.002 | 0.002 |
| HCHO (% by weight) | 0.049 | 0.053 | 0.060 | 0.043 | 0.048 | 0.045 |
| HCOOH (% by weight) | 0.215 | 0.242 | 0.253 | 0.237 | 0.258 | 0.253 |
| IDA (% by weight) | 0.084 | 0.054 | 0.049 | 0.046 | 0.041 | 0.038 |
| Platinum (ppm) | 0.04 | 0.07 | | | | 0.04 |
| Iron (ppm) | 0.7 | 0.3 | | | | <0.3 |
| Cobalt (ppm) | 3.88 | 0.42 | | | | 0.10 |
| Platinum lost (%) | 0.016 | 0.028 | | | | 0.016 |
| Iron lost (%) | 14 | 6 | | | | <6.0 |
| Cobalt lost (%) | 19.4 | 2.1 | | | | 0.5 |

TABLE 39

5.03% Pt/0.11% Fe/0.39% Co catalyst prepared by heat treatment at a maximum temperature of 950° C.

| | Run | | | | | |
|---|---|---|---|---|---|---|
| | 1 | 2 | 3 | 4 | 5 | 6 |
| Run Time (minutes) | 41.1 | 41.6 | 42.6 | 42.0 | 41.5 | 42.4 |
| Glyphosate (% by weight) | 5.490 | 5.730 | 5.680 | 5.700 | 5.700 | 5.720 |
| PMIDA (% by weight) | 0.002 | 0.001 | 0.001 | 0.002 | 0.002 | 0.002 |
| HCHO (% by weight) | 0.051 | 0.069 | 0.055 | 0.064 | 0.061 | 0.061 |
| HCOOH (% by weight) | 0.261 | 0.303 | 0.267 | 0.278 | 0.293 | 0.283 |
| IDA (% by weight) | 0.054 | 0.037 | 0.037 | 0.033 | 0.031 | 0.030 |
| Platinum (ppm) | 0.03 | 0.05 | | | | 0.03 |
| Iron (ppm) | 0.60 | 0.30 | | | | <0.3 |

TABLE 39-continued 5.03% Pt/0.11% Fe/0.39% Co catalyst prepared by heat treatment at a maximum temperature of 950° C.

| | Run | | | | | |
|---|---|---|---|---|---|---|
| | 1 | 2 | 3 | 4 | 5 | 6 |
| Cobalt (ppm) | 2.900 | 0.350 | | | | 0.090 |
| Platinum lost (%) | 0.012 | 0.02 | | | | 0.012 |
| Iron lost (%) | 12 | 6 | | | | <6 |
| Cobalt lost (%) | 14.5 | 1.75 | | | | 0.45 |

TABLE 40

4.98% Pt/0.11% Fe/0.39% Co catalyst prepared by heat treatment at a maximum temperature of 950° C.

| | Run | | | | | |
|---|---|---|---|---|---|---|
| | 1 | 2 | 3 | 4 | 5 | 6 |
| Run Time (minutes) | 39.1 | 40.7 | 40.2 | 39.8 | 39.7 | 39.5 |
| Glyphosate (% by weight) | 5.506 | 5.593 | 5.654 | 5.595 | 5.651 | 5.601 |
| PMIDA (% by weight) | 0.004 | DBNQ | DBNQ | 0.002 | 0.002 | 0.002 |
| HCHO (% by weight) | 0.059 | 0.066 | 0.055 | 0.062 | 0.060 | 0.061 |
| HCOOH (% by weight) | 0.282 | 0.296 | 0.304 | 0.310 | 0.307 | 0.309 |
| IDA (% by weight) | 0.050 | 0.035 | 0.033 | 0.031 | 0.029 | 0.027 |
| Platinum (ppm) | 0.03 | 0.04 | | | | 0.04 |
| Iron (ppm) | 0.6 | <0.3 | | | | 0.4 |
| Cobalt (ppm) | 2.73 | 0.37 | | | | 0.12 |
| Platinum lost (%) | 0.012 | 0.016 | | | | 0.016 |
| Iron lost (%) | 12 | <6.0 | | | | 8 |
| Cobalt lost (%) | 13.65 | 1.85 | | | | 0.6 |

DBNQ = Detected but not quantified.

TABLE 41

5% Pt/0.1% Fe/0.4% Co catalyst prepared by heat treatment at a maximum temperature of 950° C.

| | Run | | | | | |
|---|---|---|---|---|---|---|
| | 1 | 2 | 3 | 4 | 5 | 6 |
| Run Time (minutes) | 40.6 | 41.1 | 40.2 | 40.8 | 40.4 | 40.9 |
| Glyphosate (% by weight) | 5.634 | 6.192 | 5.813 | 5.843 | 5.770 | 5.858 |
| PMIDA (% by weight) | 0.003 | 0.002 | 0.003 | 0.002 | 0.003 | 0.003 |
| HCHO (% by weight) | 0.079 | 0.079 | 0.089 | 0.086 | 0.090 | 0.088 |
| HCOOH (% by weight) | 0.269 | 0.303 | 0.295 | 0.289 | 0.303 | 0.286 |
| IDA (% by weight) | 0.055 | 0.038 | 0.035 | 0.030 | 0.028 | 0.028 |
| Platinum (ppm) | 0.04 | 0.04 | | | | 0.04 |
| Iron (ppm) | 0.6 | <0.3 | | | | 0.3 |
| Cobalt (ppm) | 2.81 | 0.35 | | | | <0.2 |
| Platinum lost (%) | 0.016 | 0.016 | | | | 0.016 |
| Iron lost (%) | 12 | <6 | | | | 6 |
| Cobalt lost (%) | 14.05 | 1.75 | | | | <1 |

TABLE 42

5.01% Pt/0.12% Fe/0.47% Co catalyst prepared by heat treatment at a maximum temperature of 850° C.

| | Run | | | | | |
|---|---|---|---|---|---|---|
| | 1 | 2 | 3 | 4 | 5 | 6 |
| Run Time (minutes) | 41.8 | 42.5 | 42.4 | 41.9 | 42.5 | 45.0 |
| Glyphosate (% by weight) | 5.394 | 5.511 | 5.613 | 5.640 | 5.602 | 5.631 |
| PMIDA (% by weight) | 0.004 | 0.002 | 0.003 | 0.005 | 0.002 | 0.005 |
| HCHO (% by weight) | 0.045 | 0.040 | 0.042 | 0.038 | 0.034 | 0.039 |
| HCOOH (% by weight) | 0.156 | 0.172 | 0.182 | 0.184 | 0.177 | 0.187 |
| IDA (% by weight) | 0.099 | 0.062 | 0.052 | 0.046 | 0.054 | 0.047 |
| Platinum (ppm) | 0.06 | 0.06 | | | | 0.05 |
| Iron (ppm) | 0.9 | <0.3 | | | | <0.3 |
| Cobalt (ppm) | 5.40 | 0.54 | | | | 0.10 |
| Platinum lost (%) | 0.02 | 0.02 | | | | 0.02 |
| Iron lost (%) | 18 | <6.0 | | | | <6.0 |
| Cobalt lost (%) | 21.6 | 2.16 | | | | 0.4 |

TABLE 43

4.92% Pt/0.11% Fe/0.51% Co catalyst prepared by heat treatment at a maximum temperature of 950° C.

| | Run | | | | | |
|---|---|---|---|---|---|---|
| | 1 | 2 | 3 | 4 | 5 | 6 |
| Run Time (minutes) | 41.1 | 41.3 | 41.8 | 41.9 | 41.4 | 42.0 |
| Glyphosate (% by weight) | 5.530 | 5.690 | 5.670 | 5.740 | 5.700 | 5.690 |
| PMIDA (% by weight) | 0.004 | 0.003 | 0.002 | 0.003 | 0.004 | 0.003 |
| HCHO (% by weight) | 0.073 | 0.086 | 0.071 | 0.082 | 0.098 | 0.075 |
| HCOOH (% by weight) | 0.355 | 0.397 | 0.377 | 0.381 | 0.400 | 0.361 |
| IDA (% by weight) | 0.065 | 0.040 | 0.038 | 0.036 | 0.036 | 0.038 |
| Platinum (ppm) | 0.03 | 0.07 | | | | 0.06 |
| Iron (ppm) | 0.7 | <0.3 | | | | <0.3 |
| Cobalt (ppm) | 3.79 | 0.46 | | | | 0.15 |
| Platinum lost (%) | 0.012 | 0.028 | | | | 0.024 |
| Iron lost (%) | 14 | <6.0 | | | | <6.0 |
| Cobalt lost (%) | 15.16 | 1.84 | | | | 0.6 |

TABLE 44

4.88% Pt/0.26% Fe/0.27% Co catalyst prepared by heat treatment at a maximum temperature of 850° C.

| | Run | | | | | |
|---|---|---|---|---|---|---|
| | 1 | 2 | 3 | 4 | 5 | 6 |
| Run Time (minutes) | 41.5 | 42.0 | 42.6 | 43.2 | 42.8 | 42.4 |
| Glyphosate (% by weight) | 5.556 | 5.716 | 5.679 | 5.723 | 5.704 | 5.784 |
| PMIDA (% by weight) | 0.002 | 0.002 | 0.002 | 0.001 | 0.003 | 0.003 |
| HCHO (% by weight) | 0.025 | 0.026 | 0.019 | 0.019 | 0.033 | 0.052 |

TABLE 44-continued 4.88% Pt/0.26% Fe/0.27% Co catalyst prepared by heat treatment at a maximum temperature of 850° C.

| | Run | | | | | |
|---|---|---|---|---|---|---|
| | 1 | 2 | 3 | 4 | 5 | 6 |
| HCOOH (% by weight) | 0.162 | 0.164 | 0.174 | 0.176 | 0.164 | 0.175 |
| IDA (% by weight) | 0.097 | 0.059 | 0.053 | 0.048 | 0.044 | 0.042 |
| Platinum (ppm) | 0.06 | 0.06 | | | | 0.07 |
| Iron (ppm) | 2.50 | 0.80 | | | | 0.30 |
| Cobalt (ppm) | 3.95 | 0.35 | | | | 0.07 |
| Platinum lost (%) | 0.02 | 0.02 | | | | 0.03 |
| Iron lost (%) | 20 | 6.4 | | | | 2.4 |
| Cobalt lost (%) | 31.6 | 2.8 | | | | 0.56 |

TABLE 45

4.97% Pt/0.27% Fe/0.18% Co catalyst prepared by heat treatment at a maximum temperature of 950° C.

| | Run | | | | | |
|---|---|---|---|---|---|---|
| | 1 | 2 | 3 | 4 | 5 | 6 |
| Run Time (minutes) | 42.0 | 41.9 | 41.8 | 41.6 | 41.8 | 41.7 |
| Glyphosate (% by weight) | 5.470 | 5.676 | 5.778 | 5.706 | 5.747 | 5.788 |
| PMIDA (% by weight) | 0.002 | 0.002 | 0.003 | 0.003 | 0.002 | 0.005 |
| HCHO (% by weight) | 0.068 | 0.077 | 0.057 | 0.053 | 0.052 | 0.059 |
| HCOOH (% by weight) | 0.221 | 0.234 | 0.224 | 0.221 | 0.222 | 0.230 |
| IDA (% by weight) | 0.073 | 0.046 | 0.042 | 0.038 | 0.037 | 0.035 |
| Platinum (ppm) | 0.05 | 0.03 | | | | 0.05 |
| Iron (ppm) | 1.5 | <0.3 | | | | <0.3 |
| Cobalt (ppm) | 2.03 | 0.12 | | | | 0.05 |
| Platinum lost (%) | 0.02 | 0.012 | | | | 0.02 |
| Iron lost (%) | 15 | <3 | | | | <3 |
| Cobalt lost (%) | 16.24 | 0.96 | | | | 0.4 |

TABLE 46

4.93% Pt/0.11% Fe/0.09% Co catalyst prepared by heat treatment at a maximum temperature of 850° C.

| | Run | | | | | |
|---|---|---|---|---|---|---|
| | 1 | 2 | 3 | 4 | 5 | 6 |
| Run Time (minutes) | 37.6 | 38.7 | 39.7 | 39.2 | 39.5 | 39.5 |
| Glyphosate (% by weight) | 5.416 | 5.473 | 5.351 | 5.498 | 5.483 | 5.484 |
| PMIDA (% by weight) | 0.002 | 0.002 | 0.001 | 0.002 | 0.003 | 0.002 |
| HCHO (% by weight) | 0.084 | 0.109 | 0.068 | 0.075 | 0.101 | 0.076 |
| HCOOH (% by weight) | 0.324 | 0.369 | 0.369 | 0.390 | 0.408 | 0.399 |
| IDA (% by weight) | 0.033 | 0.020 | 0.017 | 0.016 | 0.014 | 0.013 |
| Platinum (ppm) | 0.05 | 0.07 | | | | 0.06 |
| Iron (ppm) | 0.5 | 0.3 | | | | <0.3 |
| Cobalt (ppm) | 0.63 | 0.09 | | | | 0.02 |

TABLE 46-continued 4.93% Pt/0.11% Fe/0.09% Co catalyst prepared by heat treatment at a maximum temperature of 850° C.

| | Run | | | | | |
|---|---|---|---|---|---|---|
| | 1 | 2 | 3 | 4 | 5 | 6 |
| Platinum lost (%) | 0.02 | 0.028 | | | | 0.024 |
| Iron lost (%) | 10 | 6 | | | | <6 |
| Cobalt lost (%) | 12.6 | 1.8 | | | | 0.4 |

The present invention is not limited to the above embodiments and can be variously modified. The above description of the preferred embodiments, including the Examples, is intended only to acquaint others skilled in the art with the invention, its principles, and its practical application so that others skilled in the art may adapt and apply the invention in its numerous forms, as may be best suited to the requirements of a particular use.

With reference to the use of the word(s) comprise or comprises or comprising in this entire specification (including the claims below), unless the context requires otherwise, those words are used on the basis and clear understanding that they are to be interpreted inclusively, rather than exclusively, and applicants intend each of those words to be so interpreted in construing this entire specification.

What is claimed is:

1. A process for the preparation of N-(phosphonomethyl) glycine or a salt thereof, the process comprising contacting N-(phosphonomethyl)iminodiacetic acid or a salt thereof with an oxidation catalyst and in the presence of oxygen, wherein the catalyst comprises a carbon support having metal particles at a surface of the carbon support, said metal particles comprising noble metal atoms alloyed with iron and cobalt atoms in the form of an alloy selected from the group consisting of an intermetallic compound, a substitutional alloy, a multiphasic alloy, an interstitial alloy, and combinations thereof, wherein the noble metal is selected from the group consisting of platinum, palladium, ruthenium, rhodium, iridium, silver, osmium, gold and combinations thereof, wherein:
   said noble metal constitutes from about 4 to about 8% by weight of said catalyst;
   iron constitutes at least about 0.05% by weight of the catalyst; and
   cobalt constitutes at least about 0.05% by weight of the catalyst.

2. A process as set forth in claim 1 wherein iron constitutes from about 0.25 to about 4% by weight of the catalyst.

3. A process as set forth in claim 2 wherein iron constitutes from about 0.25 to about 3% by weight of said catalyst.

4. A process as set forth in claim 3 wherein iron constitutes from about 0.25 to about 0.75% by weight of said catalyst.

5. A process as set forth in claim 4 wherein iron constitutes from about 0.25 to about 0.6% by weight of said catalyst.

6. A process as set forth in claim 1 wherein cobalt constitutes from about 0.25 to about 4% by weight of said catalyst.

7. A process as set forth in claim 6 wherein cobalt constitutes from about 0.25 to about 3% by weight of said catalyst.

8. A process as set forth in claim 7 wherein cobalt constitutes from about 0.25 to about 0.75% by weight of said catalyst.

9. A process as set forth in claim 8 wherein cobalt constitutes from about 0.25 to about 0.6% by weight of said catalyst.

10. A process as set forth in claim 1 wherein said noble metal constitutes from about 4 to about 6% by weight of said catalyst.

11. A process as set forth in claim 1 wherein the noble metal is platinum.

12. A process as set forth in claim 1 wherein the reaction is conducted in a continuous reactor system.

13. A process as set forth in claim 1 wherein the contacting is carried out at a pressure of from about 30 to about 130 psig.

14. A process as set forth in claim 1 wherein the contacting is carried out at a temperature of from about 80 to about 110° C.

15. A process as set forth in claim 1 wherein the contacting is carried out in a solution or slurry having a pH of less than 7.

16. A process as set forth in claim 15 wherein the contacting is carried out in a solution or slurry having a pH of less than 3.

17. A process as set forth in claim 16 wherein the contacting is carried out in a solution or slurry having a pH of from about 1 to about 2.

18. A process as set forth in claim 1 wherein said metal particles comprise noble metal atoms alloyed with iron and cobalt atoms in the form of an intermetallic compound.

19. A process as set forth in claim 1 wherein said metal particles comprise noble metal atoms alloyed with iron and cobalt atoms in the form of a substitutional alloy.

20. A process as set forth in claim 1 wherein said metal particles comprise noble metal atoms alloyed with iron and cobalt atoms in the form of a multiphasic alloy.

21. A process as set forth in claim 1 wherein said metal particles comprise noble metal atoms alloyed with iron and cobalt atoms in the form of an interstitial alloy.

22. A process as set forth in claim 1 wherein iron constitutes from about 0.25 to about 0.75% by weight of said catalyst and cobalt constitutes from about 0.25 to about 0.75% by weight of said catalyst.

23. A process as set forth in claim 1 wherein the carbon support has a surface area of from about 500 to about 2100 $m^2/g$.

24. A process as set forth in claim 23 wherein the carbon support has a surface area of from about 500 to about 1500 $m^2/g$.

25. A process as set forth in claim 24 wherein the carbon support has a surface area of from about 1000 to about 1500 $m^2/g$.

26. A process for the preparation of N-(phosphonomethyl) glycine or a salt thereof, the process comprising contacting N-(phosphonomethyl)iminodiacetic acid or a salt thereof with an oxidation catalyst and in the presence of oxygen, wherein the catalyst comprises a carbon support having metal particles at a surface of the carbon support, said metal particles comprising noble metal atoms alloyed with iron and cobalt atoms in the form of an alloy selected from the group consisting of an intermetallic compound, a substitutional alloy, a multiphasic alloy, an interstitial alloy, and combinations thereof, wherein the noble metal is selected from the group consisting of platinum, palladium, ruthenium, rhodium, iridium, silver, osmium, gold and combinations thereof, wherein:

said noble metal constitutes from about 2 to about 8% by weight of said catalyst;
iron constitutes at least about 0.05% by weight of the catalyst; and
cobalt constitutes from about 0.25 to about 0.75% by weight of the catalyst.

27. A process as set forth in claim 26 wherein iron constitutes from about 0.25 to about 3% by weight of the catalyst.

28. A process as set forth in claim 27 wherein iron constitutes from about 0.25 to about 0.75% by weight of the catalyst.

29. A process as set forth in claim 28 wherein iron constitutes from about 0.25 to about 0.6% by weight of the catalyst.

30. A process as set forth in claim 26 wherein cobalt constitutes from about 0.25 to about 0.6% by weight of the catalyst.

31. A process as set forth in claim 26 wherein said noble metal constitutes from about 4 to about 8% by weight of said catalyst.

32. A process as set forth in claim 31 wherein said noble metal constitutes from about 4 to about 6% by weight of said catalyst.

33. A process as set forth in claim 26 wherein the noble metal is platinum.

34. A process as set forth in claim 26 wherein iron constitutes from about 0.25 to about 4% by weight of the catalyst.

35. A process as set forth in claim 26 wherein said metal particles comprise noble metal atoms alloyed with iron and cobalt atoms in the form of an intermetallic compound.

36. A process as set forth in claim 26 wherein said metal particles comprise noble metal atoms alloyed with iron and cobalt atoms in the form of a substitutional alloy.

37. A process as set forth in claim 26 wherein said metal particles comprise noble metal atoms alloyed with iron and cobalt atoms in the form of a multiphasic alloy.

38. A process as set forth in claim 26 wherein said metal particles comprise noble metal atoms alloyed with iron and cobalt atoms in the form of an interstitial alloy.

39. A process as set forth in claim 26 wherein the carbon support has a surface area of from about 500 to about 2100 $m^2/g$.

40. A process as set forth in claim 39 wherein the carbon support has a surface area of from about 500 to about 1500 $m^2/g$.

41. A process as set forth in claim 40 wherein the carbon support has a surface area of from about 1000 to about 1500 $m^2/g$.

* * * * *

UNITED STATES PATENT AND TRADEMARK OFFICE
CERTIFICATE OF CORRECTION

| | | |
|---|---|---|
| PATENT NO. | : 8,703,639 B2 | Page 1 of 1 |
| APPLICATION NO. | : 11/575370 | |
| DATED | : April 22, 2014 | |
| INVENTOR(S) | : Wan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2135 days.

Signed and Sealed this
Eleventh Day of August, 2015

Michelle K. Lee
*Director of the United States Patent and Trademark Office*